US009751975B2

(12) United States Patent
Cruce et al.

(10) Patent No.: US 9,751,975 B2
(45) Date of Patent: Sep. 5, 2017

(54) LIQUID MOLDING COMPOSITIONS

(71) Applicant: MATERIA, INC., Pasadena, CA (US)

(72) Inventors: Christopher J. Cruce, Poway, CA (US); Michael A. Giardello, Pasadena, CA (US); Mark S. Trimmer, Monrovia, CA (US); Anthony R. Stephen, South Pasadena, CA (US); Paul W. Boothe, Brooklyn, NY (US); Brian Edgecombe, Anaheim, CA (US); Jason L. Moore, Altadena, CA (US)

(73) Assignee: MATERIA, INC., Pasadena, CA (US)

( * ) Notice: Subject to any disclaimer, the term of this patent is extended or adjusted under 35 U.S.C. 154(b) by 0 days.

(21) Appl. No.: 14/899,165

(22) PCT Filed: Jul. 3, 2014

(86) PCT No.: PCT/US2014/045440
§ 371 (c)(1),
(2) Date: Dec. 17, 2015

(87) PCT Pub. No.: WO2015/003147
PCT Pub. Date: Jan. 8, 2015

(65) Prior Publication Data
US 2016/0257779 A1  Sep. 8, 2016

Related U.S. Application Data

(60) Provisional application No. 61/842,885, filed on Jul. 3, 2013.

(51) Int. Cl.
C07C 13/38 (2006.01)
C08G 61/00 (2006.01)
C08G 61/08 (2006.01)
C08F 4/80 (2006.01)
C08J 5/04 (2006.01)
C07C 13/61 (2006.01)

(52) U.S. Cl.
CPC ............... *C08G 61/08* (2013.01); *C08F 4/80* (2013.01); *C08J 5/043* (2013.01); *C07C 13/38* (2013.01); *C07C 13/61* (2013.01); *C08G 2261/3325* (2013.01); *C08G 2261/418* (2013.01); *C08J 2323/20* (2013.01)

(58) Field of Classification Search
CPC ..... C07C 13/61; C07C 13/605; C07C 13/573; C07C 13/547; C07C 13/38
See application file for complete search history.

(56) References Cited

U.S. PATENT DOCUMENTS

| 3,701,812 | A |   | 10/1972 | Gebhart et al. |          |
|-----------|---|---|---------|----------------|----------|
| 4,023,980 | A |   | 5/1977  | Prillieux et al. |        |
| 4,401,837 | A |   | 8/1983  | Burdette et al. |         |
| 4,703,098 | A | * | 10/1987 | Matlack ......... | C08G 61/04 526/283 |
| 4,751,337 | A | * | 6/1988  | Espy ............... | C08G 61/08 526/142 |
| 4,843,185 | A |   | 6/1989  | Ware et al. |              |
| 4,899,005 | A | * | 2/1990  | Lane ............... | C08G 61/08 526/127 |
| 4,906,797 | A | * | 3/1990  | Lane, Jr. ......... | C08G 61/08 585/1 |
| 4,952,348 | A |   | 8/1990  | Ishimaru et al. |         |
| 5,011,730 | A |   | 4/1991  | Tenney et al. |           |
| 5,204,427 | A |   | 4/1993  | Torii et al. |             |
| 5,312,940 | A |   | 5/1994  | Grubbs et al. |           |
| 5,342,909 | A |   | 8/1994  | Grubbs et al. |           |
| 5,391,658 | A |   | 2/1995  | Lane et al. |              |
| 5,939,504 | A |   | 8/1999  | Woodson, Jr. et al. |     |
| 5,977,393 | A |   | 11/1999 | Grubbs et al. |           |
| 6,284,852 | B1 |  | 9/2001  | Lynn et al. |              |
| 6,310,121 | B1 |  | 10/2001 | Woodson, Jr. et al. |     |
| 6,436,476 | B1 |  | 8/2002  | Sage, Jr. |                |
| 6,486,279 | B2 |  | 11/2002 | Lynn et al. |              |
| 6,515,084 | B2 |  | 2/2003  | Grubbs et al. |           |
| 6,525,125 | B1 |  | 2/2003  | Giardello et al. |        |
| 6,552,139 | B1 |  | 4/2003  | Herrmann et al. |         |
| 6,613,910 | B2 |  | 9/2003  | Grubbs et al. |           |
| 6,635,768 | B1 |  | 10/2003 | Herrmann et al. |         |
| 6,759,537 | B2 |  | 7/2004  | Grubbs et al. |           |
| 6,787,620 | B2 |  | 9/2004  | Herrmann et al. |         |
| 6,838,489 | B2 |  | 1/2005  | Bell et al. |              |
| 6,890,650 | B2 |  | 5/2005  | Hedden |                   |
| 6,908,970 | B2 |  | 6/2005  | Tsunogae et al. |         |
| 7,294,717 | B2 |  | 11/2007 | Herrmann et al. |         |
| 7,329,758 | B1 |  | 2/2008  | Grubbs et al. |           |
| 7,378,528 | B2 |  | 5/2008  | Herrmann et al. |         |
| 7,652,145 | B2 |  | 1/2010  | Herrmann et al. |         |
| 7,671,224 | B2 |  | 3/2010  | Winde et al. |            |
| 7,687,635 | B2 |  | 3/2010  | Verpoort et al. |         |
| 2003/0055262 | A1 | | 3/2003 | Grubbs et al. |           |
| 2005/0261451 | A1 | | 11/2005 | Ung et al. |             |
| 2007/0043188 | A1 | | 2/2007 | Schaubroeck et al. |      |
| 2008/0293905 | A9 | | 11/2008 | Schaubroeck et al. |     |
| 2011/0160472 | A1 | | 6/2011 | Lemke et al. |            |
| 2014/0296436 | A1 | * | 10/2014 | Hwang ............ | C08F 36/02 525/55 |
| 2015/0165652 | A1 | * | 6/2015 | Giardello ........ | C25B 9/00 204/279 |
| 2016/0244632 | A1 | * | 8/2016 | Cruce ............ | C08G 61/08 |

FOREIGN PATENT DOCUMENTS

EP  271 007   *  6/1988   ............. C07C 13/61
EP  0271007 A2   6/1988
(Continued)

OTHER PUBLICATIONS

Pamlová et al. Chemical Engineering Science, 2001, 56, 927-935.*
(Continued)

*Primary Examiner* — Rip A Lee
(74) *Attorney, Agent, or Firm* — J. A. Lindeman & Co., PLLC

(57) ABSTRACT

The present invention relates to methods and compositions for olefin metathesis. More particularly, the present invention relates to methods and compositions for ring opening metathesis polymerization (ROMP) reactions and the manufacture of polymer articles and/or polymer composite articles via ROMP Polymer products produced via the metathesis reactions of the invention may be utilized in a wide range of materials and composite applications. The invention has utility in the fields of polymer and materials chemistry and manufacture.

14 Claims, No Drawings

(56) References Cited

FOREIGN PATENT DOCUMENTS

| EP | 0271007 | B2 | | 6/1988 | |
|---|---|---|---|---|---|
| EP | 313 838 | A2 | * | 5/1989 | ............ C08G 61/08 |
| EP | 0313838 | A2 | | 5/1989 | |
| EP | 0271007 | B1 | | 3/1994 | |
| EP | 1757613 | B1 | | 1/2011 | |
| EP | 1577282 | B1 | | 6/2011 | |
| WO | 00/46257 | A1 | | 8/2000 | |
| WO | 02/079208 | A2 | | 10/2002 | |
| WO | 02/011455 | A1 | | 2/2003 | |
| WO | 2010/037550 | A1 | | 8/2010 | |
| WO | 2012/174502 | A2 | | 12/2012 | |
| WO | 2013/022242 | A2 | | 2/2013 | |

OTHER PUBLICATIONS

Bondaletov et al., "Studying cyclopentadiene dimerization in high-boiling fractions of pyrolysis liquid products by means of NMR H-Spectroscopy," Bulletin of the TOMSK Polytechnic University, 2007, vol. 311, No. 3, pp. 98-101.

Hahn et al., "Olefins coordinated at a highly electrophilic site—dicationic palladium (II) complexes and their equilibrium reactions with nucleophiles," Eur. J. Inorg. Chem., 2001, pp. 419-429.

Han et al., Endo-to exo-isomerization of dicyclopentadiene over zeolites, Applied Catalysis A: General 367, 2009, pp. 34-88.

A. Behr and W. Keim, "Novel trimerization of cyclopentadiene with a homogeneous, bifunctional palladium-Acid aatalyst system," Angew. Chem. Int. Ed. Engl. 24, 1985, No. 4, pp. 314-315.

J. Krupka "Kinetics of thermal dimerizations of cyclopentadiene and methylcyclopentadienes and their codimerization," Petroleum & Coal 52, (4), 2010, pp. 290-306.

Li et al., "Product distribution of tricyclopentadiene from cycloaddition of dicyclopentadiene and cyclopentadiene: A theoretical and experimental study," Fuel 89, 2010, pp. 2522-2527.

Palmova et al., "Experimental and modeling studies of oligomerization and copolymerization of dicyclopentadiene," chemical Engineering Science 56, 2001, pp. 927-935.

Rule et al., "ROMP Reactivity of endo- and exo-Dicyclopentadiene," Macromolecules 2002, 35, pp. 7878-7882.

International Search Report and Written Opinion in PCT/US2014/045440, dated Oct. 15, 2014.

International Preliminary Report on Patentability in PCT/US2014/045440, dated Jan. 14, 2016.

Sanford et al., "New Insights into the Mechanism of Ruthenium-Catalyzed Olefin Metathesis Reactions," J. Am. Chem. Soc., 2001, 123, pp. 749-750 with supportive information.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," Org. Lett., 1999, vol. 1, No. 6. pp. 953-956.

Schwab et al., "Synthesis and Applications of RuCl2(=CHR')(PR3)2: The Influence of the Alkylidene Moiety on Metathesis Activity," J. Am. Chem. Soc., 1996, 118, pp. 100-110 and supporting information.

Extended European Search Report in EP Application No. 14820242, dated Dec. 5, 2016.

* cited by examiner

LIQUID MOLDING COMPOSITIONS

CROSS-REFERENCE TO RELATED APPLICATION

This application claims the benefit of U.S. Provisional Patent Application No. 61/842,885, filed Jul. 3, 2013, the contents of which is incorporated herein by reference in its entirety.

TECHNICAL FIELD

The present invention relates to methods and compositions for olefin metathesis. More particularly, the present invention relates to methods and compositions for ring opening metathesis polymerization (ROMP) reactions and the manufacture of polymer articles and/or polymer composite articles via ROMP. Polymer products produced via the metathesis reactions of the invention may be utilized in a wide range of materials and composite applications. The invention has utility in the fields of polymer and materials chemistry and manufacture.

BACKGROUND

The molding of thermoset polymers is a technologically and commercially important processing technique. In one known version of this technique, a liquid cyclic olefin monomer resin is combined with at least one metal carbene olefin metathesis catalyst to form a ROMP composition, and the ROMP composition is added (e.g., poured, cast, infused, injected, etc.) into a mold. The ROMP composition is subjected to conditions effective to polymerize the ROMP composition and on completion the molded article is subjected to any optional post cure processing that may be required. As is known in the art, the liquid cyclic olefin monomer resin may optionally contain added modifiers, fillers, reinforcements, flame retardants, pigments, etc. Examples of such prior art ROMP compositions are disclosed in U.S. Pat. Nos. 5,342,909; 6,310,121; 6,515,084; 6,525,125; 6,759,537; 7,329,758, etc.

Commercially important cyclic olefin monomer resins generally comprise readily available and inexpensive cyclic olefins such as norbornene monomers, particularly dicyclopentadiene (DCPD). Unfortunately, high purity DCPD melts at 32° C.-34° C. and is thus a solid at room temperature (typically 20-25° C.). Therefore, high purity DCPD must be heated during its formulation with catalyst(s) and other additives, and transported through heat-jacketed lines to maintain a liquid state for use in many polymer molding techniques such as RIM (Reaction Injection Molding), RTM (Resin Transfer Molding), and VARTM (Vacuum Assisted Resin Transfer Molding).

It is known in the art that the melting point of DCPD can be depressed by adding an adulterant in the form of higher cyclopentadiene oligomers that are copolymerizable with dicyclopentadiene such as trimer of cyclopentadiene (tricyclopentadiene). In fact, commercially available liquid DCPD monomer resins for use in molding of polymer articles typically contain between 10%-30% by weight of tricyclopentadiene, and lesser amounts of higher oligomers of cyclopentadiene such as tetramers and pentamers of cyclopentadiene (e.g., tetracyclopentadiene and pentacyclopentadiene).

Liquid DCPD monomer resins for use in molding polymer articles containing higher amounts of cyclopentadiene trimer have been reported in the literature. European Pat. No. EP0271007B2 and U.S. Pat. No. 4,703,098 disclosed liquid mixtures containing (a) 52% by weight DCPD, 43.25% by weight tricyclopentadiene, and 4.75% by weight tetracyclopentadiene; and (b) 42% by weight DCPD, 51.5% by weight tricyclopentadiene, 6.5% by weight tetracyclopentadiene. However, the inventors have discovered that below 40° C., particularly at or below room temperature, solids precipitate out of such mixtures. This is particularly problematic as below 40° C., particularly at or below room temperature such prior art resin compositions are not suitable for use in preparing composite articles, particularly using resin infusion techniques, such as VARTM, as the solids may clog the infusion ports and/or equipment and may also act to reduce infusion of the resin into the composite substrate material. Furthermore, these solids may also act to clog or foul equipment such as material supply lines and/or injection ports utilized in reaction injection molding (RIM) techniques, when molding polymer articles and/or polymer composite articles.

To successfully mold a polymer article and/or polymer composite article using liquid DCPD monomer resins, it is important that the molded article be free or substantially free of defects (e.g., unwanted pores, cavities, bubbles, voids, knit lines and/or internal stress fractures). This issue is particularly important as molded polymer articles and/or polymer composite articles possessing defects will either require repair or need to be discarded, which in either situation leads to increased manufacturing costs.

In a typical molding operation the temperature of the pre-catalyzed liquid DCPD monomer resin is typically below 40° C., and preferentially at or below room temperature. Heating the pre-catalyzed liquid DCPD monomer resin above room temperature, particularly above 40° C., generally reduces the pot life of the ROMP composition (catalyzed monomer resin), making it difficult to adequately fill the mold and/or infuse the substrate materials, particularly when making large polymer articles and/or large polymer composite articles. In addition, heating of the liquid DCPD monomer resin may require special equipment (e.g., heated tanks and/or lines) which adds to the overall cost of molding ROMP polymer articles and/or ROMP polymer composite articles. Methods and additives for controlling the pot life of catalyzed liquid cyclic olefin monomer resins (e.g., liquid DCPD monomer resins) are known; however, generally at temperatures above 40° C. large amounts of additives may be required to provide adequate pot life, but the use of large amounts of such additives may detrimentally affect the thermal and mechanical properties of the molded polymer article and/or polymer composite article, thereby requiring the need for additional optional post cure processing which also increases the overall cost of molding ROMP polymer articles and/or ROMP polymer composite articles.

Typically, following catalyzation of the liquid DCPD monomer resin to form a ROMP composition, the polymerization of the monomer resin progresses and the viscosity of the ROMP composition increases, progressing from a liquid state, through a gel state, to the final hard polymer. At some point during the progression, the temperature generally begins to increase rapidly leading to a sharp exotherm. A general issue with molding polymer articles using liquid DCPD monomer resins is that during the exotherm phase of the polymerization cycle volatilization of dicyclopentadiene and/or other low boiling compounds which may be present in the liquid DCPD monomer resin (e.g., cyclopentadiene monomer) often lead to the formation of defects in the interior and/or on the surface of the molded polymer article and/or polymer composite article. It is known in the art that low molecular weight, low boiling hydrocarbon compounds (e.g., cyclopentadiene monomer) can be removed from liquid DCPD monomer resin by vacuum stripping and/or inert gas sparging. However, the inventors have discovered that removal of low molecular weight, low boiling hydrocarbon compounds such as cyclopentadiene monomer alone is not sufficient to reduce and/or eliminate defect formation in the interior and/or on the surface of molded ROMP polymer articles and/or ROMP polymer composite articles.

While there have been attempts to modulate the exotherm temperature (e.g., through manipulation of the mold temperature and/or addition of additives) to control defect formation, it is typically advantageous to allow the ROMP composition to achieve a maximum (high) exotherm temperature so as to optimize the thermal and mechanical properties of the molded polymer article and/or polymer composite article, thereby reducing and/or eliminating the need for additional optional post cure processing.

Therefore, it would be useful and commercially important to be able to rapidly heat the ROMP composition in a mold (e.g., at a rate greater than 0.5° C./min) and/or add the ROMP composition to a mold preheated at a temperature of about 60° C. to 200° C., either of which would allow the ROMP composition to achieve a maximum (high) exotherm temperature and additionally allow for a reduction in overall cycle time. This reduction in cycle time provides for an economic advantage in that more polymer articles and/or polymer composite articles can be made during the same time period. In other words, it would be preferable to be able to add the ROMP composition to a heated mold and/or begin heating the ROMP composition as soon as possible once the mold is filled and/or the composite substrate material is infused with the ROMP composition. More particularly, it would be preferable to be able to add a ROMP composition, having an initial temperature below 40° C., preferably at or below room temperature, to a mold heated at 60° C. to 200° C. and/or begin heating the ROMP composition in the mold at a rate greater than 0.5° C./min as soon as the mold is filled and/or the composite substrate material is infused with the ROMP composition.

Generally, however, it has been observed that if liquid DCPD monomer resin compositions, containing 10%-30% cyclopentadiene trimer are utilized in a ROMP composition to mold polymer articles and/or polymer composite articles, the resultant molded polymer article and/or polymer composite article will typically contain defects, particularly if such a ROMP composition at an initial temperature below 40° C., preferably at or below room temperature, is added to a mold preheated at a temperature of about 60° C. to 200° C. and/or if the mold is rapidly heated at a rate greater than 0.5° C./min.

Therefore, despite the advances achieved in the art, there is a need for liquid cyclic olefin monomer resins, particularly resins which are storage stable homogenous liquids, which can be combined with a catalyst composition comprising at least one metal carbene olefin metathesis catalyst to form a ROMP composition, where the ROMP composition may be added to a preheated mold and/or the mold may be rapidly heated to prepare molded polymer articles and/or polymer composite articles, where the resultant molded polymer articles and/or polymer composite articles are free or substantially free of defects.

More particularly, there is a need for liquid DCPD resin compositions that are stable homogenous liquids between 39° C. to 10° C., which can be combined with a catalyst composition comprising at least one metal carbene olefin metathesis catalyst to form a ROMP composition, where the ROMP composition is below 40° C., preferably at or below room temperature, and the ROMP composition may be added to a mold preheated to 60° C. to 200° C. and/or the mold may be rapidly heated (e.g., at a rate greater than 0.5° C./min) to prepare molded polymer articles and/or polymer composite articles, where the resultant molded polymer articles and/or polymer composite articles are free or substantially free of defects.

The present invention is directed to addressing one or more the aforementioned concerns.

SUMMARY

It is an object of the present invention to provide liquid cyclic olefin monomer resins, particularly resins which are storage stable homogenous liquids, methods using such resins, and use of such resins to prepare ROMP compositions for the manufacture of polymer articles and/or polymer composite articles via ROMP, where the polymer articles and/or polymer composite articles are free or substantially free of defects.

More particularly, it is an object of the present invention to provide cyclic olefin compositions and/or resin compositions that are stable homogenous liquids between 39° C. to 10° C., which can be combined with a catalyst composition comprising at least one metal carbene olefin metathesis catalyst to form a ROMP composition, where the ROMP composition is below 40° C., preferably, at or below room temperature, and the ROMP composition may be added to a mold preheated to 60° C. to 200° C. and/or the mold may be rapidly heated (e.g., at a rate greater than 0.5° C./min) to prepare molded polymer articles and/or polymer composite articles, where the resultant molded polymer articles and/or polymer composite articles are free or substantially free of defects.

The inventors have discovered that a resin composition comprising a cyclic olefin composition, wherein the cyclic olefin composition comprises 35%-70% by weight tricyclopentadiene, when combined with a catalyst composition comprising at least one metal carbene olefin metathesis catalyst, enables the preparation of polymer articles and/or polymer composite articles that are free or substantially free of visual defects, either internal defects and/or surface defects (e.g., unwanted pores, cavities, bubbles, voids, knit lines, and/or internal stress fractures). In particular, the present invention mitigates against issues related to defects that are thought to be caused by volatilization of low boiling compounds present in the cyclic olefin composition or generated during the polymerization (exotherm) cycle. Defects which are thought to be caused by volatilization of low boiling compounds present in the cyclic olefin composition or generated during polymerization are a particular issue with metal carbene olefin metathesis catalysts (polymerization catalysts) of the invention, particularly ruthenium metal carbene olefin metathesis catalysts of the invention. This is especially the case with ruthenium metal carbene metathesis catalysts which are commonly called Second Generation Grubbs catalysts and/or Grubbs-Hoveyda catalysts. Second Generation Grubbs Catalysts and/or Grubbs-Hoveyda catalysts generally propagate polymerization (e.g., ROMP) of cyclic olefins faster than ruthenium metal carbene olefin metathesis catalysts which are commonly called First Generation Grubbs catalysts. Without being bound by theory, during a ROMP reaction, defects that are thought to be caused by volatilization of low boiling compounds are exacerbated with faster propagating catalysts (e.g., Second Generation Grubbs Catalysts and/or Grubbs-Hoveyda catalysts) compared to slower propagating catalysts (e.g., First Generation Grubbs Catalysts).

More particularly, the inventors have discovered that a resin composition comprising a cyclic olefin composition, wherein the cyclic olefin composition comprises 35.00% to 70.00% by weight tricyclopentadiene, 0.01% to 4.00% by weight tetracyclopentadiene, and 64.99% to 26.00% by weight dicyclopentadiene, when combined with a catalyst composition comprising at least one metal carbene olefin metathesis catalyst, enables the preparation of polymer articles and/or polymer composite articles that are either free of visual defects, substantially free of visual defects, or contain fewer visual defects, either internal defects and/or surface defects (e.g., unwanted pores, cavities, bubbles, voids, knit lines, and/or internal stress fractures) than the same articles prepared using liquid DCPD monomer resins containing between 10%-30% by weight tricyclopentadiene. In particular, the present invention mitigates against issues related to defects that are thought to be caused by volatilization of dicyclopentadiene and/or other low boiling compounds present in the cyclic olefin composition or generated during the polymerization (exotherm) cycle. Defects which are thought to be caused by volatilization of dicyclopentadiene and/or other low boiling compounds present in the cyclic olefin composition or generated during polymerization are a particular issue with metal carbene olefin metathesis catalysts (polymerization catalysts) of the invention, particularly ruthenium metal carbene olefin metathesis catalysts of the invention. This is especially the case with ruthenium metal carbene metathesis catalysts which are commonly called Second Generation Grubbs catalysts and/or Grubbs-Hoveyda catalysts. Second Generation Grubbs Catalysts and/or Grubbs-Hoveyda catalysts generally propagate polymerization (e.g., ROMP) of cyclic olefins faster than ruthenium metal carbene olefin metathesis catalysts which are commonly called First Generation Grubbs catalysts. Without being bound by theory, during a ROMP reaction, defects that are thought to be caused by volatilization of dicyclopentadiene and/or other low boiling compounds are exacerbated with faster propagation catalysts (e.g., Second Generation Grubbs Catalysts and/or Grubbs-Hoveyda catalysts) compared to slower propagation catalysts (e.g., First Generation Grubbs Catalysts). In other words, during a ROMP reaction, liquid DCPD monomer resins containing 10%-30% by weight tricyclopentadiene show a greater tendency to possess volatilization related defects when catalyzed with faster propagating catalysts (e.g., Second Generation Grubbs Catalysts and/or Grubbs-Hoveyda catalysts) compared to slower propagating catalysts (e.g., First Generation Grubbs Catalysts).

Generally, liquid cyclic olefin compositions of the invention having tricyclopentadiene content at or above 35 percent by weight have decreased flammability (e.g., increased flashpoint) compared to the commercially available liquid DCPD monomer resins. Additionally, the inventors have discovered that liquid cyclic olefin compositions of the invention may offer an additional benefit in that such cyclic olefin compositions may enable the preparation of liquid resin compositions (e.g. liquid DCPD resin compositions) which may have a flashpoint greater than 60.5° C. Liquid resin compositions which have a flashpoint greater than 60.5° C. are designated as combustible liquids according to Globally Harmonized System (GHS) flammable and combustible liquid criteria. Liquid resin compositions which have a flashpoint less than 60.5° C. are designated as flammable liquids according to GHS flammable liquid and combustible liquid criteria. Liquid resin compositions which are designated as combustible liquids instead of flammable liquids offer several advantages/benefits including ease of handling, reduced transportation costs, and additional safety features, as well as other advantages/benefits.

Generally, liquid cyclic olefin compositions of the invention having tricyclopentadiene content at or above 35 percent by weight have decreased toxicity compared to the commercially available liquid DCPD monomer resins. In particular, the inventors have discovered that liquid cyclic olefin compositions of the invention may offer an additional benefit in that such cyclic olefin compositions may enable the preparation of liquid resin compositions (e.g., liquid DCPD resin compositions) which may be designated as H331 (toxic if inhaled) instead of H330 (fatal if inhaled) according to Globally Harmonized System (GHS) criteria. For example, the following cyclic olefin composition should be designated as H331 (toxic if inhaled): DCPD (40 wt %), tricyclopentadiene (57 wt %), tetracyclopentadiene (3 wt %). For example, the following resin composition should be designated as H331 (toxic if inhaled): DCPD (43 wt %), tricyclopentadiene (53 wt %), tetracyclopentadiene (4 wt %), Ethanox 4702 (3 phr), 5-vinyl-2-norbornene (1 wt %), triphenylphosphine (0.6 phr), elastomeric impact modifier (4 phr). For example, the following resin composition should be designated as H331 (toxic if inhaled): DCPD (37 wt %), tricyclopentadiene (60 wt %), tetracyclopentadiene (3 wt %), liquid MDI (4 phr). For example, the following resin composition should be designated as H331 (toxic if inhaled): DCPD (41 wt %), tricyclopentadiene (57 wt %), tetracyclopentadiene (2 wt %), Ethanox 4702 (2 phr), 5-vinyl-2-norbornene (1 phr), triphenylphosphine (0.6 phr), and adhesion promoter composition (A) (4 phr).

One embodiment of the invention provides a cyclic olefin composition comprising, 35.00% to 70.00% by weight tricyclopentadiene, 0.01% to 4.00% by weight tetracyclopentadiene, and 64.99% to 26.00% by weight dicyclopentadiene.

Another embodiment of the invention provides a cyclic olefin composition comprising 40.00% to 65.00% by weight tricyclopentadiene, 0.01% to 3.50% by weight tetracyclopentadiene, and 59.99% to 31.50% by weight dicyclopentadiene.

Another embodiment of the invention provides a cyclic olefin composition comprising 40.00% to 60.00% by weight tricyclopentadiene, 0.01% to 3.00% by weight tetracyclopentadiene, and 59.99% to 37.00% by weight dicyclopentadiene.

Another embodiment of the invention provides a cyclic olefin composition comprising, 35.00 to 70.0 weight percent tricyclopentadiene, 0.01 to 4.00 weight percent tetracyclopentadiene, and 64.99 to 26.00 weight percent dicyclopentadiene, where weight percent is determined by gas chromatography.

Another embodiment of the invention provides a cyclic olefin composition comprising 40.00 to 65.00 weight percent tricyclopentadiene, 0.01 to 3.50 weight percent tetracyclopentadiene, and 59.99 to 31.50 weight percent dicyclopentadiene, where weight percent is determined by gas chromatography.

Another embodiment of the invention provides a cyclic olefin composition comprising 40.00 to 60.00 weight percent tricyclopentadiene, 0.01 to 3.00 weight percent tetracyclopentadiene, and 59.99 to 37.00 weight percent dicyclopentadiene, where weight percent is determined by gas chromatography.

Another embodiment of the invention provides a cyclic olefin composition comprising, 35.00% to 70.00% by weight tricyclopentadiene, 0.01% to 4.00% by weight tetracyclopentadiene, and 64.99% to 26.00% by weight dicyclopentadiene, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a cyclic olefin composition comprising, 40.00% to 65.00% by weight tricyclopentadiene, 0.01% to 3.50% by weight tetracyclopentadiene, and 59.99% to 31.50% by weight dicyclopentadiene, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a cyclic olefin composition comprising, 40.00% to 60.00% by weight tricyclopentadiene, 0.01% to 3.00% by weight tetracyclopentadiene, and 59.99% to 37.00% by weight dicyclopentadiene, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a resin composition comprising a cyclic olefin composition, wherein the cyclic olefin composition comprises 35.00% to 70.00% by weight tricyclopentadiene, 0.01% to 4.00% by weight tetracyclopentadiene, and 64.99% to 26.00% by weight dicyclopentadiene.

Another embodiment of the invention provides a resin composition comprising a cyclic olefin composition, wherein the cyclic olefin composition comprises 40.00% to 65.00% by weight tricyclopentadiene, 0.01% to 3.50% by weight tetracyclopentadiene, and 59.99% to 31.50% by weight dicyclopentadiene.

Another embodiment of the invention provides a resin composition comprising a cyclic olefin composition, wherein the cyclic olefin composition comprises 40.00% to 60.00% by weight tricyclopentadiene, 0.01% to 3.00% by weight tetracyclopentadiene, and 59.99% to 37.00% by weight dicyclopentadiene.

Another embodiment of the invention provides a resin composition comprising a cyclic olefin composition, wherein the cyclic olefin composition comprises 35.00% to 70.00% by weight tricyclopentadiene, 0.01% to 4.00% by weight tetracyclopentadiene, and 64.99% to 26.00% by weight dicyclopentadiene, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a resin composition comprising a cyclic olefin composition, wherein the cyclic olefin composition comprises 40.00% to 65.00% by weight tricyclopentadiene, 0.01% to 3.50% by weight tetracyclopentadiene, and 59.99% to 31.50% by weight dicyclopentadiene, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a resin composition comprising a cyclic olefin composition, wherein the cyclic olefin composition comprises 40.00% to 60.00% by weight tricyclopentadiene, 0.01% to 3.00% by weight tetracyclopentadiene, and 59.99% to 37.00% by weight dicyclopentadiene, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a process for preparing a substantially void-free article, comprising combining a resin composition and a catalyst composition to form a ROMP composition, wherein the catalyst composition comprises at least one metal carbene olefin metathesis catalyst and the resin composition comprises a cyclic olefin composition, wherein the cyclic olefin composition comprises 35.00% to 70.00% by weight tricyclopentadiene, 0.1% to 4.00% by weight tetracyclopentadiene, and 64.99% to 26.00% by weight dicyclopentadiene, and subjecting the ROMP composition to conditions effective to promote an olefin metathesis reaction (e.g. a ring opening metathesis polymerization reaction).

Another embodiment of the invention provides a process for preparing a substantially void-free article, comprising combining a resin composition and a catalyst composition to form a ROMP composition, wherein the catalyst composition comprises at least one metal carbene olefin metathesis catalyst and the resin composition comprises a cyclic olefin composition, wherein the cyclic olefin composition comprises 40.00% to 65.00% by weight tricyclopentadiene, 0.1% to 3.50% by weight tetracyclopentadiene, and 59.99% to 31.50% by weight dicyclopentadiene, and subjecting the ROMP composition to conditions effective to promote an olefin metathesis reaction (e.g. a ring opening metathesis polymerization reaction).

Another embodiment of the invention provides a process for preparing a substantially void-free article, comprising combining a resin composition and a catalyst composition to form a ROMP composition, wherein the catalyst composition comprises at least one metal carbene olefin metathesis catalyst and the resin composition comprises a cyclic olefin composition, wherein the cyclic olefin composition comprises 40.00% to 60.00% by weight tricyclopentadiene, 0.1% to 3.00% by weight tetracyclopentadiene, and 59.99% to 37.00% by weight dicyclopentadiene, and subjecting the ROMP composition to conditions effective to promote an olefin metathesis reaction (e.g. a ring opening metathesis polymerization reaction).

Another embodiment of the invention provides an article of manufacture, comprising a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and 64.99% to 26.00% by weight dicyclopentadiene.

Another embodiment of the invention provides an article of manufacture, comprising a resin composition and a catalyst composition comprising at least one metal carbene olefin metathesis catalyst, where the resin composition comprises a cyclic olefin composition, where the cyclic olefin composition comprises 40.00% to 65.00% by weight tricyclopentadiene, 0.01% to 3.50% by weight tetracyclopentadiene, and 59.99% to 31.50% by weight dicyclopentadiene.

Another embodiment of the invention provides an article of manufacture, comprising a resin composition and a catalyst composition comprising at least one metal carbene olefin metathesis catalyst, where the resin composition comprises a cyclic olefin composition, where the cyclic olefin composition comprises 40.00% to 60.00% by weight tricyclopentadiene, 0.01% to 3.00% by weight tetracyclopentadiene, and 59.99% to 37.00% by weight dicyclopentadiene.

Another embodiment of the invention provides an article of manufacture, the article of manufacture comprising a ROMP polymer, wherein the ROMP polymer is the reaction product of a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and 64.99% to 26.00% by weight dicyclopentadiene.

Another embodiment of the invention provides an article of manufacture, the article of manufacture comprising a ROMP polymer, wherein the ROMP polymer is the reaction product of a resin composition and a catalyst composition comprising at least one metal carbene olefin metathesis catalyst, where the resin composition comprises a cyclic olefin composition, where the cyclic olefin composition comprises 40.00% to 65.00% by weight tricyclopentadiene, 0.01% to 3.50% by weight tetracyclopentadiene, and 59.99% to 31.50% by weight dicyclopentadiene.

Another embodiment of the invention provides an article of manufacture, the article of manufacture comprising a ROMP polymer, wherein the ROMP polymer is the reaction product of a resin composition and a catalyst composition comprising at least one metal carbene olefin metathesis catalyst, where the resin composition comprises a cyclic olefin composition, where the cyclic olefin composition comprises 40.00% to 60.00% by weight tricyclopentadiene, 0.01% to 3.00% by weight tetracyclopentadiene, and 59.99% to 37.00% by weight dicyclopentadiene.

Another embodiment of the invention provides an article of manufacture, the article of manufacture comprising a ROMP polymer composite, wherein the ROMP polymer composite is the reaction product of a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and 64.99% to 26.00% by weight dicyclopentadiene.

Another embodiment of the invention provides an article of manufacture, the article of manufacture comprising a ROMP polymer composite, wherein the ROMP polymer composite is the reaction product of a resin composition and a catalyst composition comprising at least one metal carbene olefin metathesis catalyst, where the resin composition comprises a cyclic olefin composition, where the cyclic olefin composition comprises 40.00% to 65.00% by weight tricyclopentadiene, 0.01% to 3.50% by weight tetracyclopentadiene, and 59.99% to 31.50% by weight dicyclopentadiene.

Another embodiment of the invention provides an article of manufacture, the article of manufacture comprising a ROMP polymer composite, wherein the ROMP polymer composite is the reaction product of a resin composition and a catalyst composition comprising at least one metal carbene olefin metathesis catalyst, where the resin composition comprises a cyclic olefin composition, where the cyclic olefin composition comprises 40.00% to 60.00% by weight tricyclopentadiene, 0.01% to 3.00% by weight tetracyclopentadiene, and 59.99% to 37.00% by weight dicyclopentadiene.

Another embodiment of the invention provides a ROMP composition, comprising a catalyst composition comprising at least one metal carbene olefin metathesis catalyst; and a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene.

Another embodiment of the invention provides a ROMP composition, comprising a catalyst composition comprising at least one metal carbene olefin metathesis catalyst; and a resin composition comprising a cyclic olefin composition, wherein the cyclic olefin composition comprises 40.00 to 65.00 percent by weight tricyclopentadiene, 0.01 to 3.50 percent by weight tetracyclopentadiene, and 59.99 to 31.50 percent by weight dicyclopentadiene.

Another embodiment of the invention provides a ROMP composition, comprising a catalyst composition comprising at least one metal carbene olefin metathesis catalyst; and a resin composition comprising a cyclic olefin composition, wherein the cyclic olefin composition comprises 40.00 to 60.00 percent by weight tricyclopentadiene, 0.01 to 3.00 percent by weight tetracyclopentadiene, and 59.99 to 37.00 percent by weight dicyclopentadiene.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene; combining the catalyst composition and the resin composition to form a ROMP composition; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene; combining the catalyst composition and the resin composition to form a ROMP composition; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 40.00 to 65.00 percent by weight tricyclopentadiene, 0.01 to 3.50 percent by weight tetracyclopentadiene, and 59.99 to 31.50 percent by weight dicyclopentadiene; combining the catalyst composition and the resin composition to form a ROMP composition; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 40.00 to 65.00 percent by weight tricyclopentadiene, 0.01 to 3.50 percent by weight tetracyclopentadiene, and 59.99 to 31.50 percent by weight dicyclopentadiene; combining the catalyst composition and the resin composition to form a ROMP composition; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 40.00 to 60.00 percent by weight tricyclopentadiene, 0.01 to 3.00 percent by weight tetracyclopentadiene, and 59.99 to 37.00 percent by weight dicyclopentadiene; combining the catalyst composition and the resin composition to form a ROMP composition; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 40.00 to 60.00 percent by weight tricyclopentadiene, 0.01 to 3.00 percent by weight tetracyclopentadiene, and 59.99 to 37.00 percent by weight dicyclopentadiene; combining the catalyst composition and the resin composition to form a ROMP composition; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene; combining the catalyst composition and the resin composition to form a ROMP composition; contacting the ROMP composition with a substrate material; and subjecting the ROMP composition to conditions effective to promote an olefin metathesis reaction.

Another embodiment of the invention provides a method for making a ROMP polymer composite, comprising providing a catalyst composition comprising at least one metal carbene olefin metathesis catalyst; providing a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene; combining the catalyst composition and the resin composition to form a ROMP composition; contacting the ROMP composition with a substrate material; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 40.00 to 65.00 percent by weight tricyclopentadiene, 0.01 to 3.50 percent by weight tetracyclopentadiene, and 59.99 to 31.50 percent by weight dicyclopentadiene; combining the catalyst composition and the resin composition to form a ROMP composition; contacting the ROMP composition with a substrate material; and subjecting the ROMP composition to conditions effective to promote an olefin metathesis reaction.

Another embodiment of the invention provides a method for making a ROMP polymer composite, comprising providing a catalyst composition comprising at least one metal carbene olefin metathesis catalyst; providing a resin composition comprising a cyclic olefin composition, wherein the cyclic olefin composition comprises 40.00 to 65.00 percent by weight tricyclopentadiene, 0.01 to 3.50 percent by weight tetracyclopentadiene, and 59.99 to 31.50 percent by weight dicyclopentadiene; combining the catalyst composition and the resin composition to form a ROMP composition; contacting the ROMP composition with a substrate material; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 40.00 to 60.00 percent by weight tricyclopentadiene, 0.01 to 3.00 percent by weight tetracyclopentadiene, and 59.99 to 37.00 percent by weight dicyclopentadiene; combining the catalyst composition and the resin composition to form a ROMP composition; contacting the ROMP composition with a substrate material; and subjecting the ROMP composition to conditions effective to promote an olefin metathesis reaction.

Another embodiment of the invention provides a method for making a ROMP polymer composite, comprising providing a catalyst composition comprising at least one metal carbene olefin metathesis catalyst; providing a resin composition comprising a cyclic olefin composition, wherein the cyclic olefin composition comprises 40.00 to 60.00 percent by weight tricyclopentadiene, 0.01 to 3.00 percent by weight tetracyclopentadiene, and 59.99 to 37.00 percent by weight dicyclopentadiene; combining the catalyst composition and the resin composition to form a ROMP composition; contacting the ROMP composition with a substrate material; and subjecting the ROMP composition to conditions effective to promote polymerization of the ROMP composition.

Another embodiment of the invention provides a cyclic olefin composition comprising 35.00% to 70.00% by weight tricyclopentadiene, 0.01% to 4.00% by weight tetracyclopentadiene, and up to 64.99% by weight of one or more other cyclic olefins.

Another embodiment of the invention provides a cyclic olefin composition comprising 35.00% to 70.00% by weight tricyclopentadiene, 0.01% to 4.00% by weight tetracyclopentadiene, and up to 64.99% by weight of one or more other cyclic olefins, wherein the other cyclic olefins have a melting point below 35° C.

Another embodiment of the invention provides a cyclic olefin composition comprising 35.00 to 70.00 weight percent tricyclopentadiene, 0.01 to 4.00 weight percent tetracyclopentadiene, and up to 64.99 weight percent of one or more other cyclic olefins, where the weight percent is determined by gas chromatography.

Another embodiment of the invention provides a cyclic olefin composition comprising 35.00% to 70.00% by weight tricyclopentadiene, 0.01% to 4.00% by weight tetracyclopentadiene, and up to 64.99% by weight of one or more other cyclic olefins, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins.

Another embodiment of the invention provides a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a ROMP composition, comprising a catalyst composition comprising at least one metal carbene olefin metathesis catalyst; and a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins; combining the catalyst composition and the resin composition to form a ROMP composition; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins; combining the catalyst composition and the resin composition to form a ROMP composition; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins; combining the catalyst composition and the resin composition to form a ROMP composition; contacting the ROMP composition with a substrate material; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins; combining the catalyst composition and the resin composition to form a ROMP composition; contacting the ROMP composition with a substrate material; and subjecting the ROMP composition to conditions effective to promote polymerization of the ROMP composition.

Another embodiment of the invention provides a process for preparing a substantially void-free article, comprising combining a resin composition and a catalyst composition to form a ROMP composition, wherein the catalyst composition comprises at least one metal carbene olefin metathesis catalyst and the resin composition comprises a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins, and subjecting the ROMP composition to conditions effective to promote an olefin metathesis reaction (e.g. a ring opening metathesis polymerization reaction).

Another embodiment of the invention provides an article of manufacture, comprising a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and up to 64.99% by weight of one or more other cyclic olefins.

Another embodiment of the invention provides an article of manufacture, the article of manufacture comprising a ROMP polymer, wherein the ROMP polymer is the reaction product of a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and up to 64.99% by weight of one or more other cyclic olefins.

Another embodiment of the invention provides an article of manufacture, the article of manufacture comprising a ROMP polymer composite, wherein the ROMP polymer composite is the reaction product of a resin composition and a catalyst composition comprising at least one metal carbene olefin metathesis catalyst, where the resin composition comprises a cyclic olefin composition, where the cyclic olefin composition comprises 35.00% to 70.00% by weight tricyclopentadiene, 0.01% to 4.00% by weight tetracyclopentadiene, and up to 64.99% by weight of one or more other cyclic olefins.

Another embodiment of the invention provides a cyclic olefin composition, where the cyclic olefin composition comprises 35 to 70 percent by weight tricyclopentadiene and less than 4 percent by weight tetracyclopentadiene.

Another embodiment of the invention provides a cyclic olefin composition, where the cyclic olefin composition comprises 35 to 70 percent by weight tricyclopentadiene and less than 3.5 percent by weight tetracyclopentadiene.

Another embodiment of the invention provides a cyclic olefin composition, where the cyclic olefin composition comprises 35 to 70 percent by weight tricyclopentadiene and less than 3 percent by weight tetracyclopentadiene.

Another embodiment of the invention provides a cyclic olefin composition comprising 55% to 58% by weight tricyclopentadiene, 0% to 3.6% by weight tetracyclopentadiene, and 38% to 42% by weight dicyclopentadiene.

Another embodiment of the invention provides a cyclic olefin composition comprising 55% to 58% by weight tricyclopentadiene, 0% to 3.6% by weight tetracyclopentadiene, and 38% to 42% by weight dicyclopentadiene, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

Another embodiment of the invention provides a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene.

Another embodiment of the invention provides a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10°.

Another embodiment of the invention provides a process for preparing a substantially void-free article, comprising combining a resin composition and a catalyst composition to form a ROMP composition, wherein the catalyst composition comprises at least one metal carbene olefin metathesis catalyst and the resin composition comprises a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene, and subjecting the ROMP composition to conditions effective to promote an olefin metathesis reaction (e.g. a ring opening metathesis polymerization reaction).

Another embodiment of the invention provides an article of manufacture, comprising a resin composition and a catalyst composition comprising at least one metal carbene olefin metathesis catalyst, where the resin composition comprises a cyclic olefin composition, where the cyclic olefin composition comprises 55% to 58% by weight tricyclopentadiene, 0% to 3.6% by weight tetracyclopentadiene, and 38% to 42% by weight dicyclopentadiene.

Another embodiment of the invention provides an article of manufacture, the article of manufacture comprising a ROMP polymer, wherein the ROMP polymer is the reaction product of a resin composition and a catalyst composition comprising at least one metal carbene olefin metathesis catalyst, where the resin composition comprises a cyclic olefin composition, where the cyclic olefin composition comprises 55% to 58% by weight tricyclopentadiene, 0% to 3.6% by weight tetracyclopentadiene, and 38% to 42% by weight dicyclopentadiene.

Another embodiment of the invention provides an article of manufacture, the article of manufacture comprising a ROMP polymer composite, wherein the ROMP polymer composite is the reaction product of a resin composition and a catalyst composition comprising at least one metal carbene olefin metathesis catalyst, where the resin composition comprises a cyclic olefin composition, where the cyclic olefin composition comprises 55% to 58% by weight tricyclopentadiene, 0% to 3.6% by weight tetracyclopentadiene, and 38% to 42% by weight dicyclopentadiene.

Another embodiment of the invention provides a ROMP composition, comprising a catalyst composition comprising at least one metal carbene olefin metathesis catalyst; and a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene; combining the catalyst composition and the resin composition to form a ROMP composition; and subjecting the ROMP composition to conditions effective to promote an olefin metathesis reaction.

Another embodiment of the invention provides a method for making a ROMP polymer, comprising providing a catalyst composition comprising at least one metal carbene olefin metathesis catalyst; providing a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene; combining the catalyst composition and the resin composition to form a ROMP composition; and subjecting the ROMP composition to conditions effective to promote polymerization of the ROMP composition.

Another embodiment of the invention provides a method, comprising providing a catalyst composition comprising at least one metal carbene olefin metathesis catalyst; providing a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene; combining the catalyst composition and the resin composition to form a ROMP composition; contacting the ROMP composition with at least one substrate material; and subjecting the ROMP composition to conditions effective to promote an olefin metathesis reaction.

Another embodiment of the invention provides a method for making a ROMP polymer composite, comprising providing a catalyst composition comprising at least one metal carbene olefin metathesis catalyst; providing a resin composition comprising a cyclic olefin composition, wherein the cyclic olefin composition comprises 55% to 58% by weight tricyclopentadiene, 0% to 3.6% by weight tetracyclopentadiene, and 38% to 42% by weight dicyclopentadiene; combining the catalyst composition and the resin composition to form a ROMP composition; contacting the ROMP composition with at least one substrate material; and subjecting the ROMP composition to conditions effective to promote polymerization of the ROMP composition.

In another embodiment, the invention provides a ROMP composition, comprising a catalyst composition comprising at least one metal carbene olefin metathesis catalyst and a resin composition comprising a cyclic olefin composition, wherein the cyclic olefin composition comprises 35.00% to 70.00% by weight tricyclopentadiene, 0.01% to 4.00 by weight tetracyclopentadiene, and up to 64.99% by weight of one or more other olefins, where the ROMP composition or the resin composition is 39.9° C. to 20° C., 39.9° C. to 25° C., 39.9° C. to 30° C., 35° C. to 20° C., or 35° C. to 25° C., and the ROMP composition may be added to a mold preheated to 60° C. to 200° C., 60° C. to 150° C., 60° C. to 120° C., 60° C. to 100° C., 60° C. to 90° C., or 60° C. to 80° C., and/or the mold may be rapidly heated (e.g., at a rate greater than 0.5° C./min) to prepare molded polymer articles and/or polymer composite articles, where the resultant molded polymer articles and/or polymer composite articles are free or substantially free of defects.

In another embodiment, the invention provides a ROMP composition, comprising a catalyst composition comprising at least one metal carbene olefin metathesis catalyst and a resin composition comprising a cyclic olefin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene, where the ROMP composition or the resin composition is 39.9° C. to 20° C., 39.9° C. to 25° C., 39.9° C. to 30° C., 35° C. to 20° C., or 35° C. to 25° C., and the ROMP composition may be added to a mold preheated to 60° C. to 200° C., 60° C. to 150° C., 60° C. to 120° C., 60° C. to 100° C., 60° C. to 90° C., or 60° C. to 80° C., and/or the mold may be rapidly heated (e.g., at a rate greater than 0.5° C./min) to prepare molded polymer articles and/or polymer composite articles, where the resultant molded polymer articles and/or polymer composite articles are free or substantially free of defects.

In another embodiment, the invention provides for use of a cyclic olefin composition comprising 35.00% to 70.00% by weight tricyclopentadiene, 0.01% to 4.00 by weight tetracyclopentadiene, and up to 64.99% by weight of one or more other olefins to prepare a resin composition.

In another embodiment, the invention provides for use of a cyclic olefin composition comprising 35.00 to 70.00 percent by weight tricyclopentadiene, 0.01 to 4.00 percent by weight tetracyclopentadiene, and 64.99 to 26.00 percent by weight dicyclopentadiene to prepare a resin composition.

In another embodiment, the invention provides for use of a cyclic olefin composition to prepare a resin composition, wherein the cyclic olefin composition comprises 35.00% to 70.00% by weight tricyclopentadiene, 0.01% to 4.00 by weight tetracyclopentadiene, and up to 64.99% by weight of one or more other olefins, where the cyclic olefin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

In another embodiment, the invention provides for use of a cyclic olefin composition to prepare a resin composition, wherein the cyclic olefin composition comprises 35.00 to 70.00 percent by weight tricyclopentadiene, 0.01 to 4.00 percent by weight tetracyclopentadiene, and 64.99 to 26.00 percent by weight dicyclopentadiene, where the resin composition is a stable homogenous liquid at 39° C. to 10° C., at 39° C. to 15° C., 39° C. to 20° C., at 39° C. to 25° C., at 39° C. to 30° C., at 39° C. to 35° C., at 30° C. to 15° C., at 35° C. to 20° C., at 35° C. to 25° C., at 25° C. to 20° C., or at 25° C. to 10° C.

In another embodiment the invention provides for use of a cyclic olefin composition for preparing a polymer article that is free or substantially free of defects, wherein the polymer article is formed by a polymerization reaction of a ROMP composition, the ROMP composition comprising a resin composition and a catalyst composition comprising at least one metal carbene olefin metathesis catalyst, the resin composition comprising a cyclic olefin composition comprising 35.00% to 70.00% by weight tricyclopentadiene, 0.01% to 4.00 by weight tetracyclopentadiene, and up to 64.99% by weight of one or more other olefins.

In another embodiment of the invention provides for use of a cyclic olefin composition for preparing a polymer article, wherein the polymer article is formed by a polymerization reaction of a ROMP composition, the ROMP composition comprising a resin composition and a catalyst composition comprising at least one metal carbene olefin metathesis catalyst, the resin composition comprising a cyclic olefin composition comprising 35.00% to 70.00% by weight tricyclopentadiene, 0.01% to 4.00 by weight tetracyclopentadiene, and up to 64.99% by weight of one or more other olefins.

In another embodiment the invention provides for use of a cyclic olefin composition for preparing a polymer composite article that is free or substantially free of defects, wherein the polymer composite article is formed by a polymerization reaction of a ROMP composition in contact with a substrate material, the ROMP composition comprising a resin composition and a catalyst composition comprising at least one metal carbene olefin metathesis catalyst, the resin composition comprising a cyclic olefin composition comprising 35.00% to 70.00% by weight tricyclopentadiene, 0.01% to 4.00 by weight tetracyclopentadiene, and up to 64.99% by weight of one or more other olefins.

In another embodiment the invention provides for use of a cyclic olefin composition for preparing a polymer composite article, wherein the polymer composite article is formed by a polymerization reaction of a ROMP composition in contact with a substrate material, the ROMP composition comprising a resin composition and a catalyst composition comprising at least one metal carbene olefin metathesis catalyst, the resin composition comprising a cyclic olefin composition comprising 35.00% to 70.00% by weight tricyclopentadiene, 0.01% to 4.00 by weight tetracyclopentadiene, and up to 64.99% by weight of one or more other olefins.

In another embodiment the invention provides for use of a cyclic olefin composition for preparing a polymer article that is free or substantially free of defects, wherein the polymer article is formed by a polymerization reaction of a ROMP composition, the ROMP composition comprising a resin composition and a catalyst composition comprising at least one metal carbene olefin metathesis catalyst, the resin composition comprising a cyclic olefin composition comprising 35.00 to 70.00 percent by weight tricyclopentadiene, 0.01 to 4.00 percent by weight tetracyclopentadiene, and 64.99 to 26.00 percent by weight dicyclopentadiene.

In another embodiment the invention provides for use of a cyclic olefin composition for preparing a polymer article, wherein the polymer article is formed by a polymerization reaction of a ROMP composition, the ROMP composition comprising a resin composition and a catalyst composition comprising at least one metal carbene olefin metathesis catalyst, the resin composition comprising a cyclic olefin composition comprising 35.00 to 70.00 percent by weight tricyclopentadiene, 0.01 to 4.00 percent by weight tetracyclopentadiene, and 64.99 to 26.00 percent by weight dicyclopentadiene.

In another embodiment the invention provides for use of a cyclic olefin composition for preparing a polymer composite article that is free or substantially free of defects, wherein the polymer composite article is formed by a polymerization reaction of a ROMP composition in contact with a substrate material, the ROMP composition comprising a resin composition and a catalyst composition comprising at least one metal carbene olefin metathesis catalyst, the resin composition comprising a cyclic olefin composition comprising 35.00 to 70.00 percent by weight tricyclopentadiene, 0.01 to 4.00 percent by weight tetracyclopentadiene, and 64.99 to 26.00 percent by weight dicyclopentadiene.

In another embodiment the invention provides for use of a cyclic olefin composition for preparing a polymer composite article, wherein the polymer composite article is formed by a polymerization reaction of a ROMP composition in contact with a substrate material, the ROMP composition comprising a resin composition and a catalyst composition comprising at least one metal carbene olefin metathesis catalyst, the resin composition comprising a cyclic olefin composition comprising 35.00 to 70.00 percent by weight tricyclopentadiene, 0.01 to 4.00 percent by weight tetracyclopentadiene, and 64.99 to 26.00 percent by weight dicyclopentadiene.

Embodiments herein are not meant to be construed in a limiting sense. Various modifications in form and detail of the embodiments of the invention, as well as other aspects and variations of the invention will be apparent to the skilled artisan in light of the following detailed description and examples.

DETAILED DESCRIPTION

Terminology and Definitions

Unless otherwise indicated, the invention is not limited to specific reactants, substituents, catalysts, cyclic olefins, resin compositions, cyclic olefin compositions, catalyst compositions, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, —O(CO)-alkynyl wherein "alkyl," "aryl," "aralkyl", alkaryl, alkenyl, and alkynyl are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, alkynyl groups, aryl groups, and the like. The term "lower hydrocarbyl" intends a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated, and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and heteroatom-containing hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus, or silicon, typically nitrogen, oxygen, or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "substrate material" as used herein, is intended to generally mean any material that the resin compositions of the invention may be contacted with, applied to, or have the substrate material incorporated in to the resin. Without limitation, such materials include reinforcing materials, such as filaments, fibers, rovings, mats, weaves, fabrics, knitted material, cloth or other known structures, glass fibers and fabrics, carbon fibers and fabrics, aramid fibers and fabrics, and polyolefin or other polymer fibers or fabrics. Other suitable substrate materials include metallic density modulators, microparticulate density modulators, such as microspheres, glass microspheres, ceramic microspheres, microballons, cenospheres, and macroparticulate density modulators, such as glass or ceramic beads. A ROMP polymer composite may be comprised of one substrate material or a mixture of different substrate materials.

The expressions "substantially free of defects" and "substantially defect free" means that there is less than one visible defect per square inch of polymer, as seen with the naked eye. A defect includes, for example, unwanted pores, cavities, bubbles, voids, knit lines and/or internal stress fractures. In particular, the present invention mitigates against issues related to defects that are thought to be caused by volatilization of low boiling compounds present in the cyclic olefin compositions or generated during polymerization (exotherm) cycle as discussed herein. A defect related to volatilization may be visually present on the surface of the ROMP polymer article and/or ROMP polymer composite article. A defect related to volatilization may also be visually present on the interior of the ROMP polymer article and/or ROMP polymer composite article when the article is cut into sections. Other examples of defects which may also be present may be related to poor mixing such as entrapped air bubbles and/or surface defects related to imperfect mold surfaces.

As is known in the art, weight percent (wt %) can be represented by gas chromatography (GC) percent area (area %). Hence, GC area % obtained from the GC was reported as wt %. Weight percent (wt %) and percent by weight are used interchangeably herein.

Adhesion Promoter

Adhesion promoters that may be used in the present invention disclosed herein are generally compounds containing at least two isocyanate groups (such as, for example, methylene diphenyl diisocyanate and hexamethylene diisocyanate). The adhesion promoter may be a diisocyanate, triisocyanate, or polyisocyanate (i.e., containing four or more isocyanate groups). The adhesion promoter may be a mixture of at least one diisocyanate, triisocyanate, or polyisocyanate. In a more particular aspect of the invention, the adhesion promoter comprises, or is limited to, a diisocyanate compound, or mixtures of diisocyanate compounds. Such adhesion promoters and their use are described in PCT International Publication Number WO 2012/174502.

In general, adhesion promoters that may be used in the present invention may be any compound having at least two isocyanate groups. Suitable adhesion promoters include, without limitation, isocyanate compounds comprising at least two isocyanate groups, and wherein the compounds are selected from hydrocarbyl, substituted hydrocarbyl, heteroatom-containing hydrocarbyl, substituted heteroatom-containing hydrocarbyl, and functionalized hydrocarbyl compounds. As described above, suitable hydrocarbyl adhesion promoter compounds generally include alkyl, cycloalkyl, alkylene, alkenyl, alkynyl, aryl, cycloalkyl, alkaryl, and aralkyl compounds. Substituted heteroatom-containing, and functionalized hydrocarbyl adhesion promoter compounds include the afore-mentioned hydrocarbyl compounds, as well as the variations thereof noted hereinabove.

Adhesion promoters that may be used in the present invention may be an alkyl diisocyanate. An alkyl diisocyanate refers to a linear, branched, or cyclic saturated or unsaturated hydrocarbon group typically although not necessarily containing 1 to about 24 carbon atoms, preferably a diisocyanate containing 2 to about 12 carbon atoms, and more preferably a diisocyanate containing 6 to 12 carbon atoms such as hexamethylene diisocyanate (HDI), octamethylene diisocyanate, decamethylene diisocyanate, and the like. Cycloalkyl diisocyanates contain cyclic alkyl group, typically having 4 to 16 carbon atoms. A preferred cycloalkyl diisocyanate containing 6 to about 12 carbon atoms are cyclohexyl, cyclooctyl, cyclodecyl, and the like. A more preferred cycloalkyl diisocyanate originates as a condensation product of acetone called 5-isocyanato-1-(isocyanatomethyl)-1,3,3-trimethyl-cyclohexane, commonly known as Isophorone diisocyanate (IPDI) and the isomers of isocyanato-[(isocyanatocyclohexyl)methyl]cyclohexane ($H_{12}$MDI). $H_{12}$MDI is derived from the hydrogenated form of the aryl diisocyanate methylene diphenyl diisocyanate (MDI).

Adhesion promoters that may be used in the present invention may be an aryl diisocyanate. Aryl diisocyanates refers to aromatic diisocyanates containing a single aromatic ring or multiple aromatic rings that are fused together, directly linked, or indirectly linked (such that the different aromatic rings are bound to a common group such as a methylene or ethylene moiety). Preferred aryl diisocyanates contain 5 to 24 carbon atoms, and particularly preferred aryl diisocyanates contain 5 to 14 carbon atoms. Exemplary aryl diisocyanates contain one aromatic ring or two fused or linked aromatic rings, e.g., phenyl, tolyl, xylyl, naphthyl, biphenyl, diphenylether, benzophenone, and the like. Preferred aromatic diisocyanates include toluene diisocyanates, tetramethylxylene diisocyanate (TMXDI), and methylene diphenyl diisocyanate (MDI), which may comprise any mixture of its three isomers, 2.2'-MDI, 2,4'-MDI, and 4,4'-MDI.

Adhesion promoters that may be used in the present invention may be a polymer-containing isocyanate, such as, for example, diisocyanates. Polymer-containing isocyanates refers to a polymer-containing two or more terminal and/or pendant alkyl or aryl isocyanate groups. The polymer-containing isocyanates generally have to have a minimal solubility in the resin to provide improved mechanical properties. Preferred polymer-containing isocyanates include, but are not limited to, PM200 (poly MDI), Lupranate® (poly MDI from BASF), Krasol® isocyanate terminated polybutadiene prepolymers, such as, for example, Krasol® LBD2000 (TDI based), Krasol® LBD3000 (TDI based), Krasol® NN-22 (MDI based), Krasol® NN-23 (MDI based), Krasol® NN-25 (MDI based), and the like. Krasol® isocyanate terminated polybutadiene prepolymers are available from Cray Valley.

Adhesion promoters that may be used in the present invention may be a trimer of alkyl diisocyanates and aryl diisocyanates. In its simplest form, any combination of polyisocyanate compounds may be trimerized to form an isocyanurate ring containing isocyanate functional groups. Trimers of alkyl diisocyanate and aryl diisocyanates may also be referred to as isocyanurates of alkyl diisocyanate or aryl diisocyanate. Preferred alkyl diisocyanate and aryl diisocyanate trimers include, but are not limited to, hexamethylene diisocyanate trimer (HDIt), isophorone diisocyanate trimer, toluene diisocyanate trimer, tetramethylxylene diisocyanate trimer, methylene diphenyl diisocyanate trimers, and the like. More preferred adhesion promoters are toluene diisocyanates, tetramethylxylene diisocyanate (TMXDI), and methylene diphenyl diisocyanate (MDI) including any mixture of its three isomers 2.2'-MDI, 2,4'-MDI and 4,4'-MDI; liquid MDI; solid MDI; hexamethylenediisocyanatetrimer (HDIt); hexamethylenediisocyanate (HDI); isophorone diisocyanate (IPDI); 4,4'-methylene bis (cyclohexyl isocyanate) (H12MDI); polymeric MDI (PM200); MDI prepolymer (Lupranate® 5080); liquid carbodiimide modified 4,4'-MDI (Lupranate® MM103); liquid MDI (Lupranate® MI); liquid MDI (Mondur® ML); and liquid MDI (Mondur® MLQ). Even more preferred adhesion promoters are methylene diphenyl diisocyanate (MDI) including any mixture of its three isomers 2,2'-MDI, 2,4'-MDI and 4,4'-MDI; liquid MDI; solid MDI; hexamethylenediisocyanatetrimer (HDIt); hexamethylene diisocyanate (HDI); isophorone diisocyanate (IPDI); 4,4'-methylene bis (cyclohexyl isocyanate) (H12MDI); polymeric MDI (PM200); MDI prepolymer (Lupranate® 5080); liquid carbodiimide modified 4,4'-MDI (Lupranate® MM103); liquid MDI) (Lupranate® MI); liquid MDI (Mondur® ML); liquid MDI (Mondur® MLQ).

Any concentration of adhesion promoter which improves the mechanical properties of the olefin composite (e.g., ROMP polymer composite) is sufficient for the invention. In general, suitable amounts of adhesion promoter range from 0.001-50 phr, particularly 0.05-10 phr, more particularly 0.1-10 phr, or even more particularly 0.5-4.0 phr. One or more adhesion promoters may be used in the present invention.

Additional adhesion promoters suitable for use in the present invention comprise functionalized silanes of the formula Fn-(A)$_n$-Si(Y*)$_3$, wherein Y* is selected from halide (preferably chloride) or OR; Fn is a functional group selected from acrylate, methacrylate, allyl, vinyl, alkene, cycloalkene, or norbornene; A is a divalent linking group selected from hydrocarbylene, substituted hydrocarbylene, heteroatom-containing hydrocarbylene, or substituted heteroatom-containing hydrocarbylene; n is 0 or 1; and R is selected from hydrocarbyl, substituted hydrocarbyl, heteroatom-containing hydrocarbyl, or substituted heteroatom-containing hydrocarbyl, preferably lower alkyl, more preferably methyl, ethyl, or isopropyl; and a peroxide selected from dialkyl and diaryl peroxides.

Additional adhesion promoters for use in the present invention and methods for their use include those disclosed in International Pat. App. No. PCT/US00/03002, the contents of which are incorporated herein by reference.

Compounds Comprising a Heteroatom-Containing Functional Group and a Metathesis Active Olefin The compound comprising a heteroatom-containing functional group and a metathesis active olefin typically contains between 2 and 20 carbons with hydroxyl, amine, thiol, phosphourus, or silane functional groups. Compounds comprising a heteroatom-containing functional group and a metathesis active olefin that may be used in the present invention disclosed herein are generally compounds containing at least one heteroatom containing functional group and at least one metathesis active olefin and are of the following general structure:

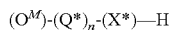

wherein $O^M$, Q*, and X* are as follows:

$O^M$ is a metathesis active olefin fragment selected from cyclic olefins and acyclic olefins, where the carbon-carbon double bond typically is not tetra-substituted (e.g., at least one substituent is a hydrogen);

Q* is an optional linker group (e.g., n=0 or 1) such as, for example, a hydrocarbylene (including, for example, substituted hydrocarbylene, heteroatom-containing hydrocarbylene, and substituted heteroatom-containing hydrocarbylene, such as substituted and/or heteroatom-containing alkylene) or —(CO)— group; and X* is oxygen, sulfur, or a heteroatom-containing fragment such as $N(R^X)$, $P(R^X)$, $OP(R^X)$, $OP(R^X)O$, $OP(OR^X)O$, $P(=O)(R^X)$, $OP(=O)(R^X)$, $OP(=O)(R^X)O$, $OP(=O)(OR^X)O$, $Si(R^X)_2$, $Si(R^X)_2O$, $Si(OR^X)_2O$, or $Si(R^X)(OR^X)O$, wherein each $R^X$ is, independent of one another, a hydrogen or a hydrocarbyl group optionally comprising further functional groups. Each $R^X$ is, independent of one another, most commonly a hydrogen, aryl, or lower alkyl group.

Metathesis active olefins include cyclic olefins as described herein, where such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a ROMP cyclic olefin composition. Metathesis active olefins also include acyclic olefins, where such acyclic olefins may be optionally substituted, optionally heteroatom-containing, mono-unsaturated, di-unsaturated, or poly-unsaturated $C_2$ to $C_{30}$ hydrocarbons, typically $C_2$ to $C_{20}$ hydrocarbons, or more typically $C_2$ to $C_{12}$ hydrocarbons. Acyclic olefins may contain one or more terminal olefins and/or one or more internal olefins, and/or any combination of terminal olefins and/or internal olefins.

In the heteroatom-containing functional group, X* is commonly oxygen, sulfur, or $NR^X$ and is most commonly oxygen, i.e., a hydroxy-substituted olefin. Preferred compounds comprising a heteroatom-containing functional group and a metathesis active olefin include, but are not limited to, 5-norbornene-2-methanol (NB-MeOH); 2-hydroxyethyl bicycle[2.2.1]hept-2-ene-carboxylate (HENB); 2-hydroxyethyl acrylate (HEA); allyl alcohol; oleyl alcohol; 9-decen-1-ol; vinyl alcohol, allyl alcohol, cis-13-dodecenol, and trans-9-octadecenol, and other unsaturated alcohols, norbornyl alcohol, 2-cycloocten-1-ol, 2-cyclooctadiene-1-ol, and p-vinyl phenol, and other alcohols which have an alicyclic structure; 2-hydroxyethyl methacrylate; 2-hydroxy-3-acryloxypropyl methacrylate, ethoxylated hydroxyethyl acrylate, ethoxylated hydroxyethyl methacrylate, polypropyleneglycol monomethacrylate, polypropylene glycol monoacrylate, phenol acrylate, phenol methacrylate, bisphenol A type epoxy acrylate, novolac type epoxy acrylate, and brominated bisphenol A type epoxy acrylate, and other methacrylics or acrylics which have one or more methacryl or acryl groups and hydroxyl groups, etc.

The compound comprising a heteroatom-containing functional group and a metathesis active olefin is combined with a compound containing at least two isocyanate groups and pre-reacted providing an adhesion promoter composition having in-resin storage stability and providing an olefin metathesis composite with improved mechanical properties. Any concentration of a compound comprising a heteroatom-containing functional group and a metathesis active olefin is sufficient for use in preparing adhesion promoter compositions of the invention, where the mol % or mol equivalents of a compound comprising a heteroatom-containing functional group and a metathesis active olefin used to form the pre-reacted mixture is less than the mol % or mol equivalents of a compound containing at least two isocyanate groups used to form the pre-reacted mixture. Mol ratios of a compound comprising a heteroatom-containing functional group and a metathesis active olefin relative to a compound containing at least two isocyanate groups range from 0.001:1 to 0.90:1. Preferred mol ratios of a compound comprising a heteroatom-containing functional group and a metathesis active olefin relative to a compound containing at least two isocyanate groups range from 0.01:1 to 0.75:1, particularly 0.01:1 to 0.5:1, more particularly 0.02:1 to 0.25:1. One skilled in the art will recognize that the optimal ratio of a compound comprising a heteroatom-containing functional group and a metathesis active olefin to a compound containing at least two isocyanate groups may need to be adjusted as a function of the amount of adhesion promoter composition added to the resin composition.

In another embodiment, a compound comprising a heteroatom-containing functional group and a metathesis active olefin may be combined with a resin composition comprising a cyclic olefin composition providing an olefin metathesis composite with improved mechanical properties. A compound comprising a heteroatom-containing functional group and a metathesis active olefin may be combined with a resin composition comprising a cyclic olefin composition and an adhesion promoter providing an olefin metathesis composite with improved mechanical properties. Any concentration of a compound comprising a heteroatom-containing functional group and a metathesis active olefin which improves the mechanical properties of the olefin composite is sufficient for the invention. In general, suitable amounts of a compound comprising a heteroatom-containing functional group and a metathesis active olefin range from 0.001-50 phr, particularly 0.05-10 phr, more particularly 0.1-10 phr, or even more particularly 0.5-4.0 phr. One or more compounds comprising a heteroatom-containing functional group and a metathesis active olefin may be used in the present invention.

Adhesion Promoter Compositions

Adhesion promoter compositions that may be used in the present invention disclosed herein are generally compositions comprising at least one adhesion promoter, discussed supra (i.e., at least one compound containing at least two isocyanate groups (e.g., methylene diphenyl diisocyanate, hexamethylene diisocyanate)) and at least one compound comprising a heteroatom-containing functional group and a metathesis active olefin, discussed supra (e.g., 2-hydroxyethyl bicyclo[2.2.1]hept-2-ene-5-carboxylate (HENB), 2-hydroxyethyl acrylate (HEA), oleyl alcohol, 9-decen-1-ol), where the compounds may be combined in various ratios to form a pre-reacted mixture, wherein the pre-reacted mixture is then subsequently added to a resin composition, and where the adhesion promoter composition possesses in-resin storage stability.

Compounds containing at least two isocyanate groups and compounds comprising a heteroatom-containing functional group and a metathesis active olefin useful for preparing adhesion promoter compositions of the invention are disclosed herein.

Preferred adhesion promoter compositions include, but are not limited to, pre-reacted mixtures of liquid MDI (Mondur® MLQ) and 2-hydroxyethyl bicycle[2.2.1]hept-2-ene-carboxylate (HENB); pre-reacted mixtures of liquid MDI (Mondur® MLQ) and 2-hydroxyethyl acrylate (HEA); pre-reacted mixtures of liquid MDI (Mondur® MLQ) and oleyl alcohol; and pre-reacted mixtures of liquid MDI (Mondur® MLQ) and 9-decen-1-ol.

Any concentration of adhesion promoter composition which improves the mechanical properties of the olefin composite is sufficient for the invention. In general, suitable amounts of adhesion promoter composition range from 0.001-50 phr, particularly 0.05-10 phr, more particularly 0.1-10 phr, or even more particularly, 0.5-4.0 phr.

Substrate Surfaces

The present invention is generally suitable for use with any substrate material in which the addition of an adhesion promoter or adhesion promoter composition provides beneficial improvements in the adhesion of a resin (e.g., ROMP) composition to the substrate material as compared to a resin composition that is the same with the exception that the adhesion promoter or adhesion promoter composition is not included. Furthermore, the present invention is generally suitable for use with any substrate material in which the addition of an adhesion promoter or adhesion promoter composition provides beneficial improvements in the adhesion of a polymer-matrix (e.g., ROMP polymer-matrix) to a substrate material compared to a polymer-matrix that is the same with the exception that the adhesion promoter or adhesion promoter composition is not included. The present invention is particularly beneficial for use with glass and carbon material surfaces suitable for use with epoxy and methacrylate resins, including those containing finishes or sizings, in which case the finishes or sizings do not need to be removed (e.g., by washing or heat cleaning) for the adhesion promoter or adhesion promoter composition to be effective. The present invention is also suitable for use with wood and aluminum materials. Suitable substrate materials may also be selected from fibrous, woven, microparticulate, ceramic, metal, polymer, and semiconductor materials. A polymer-matrix composite (e.g., ROMP polymer matrix composite) may be comprised of one substrate material or a mixture of different substrate materials.

Cyclic Olefins

Resin compositions and/or cyclic olefin compositions that may be used with the present invention disclosed herein comprise one or more cyclic olefins. In general, any cyclic olefin suitable for the metathesis reactions disclosed herein may be used. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a cyclic olefin composition or as part of a resin composition. While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of formula (A)

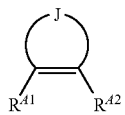

(A)

wherein J, $R^{A1}$, and $R^{A2}$ are as follows:

$R^{A1}$ and $R^{A2}$ is selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{A1}$ and $R^{A2}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage Z*, such that $R^{A1}$ and/or $R^{A2}$ then has the structure —$(Z^*)_n$-Fn wherein n is 1, Fn is the functional group, and Z* is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —$(Z^*)_n$-Fn groups, wherein n is zero or 1, and Fn and Z* are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by structure (A) may be represented by the structure (B)

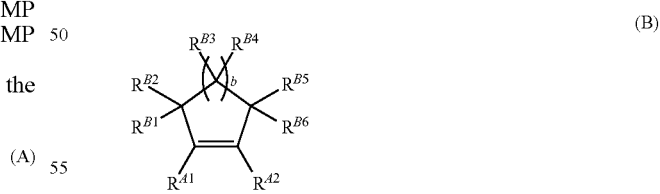

(B)

wherein b is an integer generally although not necessarily in the range of 1 to 10, typically 1 to 5, $R^{A1}$ and $R^{A2}$ are as defined above for structure (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, Z* and Fn are as defined previously, and wherein if any of the $R^{B1}$ through $R^{B6}$ moieties is substituted hydrocarbyl or substituted heteroatom-containing hydrocarbyl, the substituents may include one or more —(Z*)$_n$-Fn groups. Accordingly, R$^{B1}$, R$^{B2}$, R$^{B3}$, R$^{B4}$, R$^{B5}$, and R$^{B6}$ may be, for example, hydrogen, hydroxyl, C$_1$-C$_{20}$ alkyl, C$_5$-C$_{20}$ aryl, C$_1$-C$_{20}$ alkoxy, C$_5$-C$_{20}$ aryloxy, C$_2$-C$_{20}$ alkoxycarbonyl, C$_5$-C$_{20}$ aryloxycarbonyl, amino, amido, nitro, etc.

Furthermore, any of the R$^{B1}$, R$^{B2}$, R$^{B3}$, R$^{B4}$, R$^{B5}$, and R$^{B6}$ moieties can be linked to any of the other R$^{B1}$, R$^{B2}$, R$^{B3}$, R$^{B4}$, R$^{B5}$, and R$^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

Examples of monounsaturated, monocyclic olefins encompassed by structure (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by structure (A) may be generally represented by the structure (C)

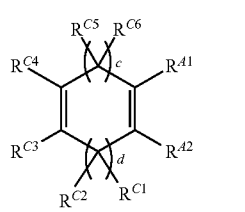

(C)

wherein c and d are independently integers in the range of 1 to about 8, typically 2 to 4, preferably 2 (such that the reactant is a cyclooctadiene), R$^{A1}$ and R$^{A2}$ are as defined above for structure (A), and R$^{C1}$, R$^{C2}$, R$^{C3}$, R$^{C4}$, R$^{C5}$, and R$^{C6}$ are defined as for R$^{B1}$ through R$^{B6}$. In this case, it is preferred that R$^{C3}$ and R$^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene structure (C), and will generally contain at least one methylene linkage between any two olefinic segments.

Bicyclic and polycyclic olefins encompassed by structure (A) may be generally represented by the structure (D)

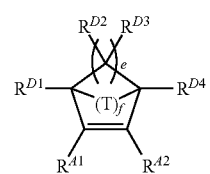

(D)

wherein R$^{A1}$ and R$^{A2}$ are as defined above for structure (A), R$^{D1}$, R$^{D2}$, R$^{D3}$, and R$^{D4}$ are as defined for R$^{B1}$ through R$^{B6}$, e is an integer in the range of 1 to 8 (typically 2 to 4) f is generally 1 or 2; T is lower alkylene or alkenylene (generally substituted or unsubstituted methyl or ethyl), CHR$^{G1}$, C(R$^{G1}$)$_2$, O, S, N—R$^{G1}$, P—R$^{G1}$, O=P—R$^{G1}$, Si(R$^{G1}$)$_2$, B—R$^{G1}$, or As—R$^{G1}$ where R$^{G1}$ is alkyl, alkenyl, cycloalkyl, cycloalkenyl, aryl, alkaryl, aralkyl, or alkoxy. Furthermore, any of the R$^{D1}$, R$^{D2}$, R$^{D3}$, and R$^{D4}$ moieties can be linked to any of the other R$^{D1}$, R$^{D2}$, R$^{D3}$, and R$^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

Cyclic olefins encompassed by structure (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the structure (E)

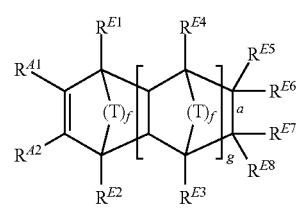

(E)

wherein R$^{A1}$ and R$^{A2}$ are as defined above for structure (A), T is as defined above for structure (D), R$^{E1}$, R$^{E2}$, R$^{E3}$, R$^{E4}$, R$^{E5}$, R$^{E6}$, R$^{E7}$, and R$^{E8}$ are as defined for R$^{B1}$ through R$^{B6}$, and "a" represents a single bond or a double bond, f is generally 1 or 2, "g" is an integer from 0 to 5, and when "a" is a double bond one of R$^{E5}$, R$^{E6}$ and one of R$^{E7}$, R$^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain mono-substitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

More preferred cyclic olefins possessing at least one norbornene moiety have the structure (F):

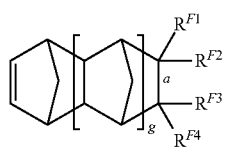

(F)

wherein, $R^{F1}$, $R^{F2}$, $R^{F3}$, and $R^{F4}$, are as defined for $R^{B1}$ through $R^{B6}$, and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$, and $R^{F4}$ moieties can be linked to any of the other $R^{F1}$, $R^{F2}$, $R^{F3}$, and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain mono-substitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is zero or 1, Z* and Fn are as defined previously, and functional groups (Fn) provided above.

One route for the preparation of hydrocarbyl substituted and functionally substituted norbornenes employs the Diels-Alder cycloaddition reaction in which cyclopentadiene or substituted cyclopentadiene is reacted with a suitable dienophile at elevated temperatures to form the substituted norbornene adduct generally shown by the following reaction Scheme 1:

SCHEME 1

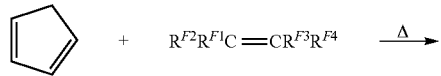

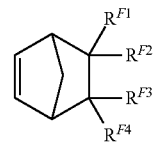

wherein $R^{F1}$ to $R^{F4}$ are as previously defined for structure (F).

Other norbornene adducts can be prepared by the thermal pyrolysis of dicyclopentadiene in the presence of a suitable dienophile. The reaction proceeds by the initial pyrolysis of dicyclopentadiene to cyclopentadiene followed by the Diels-Alder cycloaddition of cyclopentadiene and the dienophile to give the adduct shown below in Scheme 2:

SCHEME 2

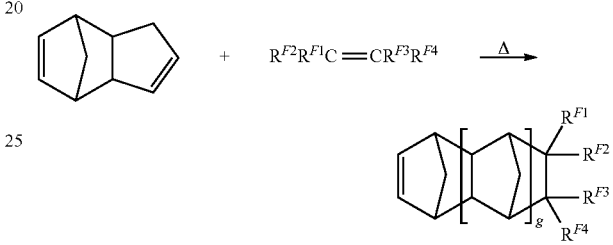

wherein "g" is an integer from 0 to 5, and $R^{F1}$ to $R^{F4}$ are as previously defined for structure (F).

Norbornadiene and higher Diels-Alder adducts thereof similarly can be prepared by the thermal reaction of cyclopentadiene and dicyclopentadiene in the presence of an acetylenic reactant as shown below in Scheme 3:

SCHEME 3

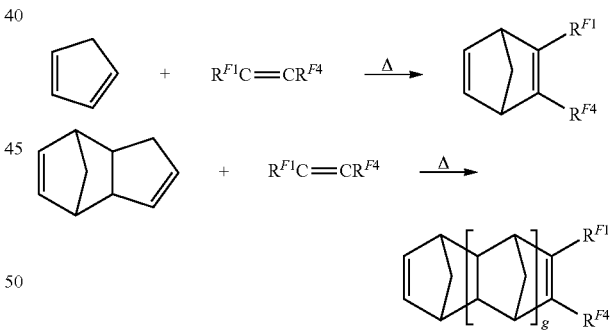

wherein "g" is an integer from 0 to 5, $R^{F1}$ and $R^{F4}$ are as previously defined for structure (F)

Examples of bicyclic and polycyclic olefins thus include, without limitation, dicyclopentadiene (DCPD); trimer and other higher order oligomers of cyclopentadiene including without limitation tricyclopentadiene (cyclopentadiene trimer), cyclopentadiene tetramer (tetracyclopentadiene), and cyclopentadiene pentamer (pentacyclopentadiene); ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxycarbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo,endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like. It is well understood by one in the art that bicyclic and polycyclic olefins as disclosed herein may consist of a variety of structural isomers and/or stereoisomers, any and all of which are suitable for use in the present invention. Any reference herein to such bicyclic and polycyclic olefins unless specifically stated includes mixtures of any and all such structural isomers and/or stereoisomers.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous O heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Preferred examples of cyclic olefins that comprise multiple rings include norbornene, dicyclopentadiene, tricyclopentadiene, and 5-ethylidene-2-norbornene.

The cyclic olefin may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (i.e., heteroatoms, substituents, multiple olefins, multiple rings) are suitable for the methods disclosed herein. Additionally, cyclic olefins incorporating any combination of the abovementioned features (i.e., heteroatoms, substituents, multiple olefins, multiple rings) are suitable for the invention disclosed herein.

The cyclic olefins useful in the methods disclosed herein may be strained or unstrained. It will be appreciated that the amount of ring strain varies for each cyclic olefin compound, and depends upon a number of factors including the size of the ring, the presence and identity of substituents, and the presence of multiple rings. Ring strain is one factor in determining the reactivity of a molecule towards ring-opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive. In some cases, ring opening reactions of relatively unstrained (and therefore relatively unreactive) cyclic olefins may become possible when performed in the presence of the olefinic compounds disclosed herein. Additionally, cyclic olefins useful in the invention disclosed herein may be strained or unstrained.

The resin compositions and/or cyclic olefin compositions of the present invention may comprise a plurality of cyclic olefins. A plurality of cyclic olefins may be used to prepare metathesis polymers from the olefinic compound. For example, two cyclic olefins selected from the cyclic olefins described hereinabove may be employed in order to form metathesis products that incorporate both cyclic olefins. Where two or more cyclic olefins are used, one example of a second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products and polymers formed.

Examples of cyclic olefins include dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyl-tetracyclododecene; 8-methoxycarbonyltetracyclododecene; 8-methyl-8-tetracyclo-dodecene;

8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like.

Examples of cyclic olefins include dicyclopentadiene, tricyclopentadiene, and higher order oligomers of cyclopentadiene, such as cyclopentadiene tetramer, cyclopentadiene pentamer, and the like, including structural isomers and/or stereoisomers, any and all of which are suitable for use in the present invention. Examples of cyclic olefins include dicyclopentadiene, tricyclopentadiene, and tetracyclopentadiene, including structural isomers and/or stereoisomers, any and all of which are suitable for use in the present invention. Examples of cyclic olefins include dicyclopentadiene and tricyclopentadiene, including structural isomers and/or stereoisomers, any and all of which are suitable for use in the present invention.

Metal Carbene Olefin Metathesis Catalysts

Catalyst compositions that may be used with the present invention disclosed herein comprise one or more metal carbene olefin metathesis catalysts. Metal carbene olefin metathesis catalysts that may be used in the invention disclosed herein, are preferably a Group 8 transition metal complex having the structure of formula (I)

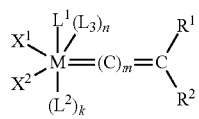

(I)

in which:

M is a Group 8 transition metal;
$L^1$, $L^2$, and $L^3$ are neutral electron donor ligands;
n is 0 or 1, such that $L^3$ may or may not be present;
m is 0, 1, or 2;
k is 0 or 1;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Additionally, in formula (I), one or both of $R^1$ and $R^2$ may have the structure $-(W)_n-U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety.

Preferred catalysts contain Ru or Os as the Group 8 transition metal, with Ru particularly preferred.

Numerous embodiments of the catalysts useful in the reactions disclosed herein are described in more detail infra. For the sake of convenience, the catalysts are described in groups, but it should be emphasized that these groups are not meant to be limiting in any way. That is, any of the catalysts useful in the invention may fit the description of more than one of the groups described herein.

A first group of catalysts, then, are commonly referred to as First Generation Grubbs-type catalysts, and have the structure of formula (I). For the first group of catalysts, M is a Group 8 transition metal, m is 0, 1, or 2, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred, $L^1$ and $L^2$ are independently selected from the group consisting of trimethylphosphine ($PMe_3$), triethylphosphine ($PEt_3$), tri-n-butylphosphine ($PBu_3$), tri(ortho-tolyl)phosphine (P-o-$tolyl_3$), tri-tert-butylphosphine (P-tert-$Bu_3$), tricyclopentylphosphine ($PCyclopentyl_3$), tricyclohexylphosphine ($PCy_3$), triisopropylphosphine (P-i-$Pr_3$), trioctylphosphine ($POct_3$), triisobutylphosphine, (P-i-$Bu_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), and diethylphenylphosphine ($PEt_2Ph$). Alternatively, $L^1$ and $L^2$ may be independently selected from phosphabicycloalkane (e.g., monosubstituted 9-phosphabicyclo-[3.3.1]nonane, or monosubstituted 9-phosphabicyclo [4.2.1]nonane] such as cyclohexylphoban, isopropylphoban, ethylphoban, methylphoban, butylphoban, pentylphoban and the like).

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, $-N=C=O$, $-N=C=S$, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or $-CH=C(CH_3)_2$.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of metal carbene olefin metathesis catalysts, commonly referred to as Second Generation Grubbs-type catalysts, have the structure of formula (I), wherein $L^1$ is a carbene ligand having the structure of formula (II)

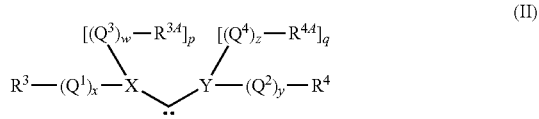

(II)

such that the complex may have the structure of formula (III)

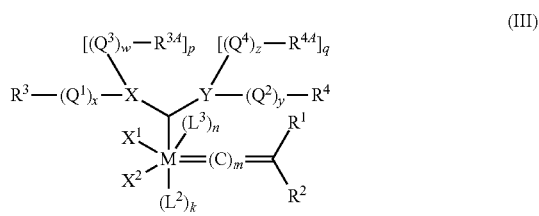

(III)

wherein M, m, n, $X^1$, $X^2$, $L^2$, $L^3$, $R^1$, and $R^2$ are as defined for the first group of catalysts, and the remaining substituents are as follows;

X and Y are heteroatoms typically selected from N, O, S, and P. Since O and S are divalent, p is necessarily zero when X is O or S, q is necessarily zero when Y is O or S, and k is zero or 1. However, when X is N or P, then p is 1, and when Y is N or P, then q is 1. In a preferred embodiment, both X and Y are N;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or $-(CO)-$, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl. In addition, X and Y may be independently selected from carbon and one of the heteroatoms mentioned above, preferably no more than one of X or Y is carbon. Also, $L^2$ and $L^3$ may be taken together to form a single bindentate electron-donating heterocyclic ligand. Furthermore, $R^1$ and $R^2$ may be taken together to form an indenylidene moiety. Moreover, $X^1$, $X^2$, $L^2$, $L^3$, X and Y may be further coordinated to boron or to a carboxylate.

In addition, any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $Q^3$, and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support. Any two or more of $X^1$, $X^2$, $L^1$, $L^2$, $L^3$, $R^1$, $R^2$, $R^3$, $R^{3A}$, $R^4$, and $R^{4A}$ can also be taken to be -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein hetero atoms and/or functional groups may be present in either the aryl or the alkyl portions of the alkylene and arylalkylene groups, and Fn is a functional group, or together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

A particular class of carbene ligands having the structure of formula (II), where $R^{3A}$ and $R^{4A}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC) ligands.

Preferably, $R^{3A}$ and $R^{4A}$ are linked to form a cyclic group so that the carbene ligand has the structure of formula (IV)

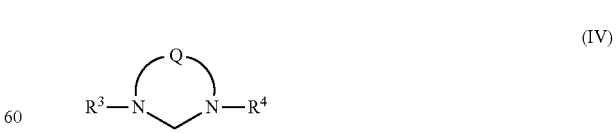

(IV)

wherein $R^3$ and $R^4$ are as defined for the second group of catalysts above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands suitable as $L^1$ thus include, but are not limited to, the following where DIPP or DiPP is diisopropylphenyl and Mes is 2,4,6-trimethylphenyl:

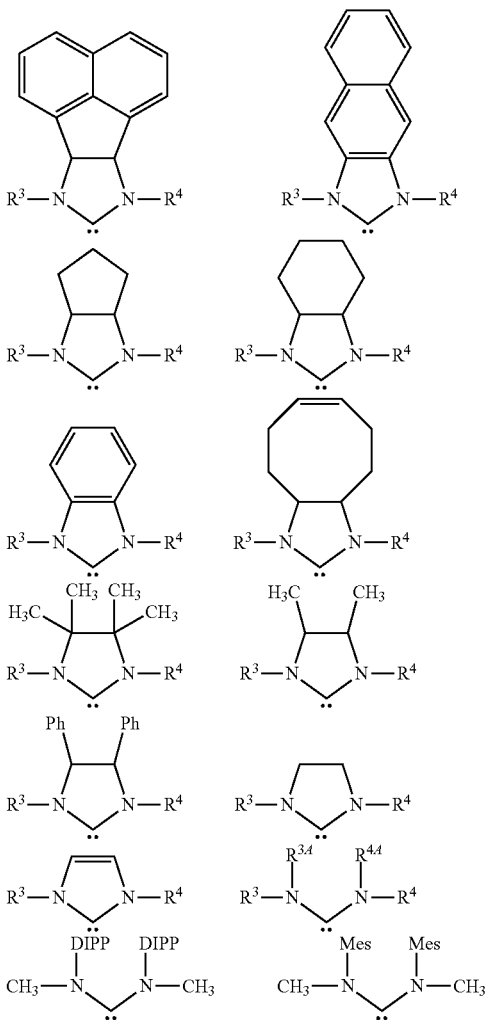

Additional examples of N-heterocyclic carbene (NHC) ligands and acyclic diaminocarbene ligands suitable as $L^1$ thus include, but are not limited to the following:

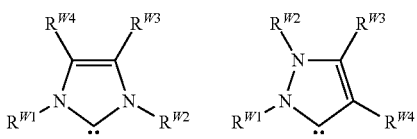

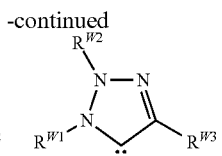

wherein $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halogen, nitro, amido, carboxyl, alkoxy, aryloxy, sulfonyl, carbonyl, thio, or nitroso groups.

Additional examples of N-heterocyclic carbene (NHC) ligands suitable as $L^1$ are further described in U.S. Pat. Nos. 7,378,528; 7,652,145; 7,294,717; 6,787,620; 6,635,768; and 6,552,139, the contents of each are incorporated herein by reference.

Additionally, thermally activated N-Heterocyclic Carbene Precursors as disclosed in U.S. Pat. No. 6,838,489, the contents of which are incorporated herein by reference, may also be used with the present invention.

When M is ruthenium, then, the preferred complexes have the structure of formula (V)

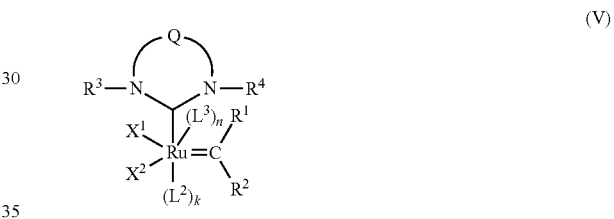

(V)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include without limitation carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e., Mes as defined herein).

In a third group of metal carbene olefin metathesis catalysts having the structure of formula (I), M, m, n, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of metal carbene olefin metathesis catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substituent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, $L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VI)

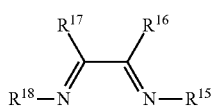

(VI)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of metal carbene olefin metathesis catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$ CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$—. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein Y is coordinated to the metal are examples of a fifth group of metal carbene olefin metathesis catalysts, and are commonly called "Grubbs-Hoveyda" catalysts. Grubbs-Hoveyda metathesis-active metal carbene complexes may be described by the formula (VII)

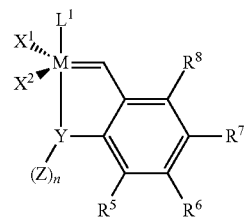

(VII)

wherein,

M is a Group 8 transition metal, particularly Ru or Os, or, more particularly, Ru;

$X^1$, $X^2$, and $L^1$ are as previously defined herein for the first and second groups of catalysts;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $X^2$, $L^1$, Y, Z, $R^5$, $R^6$, $R^7$, and $R^8$ may be linked to a support. Additionally, $R^5$, $R^6$, $R^7$, $R^8$, and Z may independently be thioisocyanate, cyanato, or thiocyanato.

Examples of complexes comprising Grubbs-Hoveyda ligands suitable in the invention include:

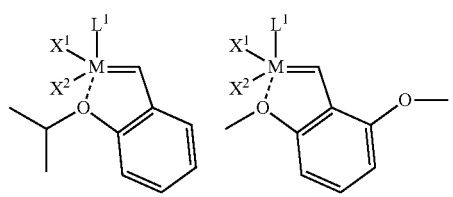

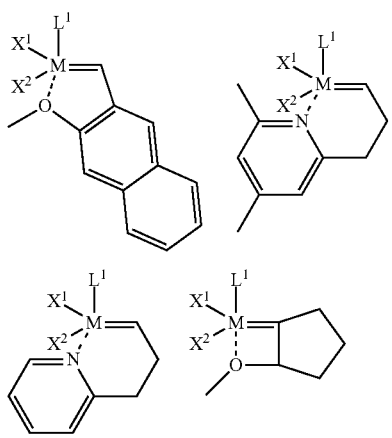

wherein, $L^1$, $X^1$, $X^2$, and M are as described for any of the other groups of catalysts. Suitable chelating carbenes and carbene precursors are further described by Pederson et al. (U.S. Pat. Nos. 7,026,495 and 6,620,955, the disclosures of both of which are incorporated herein by reference) and Hoveyda et al. (U.S. Pat. No. 6,921,735 and WO0214376, the disclosures of both of which are incorporated herein by reference).

Other useful complexes include structures wherein $L^2$ and $R^2$ according to formulae (I), (III), or (V) are linked, such as styrenic compounds that also include a functional group for attachment to a support. Examples in which the functional group is a trialkoxysilyl functionalized moiety include, but are not limited to, the following:

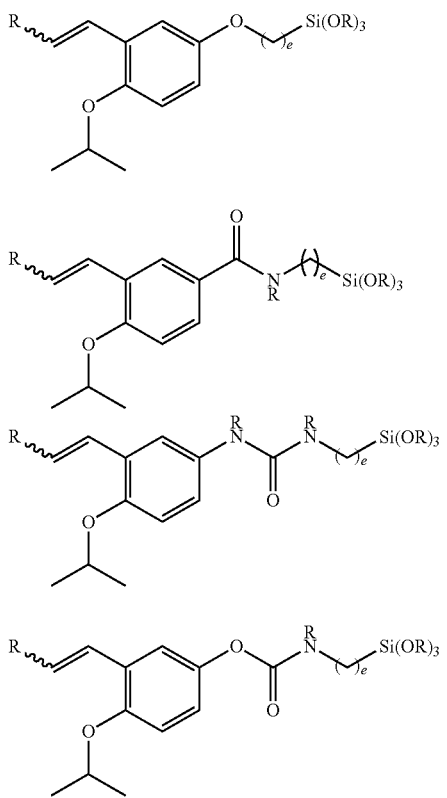

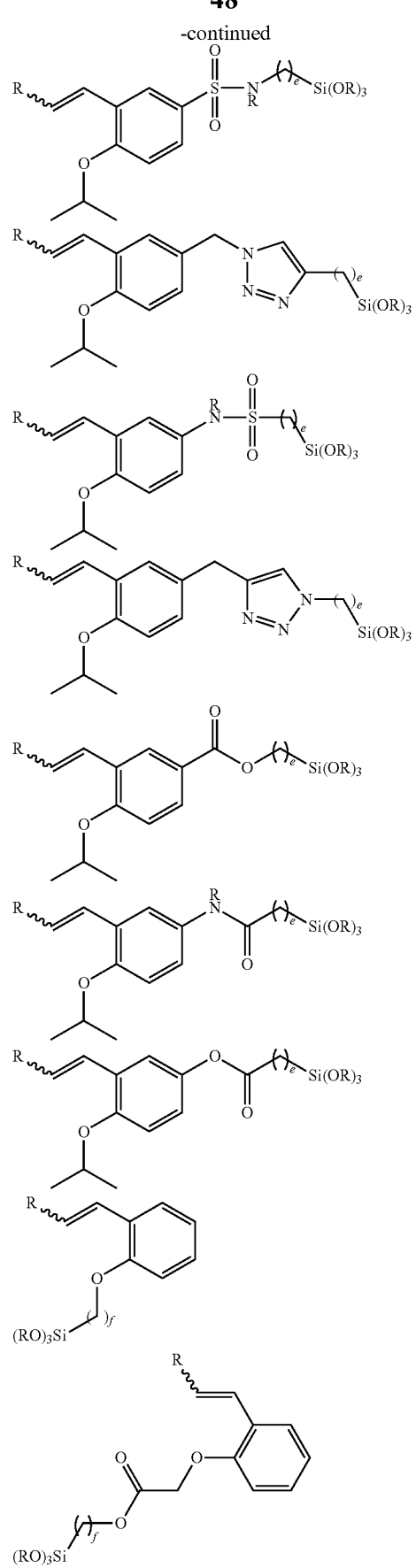

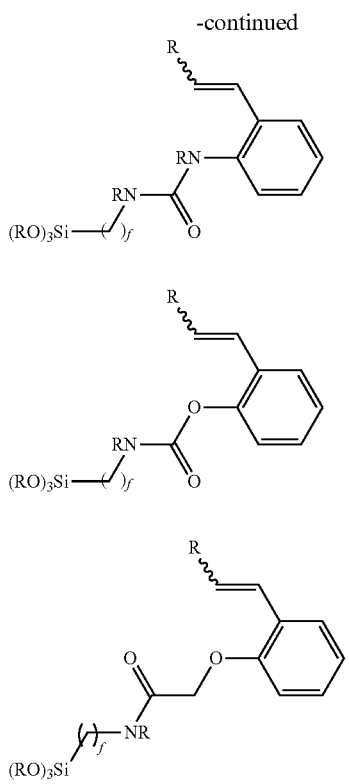

Further examples of complexes having linked ligands include those having linkages between a neutral NHC ligand and an anionic ligand, a neutral NHC ligand and an alkylidine ligand, a neutral NHC ligand and an $L^2$ ligand, a neutral NHC ligand and an $L^3$ ligand, an anionic ligand and an alkylidine ligand, and any combination thereof. While the possible structures are too numerous to list herein, some suitable structures based on formula (III) include:

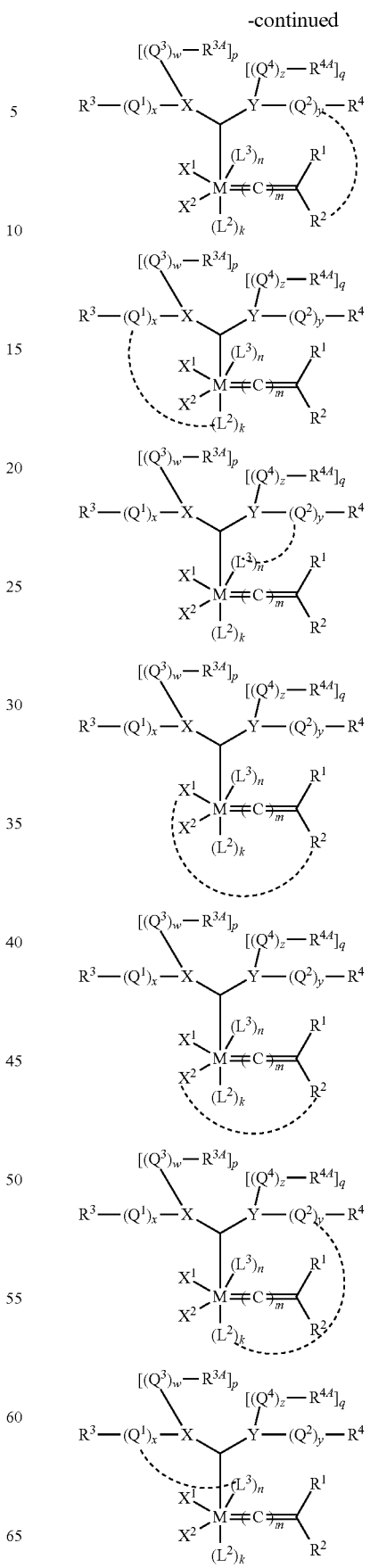

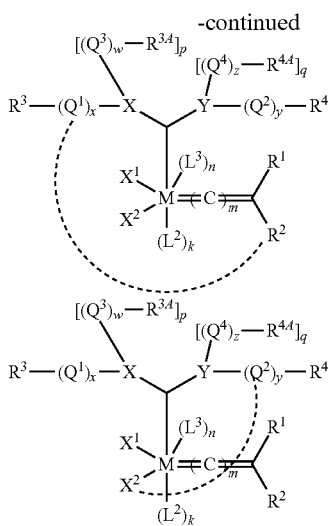

In addition to the metal carbene olefin metathesis catalysts that have the structure of formula (I), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14 or 16, are tetra-coordinated or penta-coordinated, respectively, and are of the general formula (XII)

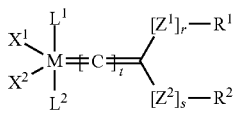 (IX)

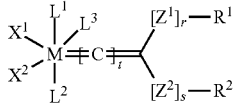 (X)

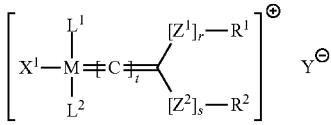 (XI)

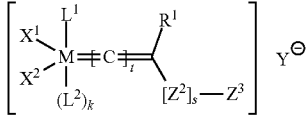 (XII)

wherein:

M, $X^1$, $X^2$, $L^1$, $L^2$, $L^3$, $R^1$, and $R^2$ are as defined for any of the previously defined four groups of catalysts;

r and s are independently zero or 1;

t is an integer in the range of zero to 5;

k is an integer in the range of zero to 1;

Y is any non-coordinating anion (e.g., a halide ion, $BF_4^-$, etc.);

$Z^1$ and $Z^2$ are independently selected from —O—, —S—, —$NR^2$—, —$PR^2$—, —P(=O)$R^2$—, —P(O$R^2$)—, P(=O)(O$R^2$)—, —C(=O)—, —C(=O)O—, —OC(=O)—, —OC(=O)O—, —S(=O)—, —S(=O)$_2$—, -, and an optionally substituted and/or optionally heteroatom-containing $C_1$-$C_{20}$ hydrocarbylene linkage;

$Z^3$ is any cationic moiety such as —P($R^2$)$_3^+$ or —N($R^2$)$_3^+$; and any two or more of $X^1$, $X^2$, $L^1$, $L^2$, $L^3$, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, $L^3$, $Z^1$, $Z^2$, $Z^3$, $R^1$, and $R^2$ may be attached to a support.

Additionally, another group of metal carbene olefin metathesis catalysts that may be used in the invention disclosed herein, is a Group 8 transition metal complex having the structure of formula (XIII):

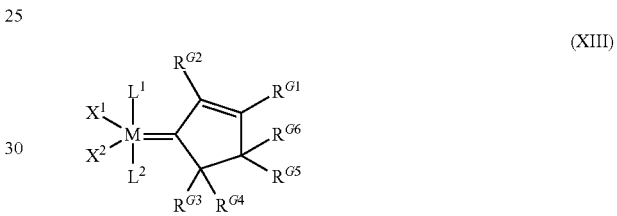 (XIII)

wherein M is a Group 8 transition metal, particularly ruthenium or osmium, or more particularly, ruthenium;

$X^1$, $X^2$, $L^1$ and $L^2$ are as defined for the first and second groups of catalysts defined above; and $R^{G1}$, $R^{G2}$, $R^{G3}$, $R^{G4}$, $R^{G5}$, and $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group, or any one or more of the $R^{G1}$, $R^{G2}$, $R^{G3}$, $R^{G4}$, $R^{G5}$, and $R^{G6}$ may be attached to a support.

Additionally, one preferred embodiment of the Group 8 transition metal complex of formula XIII is a Group 8 transition metal complex of formula (XIV):

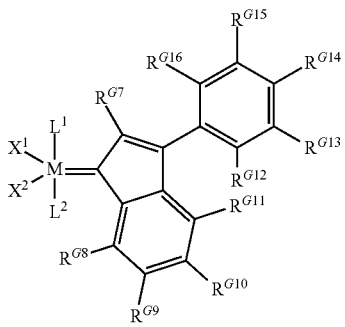

(XIV)

wherein M, $X^1$, $X^2$, $L^1$, $L^2$, are as defined above for Group 8 transition metal complex of formula XIII; and $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ are as defined above for $R^{G1}$, $R^{G2}$, $R^{G3}$, $R^{G4}$, $R^{G5}$, and $R^{G6}$ for Group 8 transition metal complex of formula XIII or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be linked together to form a cyclic group, or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be attached to a support.

Additionally, another preferred embodiment of the Group 8 transition metal complex of formula XIII is a Group 8 transition metal complex of formula (XV):

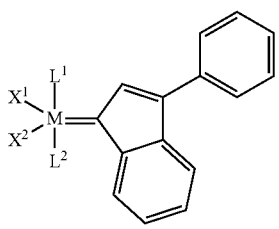

(XV)

wherein M, $X^1$, $X^2$, $L^1$, $L^2$, are as defined above for Group 8 transition metal complex of formula XIII.

Additionally, another group of olefin metathesis catalysts that may be used in the invention disclosed herein, is a Group 8 transition metal complex comprising a Schiff base ligand having the structure of formula (XVI):

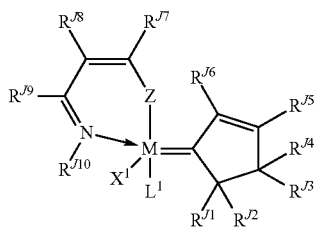

(XVI)

wherein M is a Group 8 transition metal, particularly ruthenium or osmium, or more particularly, ruthenium;

$X^1$, and $L^1$ are as defined for the first and second groups of catalysts defined above;

Z is selected from the group consisting of oxygen, sulfur, selenium, $NR^{J11}$, $PR^{J11}$, $AsR^{J11}$, and $SbR^{J11}$; and $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be linked together to form a cyclic group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be attached to a support.

Additionally, one preferred embodiment of the Group 8 transition metal complex of formula (XVI) is a Group 8 transition metal complex comprising a Schiff base ligand having the structure of formula (XVII):

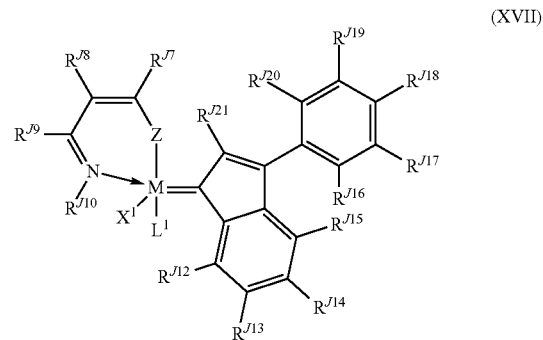

(XVII)

wherein M, $X^1$, $L^1$, Z, $R^{J7}$, $R^{J8}$, $R^{J9}$, $R^{J10}$, and $R^{J11}$ are as defined above for Group 8 transition metal complex of formula XVI; and $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ are as defined above for $R^{J1}$, $R^{J2}$, $R^{J3}$, $R^{J4}$, $R^{J5}$, and $R^{J6}$ for Group 8 transition metal complex of formula XVI, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be linked together to form a cyclic group, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be attached to a support.

Additionally, another preferred embodiment of the Group 8 transition metal complex of formula (XVI) is a Group 8 transition metal complex comprising a Schiff base ligand having the structure of formula (XVIII):

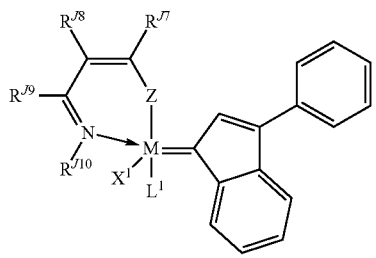

(XVIII)

wherein M, $X^1$, $L^1$, Z, $R^{J7}$, $R^{J8}$, $R^{J9}$, $R^{J10}$, and $R^{J11}$, are as defined above for Group 8 transition metal complex of formula (XVI).

Additionally, another group of olefin metathesis catalysts that may be used in the invention disclosed herein, is a Group 8 transition metal complex comprising a Schiff base ligand having the structure of formula (XIX):

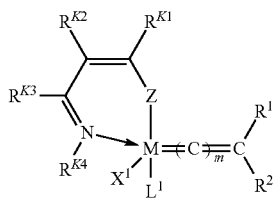

(XIX)

wherein M is a Group 8 transition metal, particularly ruthenium or osmium, or more particularly, ruthenium;

$X^1$, $L^1$, $R^1$, and $R^2$ are as defined for the first and second groups of catalysts defined above;

Z is selected from the group consisting of oxygen, sulfur, selenium, $NR^{K5}$, $PR^{K5}$, $AsR^{K5}$, and $SbR^{K5}$;

m is 0, 1, or 2; and $R^{K1}$, $R^{K2}$, $R^{K3}$, $R^{K4}$, and $R^{K5}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{K1}$, $R^{K2}$, $R^{K3}$, $R^{K4}$, and $R^{K5}$ may be linked together to form a cyclic group, or any one or more of the $R^{K1}$, $R^{K2}$, $R^{K3}$, $R^{K4}$, and $R^{K5}$ may be attached to a support.

In addition, catalysts of formulas (XVI) to (XIX) may be optionally contacted with an activating compound, where at least partial cleavage of a bond between the Group 8 transition metal and at least one Schiff base ligand occurs, wherein the activating compound is either a metal or silicon compound selected from the group consisting of copper (I) halides; zinc compounds of the formula $Zn(R^{Y1})_2$, wherein $R^{Y1}$ is halogen, $C_1$-$C_7$ alkyl or aryl; tin compounds represented by the formula $SnR^{Y2}R^{Y3}R^{Y4}R^{Y5}$ wherein each of $R^{Y2}$, $R^{Y3}$, $R^{Y4}$ and $R^{Y5}$ is independently selected from the group consisting of halogen, $C_1$-$C_{20}$ alkyl, $C_3$-$C_{10}$ cycloalkyl, aryl, benzyl and $C_2$-$C_7$ alkenyl; and silicon compounds represented by the formula $SiR^{Y6}R^{Y7}R^{Y8}R^{Y9}$ wherein each of $R^{Y6}$, $R^{Y7}$, $R^{Y8}$, $R^{Y9}$ is independently selected from the group consisting of hydrogen, halogen, $C_1$-$C_{20}$ alkyl, halo, $C_1$-$C_7$ alkyl, aryl, heteroaryl, and vinyl. In addition, catalysts of formulas (XVI) to (XIX) may be optionally contacted with an activating compound where at least partial cleavage of a bond between the Group 8 transition metal and at least one Schiff base ligand occurs, wherein the activating compound is an inorganic acid such as hydrogen iodide, hydrogen bromide, hydrogen chloride, hydrogen fluoride, sulfuric acid, nitric acid, iodic acid, periodic acid, perchloric acid, HOClO, $HOClO_2$ and $HOIO_3$. In addition, catalysts of formulas (XVI) to (XIX) may be optionally contacted with an activating compound where at least partial cleavage of a bond between the Group 8 transition metal and at least one Schiff base ligand occurs, wherein the activating compound is an organic acid such as sulfonic acids including but not limited to methanesulfonic acid, aminobenzenesulfonic acid, benzenesulfonic acid, napthalenesulfonic acid, sulfanilic acid and trifluoromethanesulfonic acid; monocarboxylic acids including but not limited to acetoacetic acid, barbituric acid, bromoacetic acid, bromobenzoic acid, chloroacetic acid, chlorobenzoic acid, chlorophenoxyacetic acid, chloropropionic acid, cis-cinnamic acid, cyanoacetic acid, cyanobutyric acid, cyanophenoxyacetic acid, cyanopropionic acid, dichloroacetic acid, dichloroacetylacetic acid, dihydroxybenzoic acid, dihydroxymalic acid, dihydroxytartaric acid, dinicotinic acid, diphenylacetic acid, fluorobenzoic acid, formic acid, furancarboxylic acid, furoic acid, glycolic acid, hippuric acid, iodoacetic acid, iodobenzoic acid, lactic acid, lutidinic acid, mandelic acid, α-naphtoic acid, nitrobenzoic acid, nitrophenylacetic acid, o-phenylbenzoic acid, thioacetic acid, thiophene-carboxylic acid, trichloroacetic acid, and trihydroxybenzoic acid; and other acidic substances such as but not limited to picric acid and uric acid.

In addition, other examples of catalysts that may be used with the present invention are located in the following disclosures, each of which is incorporated herein by reference, U.S. Pat. Nos. 7,687,635; 7,671,224; 6,284,852; 6,486,279; and 5,977,393; International Publication Number WO2010/037550; and U.S. patent application Ser. Nos. 12/303,615; 10/590,380; 11/465,651 (Publication No.: US 2007/0043188); and Ser. No. 11/465,651 (Publication No.: US 2008/0293905 Corrected Publication); and European Pat. Nos. EP1757613B1 and EP1577282B1.

Non-limiting examples of metal carbene olefin metathesis catalysts that may be used to prepare supported complexes and in the reactions disclosed herein include the following, some of which for convenience are identified throughout this disclosure by reference to their molecular weight:

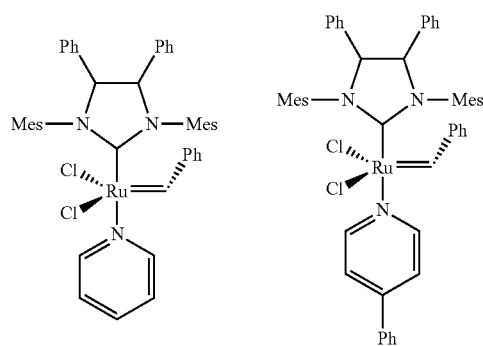

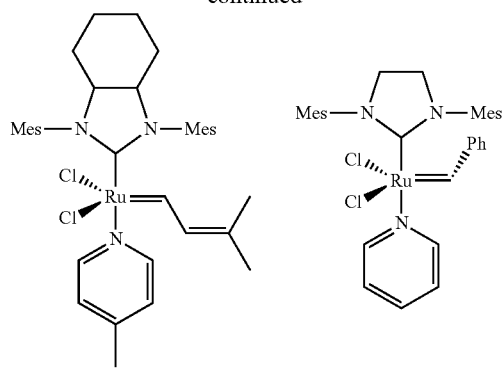
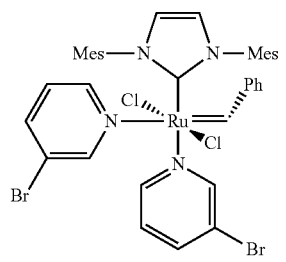
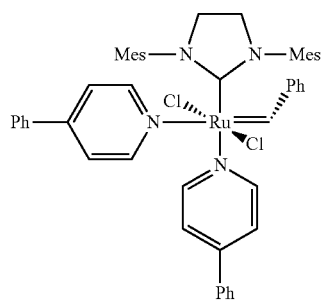
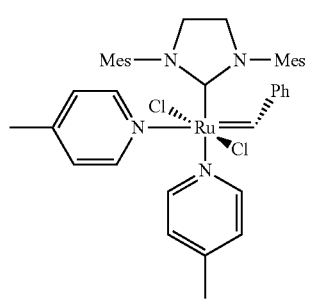
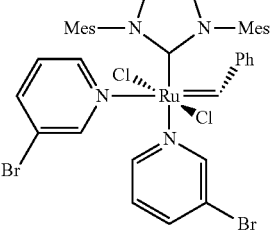
C884
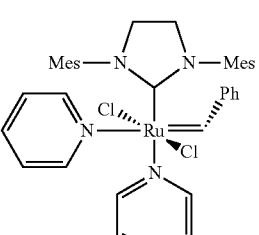
C727
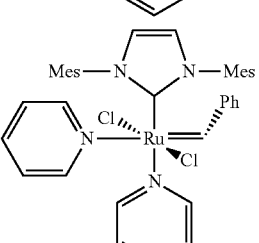
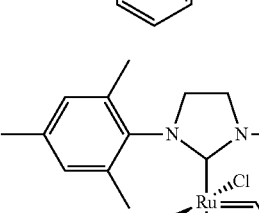
C827
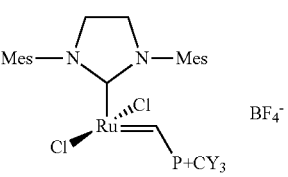
C859
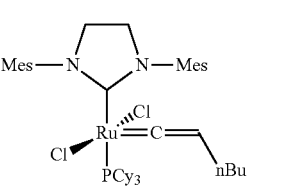
C841-n
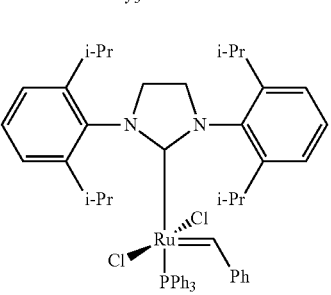
C916

C965-p
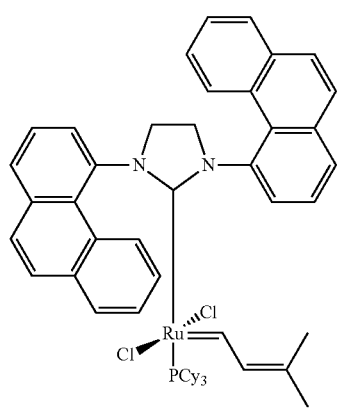
C727
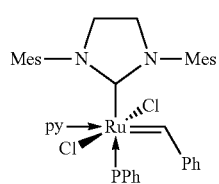
C577
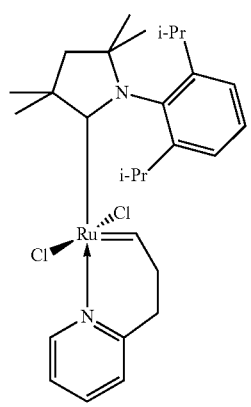
C646
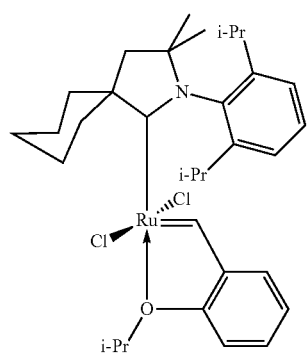
C701
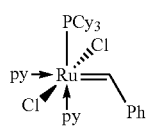
C767-m
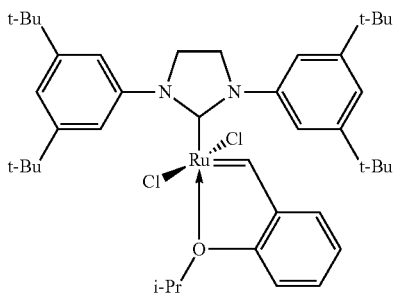
C811
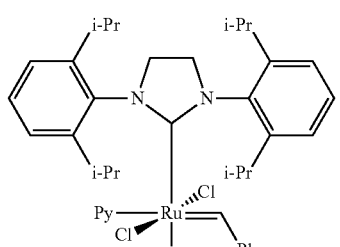
C801
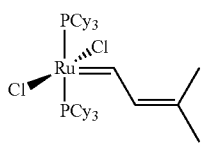
C838
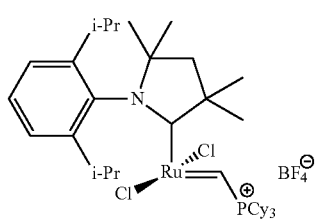
C712
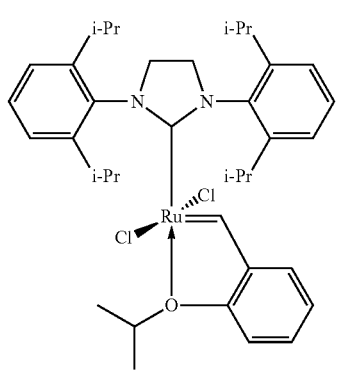
C933
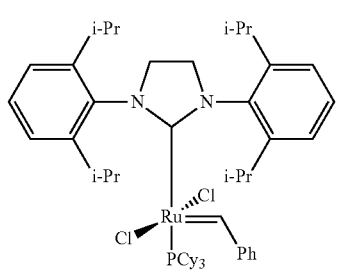

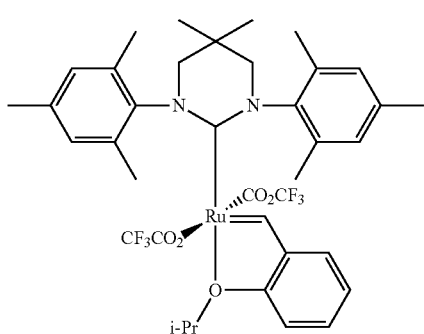
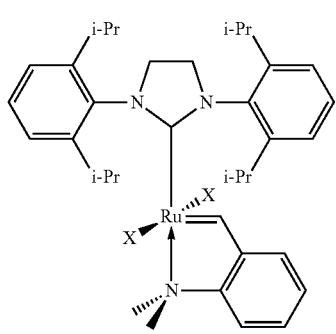
C697 (X = Cl)
C785 (X = Br)
C879 (X = I)
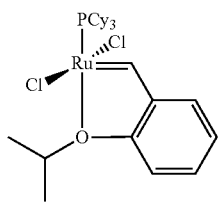
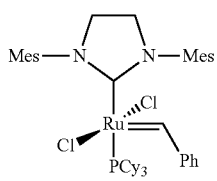
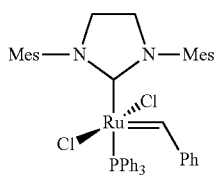
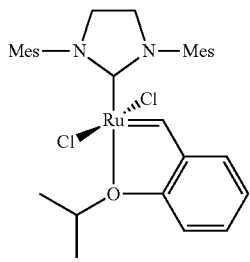
C824
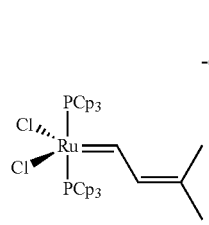
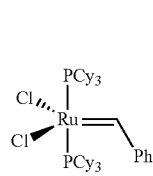
C716
C823
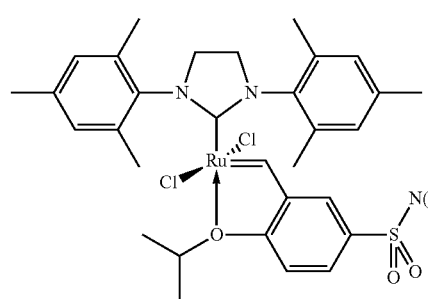
C601
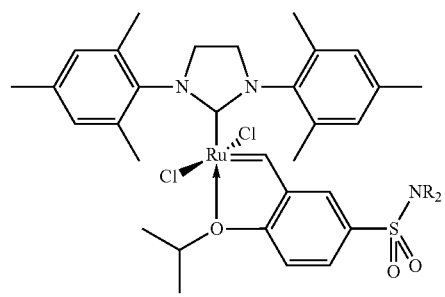
C848
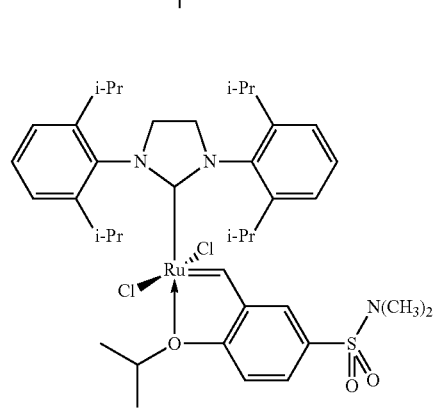
C831
C627
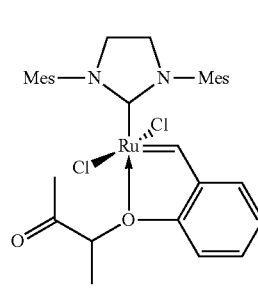

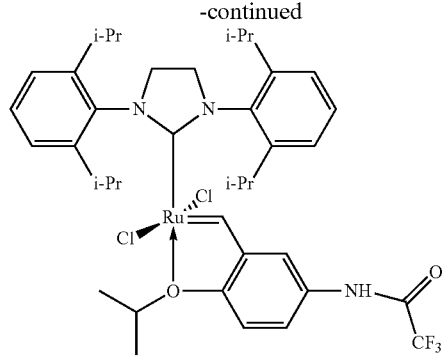
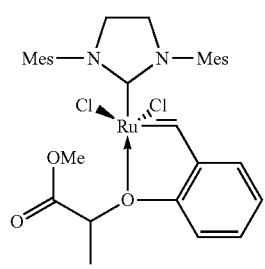
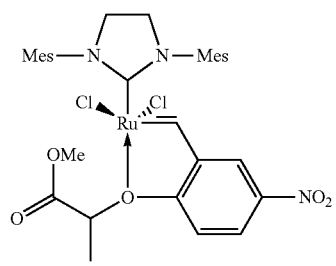
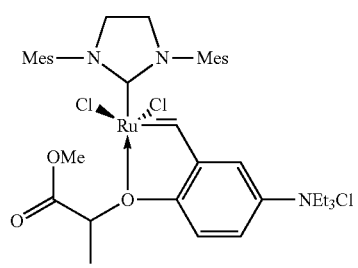
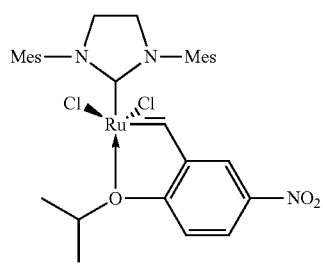
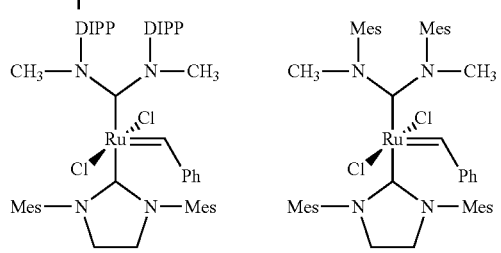
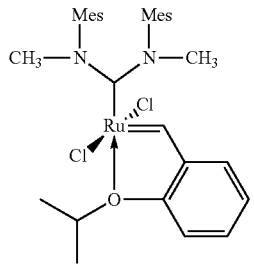
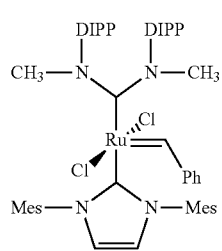
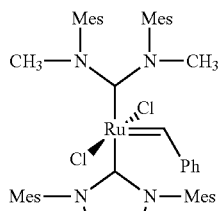
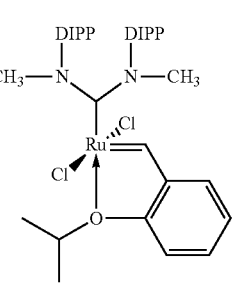
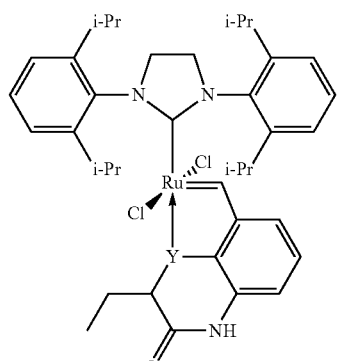
Y = O, S, NH
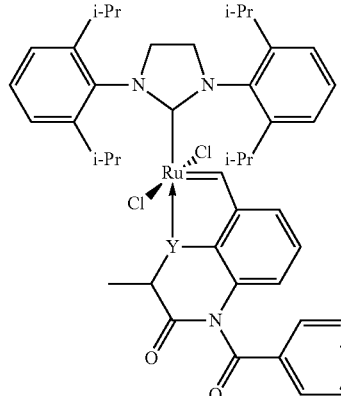
Y = O, S, NH

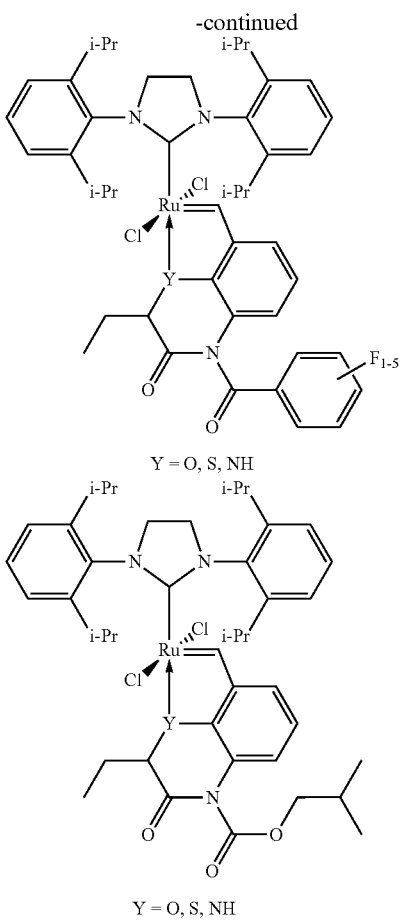

Y = O, S, NH

Y = O, S, NH

In the foregoing molecular structures and formulae, Ph represents phenyl, Cy represents cyclohexyl, Cp represents cyclopentyl, Me represents methyl, Bu represents n-butyl, t-Bu represents tert-butyl, i-Pr represents isopropyl, py represents pyridine (coordinated through the N atom), Mes represents mesityl (i.e., 2,4,6-trimethylphenyl), DiPP and DIPP represents 2,6-diisopropylphenyl, and MiPP represents 2-isopropylphenyl.

Further examples of metal carbene olefin metathesis catalysts useful to prepare supported complexes and in the reactions disclosed herein include the following: ruthenium (II) dichloro (3-methyl-2-butenylidene) bis(tricyclopentylphosphine) (C716); ruthenium (II) dichloro (3-methyl-2-butenylidene) bis(tricyclohexylphosphine) (C801); ruthenium (II) dichloro(phenylmethylene) bis (tricyclohexylphosphine) (C823); ruthenium (II) (1,3-bis-(2, 4,6-trimethylphenyl)-2-imidazolidinylidene) dichloro (phenylmethylene) (triphenylphosphine) (C830); ruthenium (II) dichloro (phenylvinylidene) bis(tricyclohexylphosphine) (C835a); ruthenium (II) dichloro (tricyclohexylphosphine) (o-isopropoxyphenylmethylene) (C601); ruthenium (II) (1,3-bis-(2, 4,6-trimethylphenyl)-2-imidazolidinylidene) dichloro (phenylmethylene) bis(3-bromopyridine) (C884); [1,3-bis-(2,4,6-trimethylphenyl)-2-imidazolidinylidene]dichloro(o-isopropoxyphenylmethylene)ruthenium(II) (C627); [1,3-bis-(2,4,6-trimethylphenyl)-2-imidazolidinylidene]dichloro (benzylidene) (triphenylphosphine) ruthenium(II) (C831); [1,3-bis-(2,4,6-trimethylphenyl)-2-imidazolidinylidene]dichloro (benzylidene)(methyldiphenylphosphine)ruthenium(II) (C769); [1,3-bis-(2,4,6-trimethylphenyl)-2-imidazolidinylidene]dichloro(benzylidene) (tricyclohexylphosphine)ruthenium(II) (C848); [1,3-bis-(2, 4,6-trimethylphenyl)-2-imidazolidinylidene]dichloro (benzylidene) (diethylphenylphosphine) ruthenium(II) (C735); [1,3-bis-(2,4,6-trimethylphenyl)-2-imidazolidinylidene]dichloro(benzylidene)(tri-n-butylphosphine)ruthenium(II) (C771); [1,3-bis-(2,4,6-trimethylphenyl)-2-imidazolidinylidene]dichloro(3-methyl-2-butenylidene) (triphenylphosphine)ruthenium(II) (C809); [1,3-bis-(2,4,6-trimethylphenyl)-2-imidazolidinylidene]dichloro(3-methyl-2-butenylidene)(methyldiphenylphosphine)ruthenium(II) (C747); [1,3-bis-(2,4,6-trimethylphenyl)-2-imidazolidinylidene]dichloro(3-methyl-2-butenylidene) (tricyclohexylphosphine) ruthenium(II) (C827); [1,3-bis-(2,4,6-trimethylphenyl)-2-imidazolidinylidene]dichloro(3-methyl-2-butenylidene)(diethylphenylphosphine)ruthenium(II) (C713); [1,3-bis-(2,4,6-trimethylphenyl)-2-imidazolidinylidene]dichloro (3-methyl-2-butenylidene) (tri-n-butylphosphine)ruthenium(II) (C749); [1,3-bis-(2,4,6-trimethylphenyl)-2-imidazolidinylidene]dichloro (phenylindenylidene)(triphenylphosphine)ruthenium(II) (C931); [1,3-bis-(2,4,6-trimethylphenyl)-2-imidazolidinylidene]dichloro (phenylindenylidene) (methylphenylphosphine) ruthenium(II) (C869); [1,3-bis-(2,4,6-trimethylphenyl)-2-imidazolidinylidene]dichloro (phenylindenylidene) (tricyclohexylphosphine) ruthenium (II) (C949); [1,3-bis-(2,4,6-trimethylphenyl)-2-imidazolidinylidene]dichloro(phenylindenylidene)(diethylphenylphosphine)ruthenium(II) (C835); and [1,3-bis-(2,4,6-trimethylphenyl)-2-imidazolidinylidene]dichloro (phenylindenylidene)(tri-n-butylphosphine)ruthenium(II) (C871).

Still further metal carbene olefin metathesis catalysts useful in ROMP reactions, and/or in other metathesis reactions, such as ring-closing metathesis, cross metathesis, ring-opening cross metathesis, self-metathesis, ethenolysis, alkenolysis, acyclic diene metathesis polymerization, and combinations thereof, include the following structures:

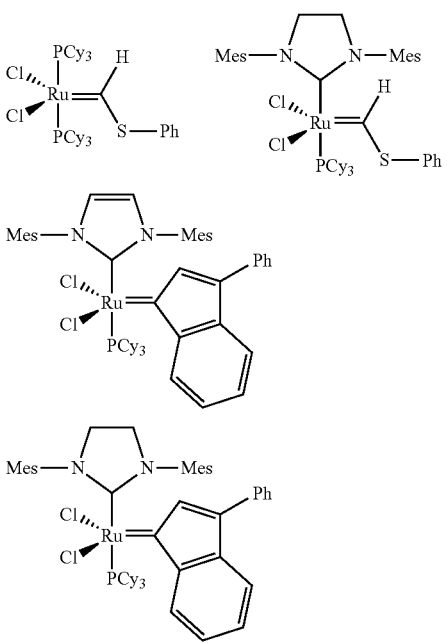

-continued
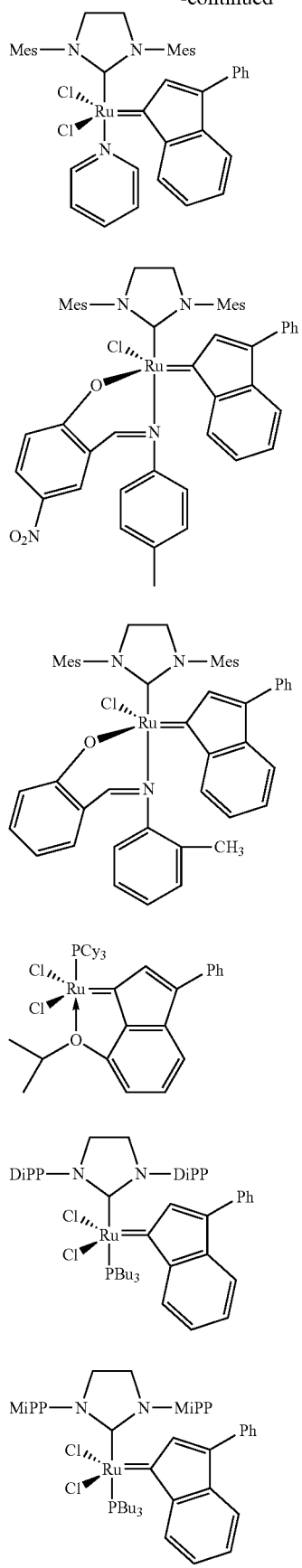
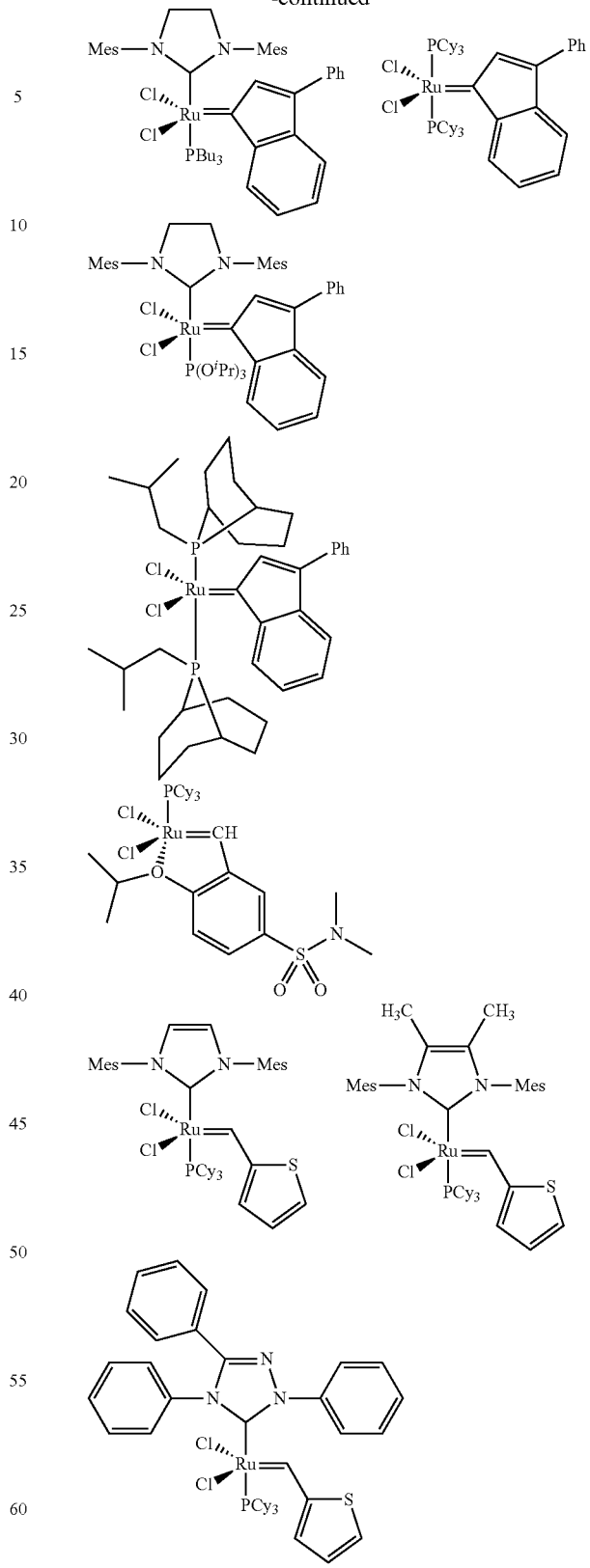
In general, the transition metal complexes used as catalysts herein can be prepared by several different methods, such as those described by Schwab et al. (1996) *J. Am. Chem. Soc.* 118:100-110, Scholl et al. (1999) *Org. Lett.*

6:953-956, Sanford et al. (2001) *J. Am. Chem. Soc.* 123: 749-750, U.S. Pat. No. 5,312,940, and U.S. Pat. No. 5,342,909, the disclosures of each of which are incorporated herein by reference. Also see U.S. Pat. Pub. No. 2003/0055262 to Grubbs et al., WO 02/079208, and U.S. Pat. No. 6,613,910 to Grubbs et al., the disclosures of each of which are incorporated herein by reference. Preferred synthetic methods are described in WO 03/11455A1 to Grubbs et al., the disclosure of which is incorporated herein by reference.

Examples of metal carbene olefin metathesis catalysts are Group 8 transition metal complexes having the structure of formula (I) commonly called "First Generation Grubbs" catalysts, formula (III) commonly called "Second Generation Grubbs" catalysts, or formula (VII) commonly called "Grubbs-Hoveyda" catalysts.

Examples of metal carbene olefin metathesis catalysts have the structure of formula (I)

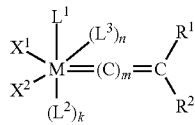

(I)

in which:
M is a Group 8 transition metal;
$L^1$, $L^2$, and $L^3$ are neutral electron donor ligands;
n is 0 or 1;
m is 0, 1, or 2;
k is 0 or 1;
$X^1$ and $X^2$ are anionic ligands;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support;
and formula (VII)

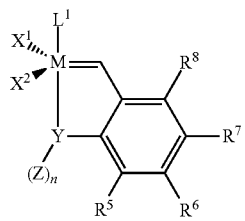

(VII)

wherein,
M is a Group 8 transition metal;
$L^1$ is a neutral electron donor ligand;
$X^1$ and $X^2$ are anionic ligands;
Y is a heteroatom selected from O or N;
$R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups;
n is 0, 1, or 2; and
Z is selected from hydrogen, hydrocarbyl, substituted hydrocarbyl, heteroatom-containing hydrocarbyl, substituted heteroatom-containing hydrocarbyl, and functional groups, wherein any combination of Y, Z, $R^5$, $R^6$, $R^7$, and $R^8$ can be linked to form one or more cyclic groups, and further wherein any combination of $X^1$, $X^2$, $L^1$, Y, Z, $R^5$, $R^6$, $R^7$, and $R^8$ may be attached to a support.

Examples of metal carbene olefin metathesis catalysts have the structure of formula (I)

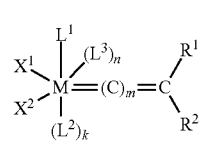

(I)

in which:
M is ruthenium;
n is 0;
m is 0;
k is 1;
$L^1$ and $L^2$ are trisubstituted phosphines independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);
$X^1$ and $X^2$ are chloride;
$R^1$ is hydrogen and $R^2$ is phenyl or —CH=C(CH$_3$)$_2$ or thienyl; or $R^1$ and $R^2$ are taken together to form 3-phenyl-1H-indene;
and formula (VII)

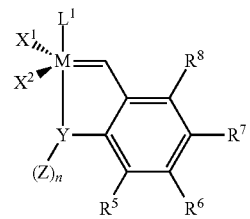

(VII)

wherein,
M is ruthenium;
$L^1$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$X^1$ and $X^2$ are chloride;

Y is oxygen;

$R^5$, $R^6$, $R^7$, and $R^8$ are each hydrogen;

n is 1; and

Z is isopropyl.

Examples of metal carbene olefin metathesis catalysts have the structure of formula (I)

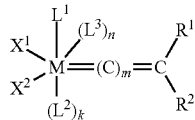

(I)

in which:

M is ruthenium;

n is 0;

m is 0;

k is 1;

$L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$L^2$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen and $R^2$ is phenyl or —CH═C(CH₃)₂ or thienyl; or $R^1$ and $R^2$ are taken together to form 3-phenyl-1H-indene;

and formula (VII)

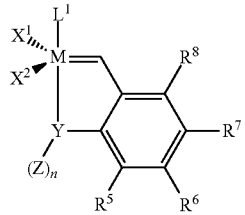

(VII)

wherein,

M is ruthenium;

$L^1$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$X^1$ and $X^2$ are chloride;

Y is oxygen;

$R^5$, $R^6$, $R^7$, and $R^8$ are each hydrogen;

n is 1; and

Z is isopropyl.

Examples of metal carbene olefin metathesis catalysts have the structure of formula (I)

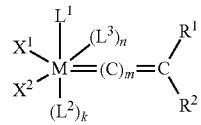

(I)

in which:

M is ruthenium;

n is 0;

m is 0;

k is 1;

$L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$L^2$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen and $R^2$ is phenyl or —CH═C(CH₃)₂ or thienyl; or $R^1$ and $R^2$ are taken together to form 3-phenyl-1H-indene;

and formula (VII)

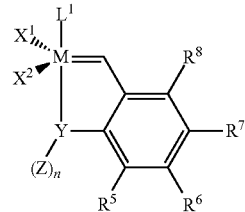

(VII)

wherein,

M is ruthenium;

$L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$X^1$ and $X^2$ are chloride;

Y is oxygen;

$R^5$, $R^6$, $R^7$, and $R^8$ are each hydrogen;

n is 1; and

Z is isopropyl.

Examples of metal carbene olefin metathesis catalysts have the structure of formula (I)

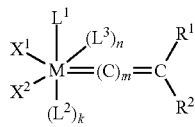

in which:
M is ruthenium;
n is 0;
m is 0;
k is 1;
L¹ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;
L² is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ is hydrogen and R² is phenyl or —CH=C(CH₃)₂ or thienyl; or R¹ and R² are taken together to form 3-phenyl-1H-indene.

Suitable supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups.

When utilized, suitable supports may be selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of a complex linked to the support.

The metathesis catalysts that are described infra may be utilized in olefin metathesis reactions according to techniques known in the art. The catalyst is typically added to the resin composition as a solid, a solution, or as a suspension. When the catalyst is added to the resin composition as a suspension, the catalyst is suspended in a dispersing carrier such as mineral oil, paraffin oil, soybean oil, tri-isopropylbenzene, or any hydrophobic liquid which has a sufficiently high viscosity so as to permit effective dispersion of the catalyst, and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of monomer to catalyst, the catalyst (the "monomer to catalyst ratio"), loading will generally be present in an amount that ranges from a low of about 10,000,000:1, 1,000,000:1, or 20,000:1, to a high of about 100,000:1 66,667:1, 40,000:1, 20,000:1, 10,000:1, 5,000:1, or 1,000:1.

Catalyst compositions of the invention comprise at least one metal carbene olefin metathesis catalyst. However, catalyst compositions of the invention may also comprise two or more metal carbene olefin metathesis catalysts.

In addition, any prior art metathesis catalyst (or two-component metathesis catalyst system) based on molybdenum or tungsten may also be used with the present invention.

Resin Compositions and Articles

Resin compositions according to the invention generally comprise at least one cyclic olefin composition. Additionally, resin compositions of the invention may comprise at least one cyclic olefin composition, where the resin composition is combined with a catalyst composition comprising at least one metal carbene olefin metathesis catalyst to form a ROMP composition. Additionally, the resin compositions according to the invention may comprise at least one cyclic olefin composition and at least one adhesion promoter. Additionally, the resin compositions according to the invention may comprise at least one cyclic olefin composition and at least one an adhesion promoter composition. Additionally, resin compositions of the invention may also comprise at least one cyclic olefin composition and at least one substrate material. Additionally, resin compositions of the invention may also comprise at least one cyclic olefin composition, at least one adhesion promoter, and at least one substrate material. Additionally, resin compositions according to the invention may also comprise at least one cyclic olefin composition, and at least one adhesion promoter, where the resin composition is combined with a catalyst composition comprising at least one metal carbene olefin metathesis catalyst to form a ROMP composition, and the resulting ROMP composition is applied to at least one substrate material. Additionally, resin compositions according to the invention may also comprise at least one cyclic olefin composition, and at least one adhesion promoter comprising at least one compound containing at least two isocyanate groups, where the resin composition is combined with a catalyst composition comprising at least one metal carbene olefin metathesis catalyst to form a ROMP composition, and the resulting ROMP composition is applied to at least one substrate material, wherein the substrate material may be functionalized substrate material, such as, for example, a heteroatom-functionalized substrate, such as, for example, an amino-functionalized substrate. Additionally, resin compositions according to the invention may also comprise at least one cyclic olefin composition, and at least one adhesion promoter comprising at least one compound containing at least two isocyanate groups, where the resin composition is combined with a catalyst composition comprising at least one metal carbene olefin metathesis catalyst, and the resulting resin composition is applied to at least one substrate material, such as, for example, a glass substrate material or carbon substrate material. In another embodiment, cyclic olefin resin, particularly ROMP, compositions according to the invention comprise at least one cyclic olefin composition, a catalyst composition comprising at least one metal carbene olefin metathesis catalyst, at least one adhesion promoter comprising at least one compound containing at least two isocyanate groups, and at least one heteroatom-functionalized substrate material.

In another embodiment, the resin compositions according to the invention may additionally comprise an adhesion promoter. Adhesion promoters for use in the present invention are disclosed in International Pat. App. No. PCT/US2012/042850, the contents of which are also incorporated herein by reference. The amounts of the adhesion promoter in the resin composition may vary over a wide range and may vary depending on the manufacturing operation or the particular end-use application. Generally, any level of adhesion promoter which produces a desired increase in mechanical properties is of particular interest. When formulated or combined with a resin composition, the concentration of the adhesion promoter typically ranges from 0.001-50 phr, particularly 0.05-10 phr, more particularly 0.1-10 phr, or even more particularly 0.5-4.0 phr.

In another embodiment, resin compositions according to the invention may additionally comprise an exogenous inhibitor. Exogenous inhibitors or "gel modification additives", for use in the present invention are disclosed in U.S. Pat. No. 5,939,504, the contents of which are also incorporated herein by reference. Non-limiting examples of exogenous inhibitors or "gel modification additives" include water, tetrahydrofuran (THF), 2-methyltetrahydrofuran (2-Me-THF), diethyl ether (($C_2H_5$)$_2$O), methyl-tert-butyl ether ($CH_3OC(CH_3)_3$), dimethoxyethane ($CH_3OCH_2CH_2OCH_3$), diglyme ($CH_3OCH_2OCH_2OCH_3$), trimethylphosphine ($PMe_3$), triethylphosphine ($PEt_3$), tributylphosphine ($PBu_3$), tri(ortho-tolyl)phosphine (P-o-tolyl$_3$), tri-tert-butylphosphine (P-tert-Bu$_3$), tricyclopentylphosphine (PCyclopentyl$_3$), tricyclohexylphosphine (PCy$_3$), triisopropylphosphine (P-i-Pr$_3$), trioctylphosphine (POct$_3$), triisobutylphosphine (P-i-Bu$_3$), triphenylphosphine (PPh$_3$), tri(pentafluorophenyl)phosphine (P($C_6F_5$)$_3$), methyldiphenylphosphine (PMePh$_2$), dimethylphenylphosphine (PMe$_2$Ph), diethylphenylphosphine (PEt$_2$Ph), trimethylphosphite (P(OMe)$_3$), triethylphosphite, (P(OEt)$_3$), triisopropylphosphite (P(O-i-Pr)$_3$), ethyl diphenylphosphinite (P(OEt)Ph$_2$), tributylphosphite (P(OBu)$_3$), triphenylphosphite (P(OPh)$_3$, diethylphenylphosphonite (P(OEt)$_2$Ph), and tribenzylphosphine (P(CH$_2$Ph)$_3$), 2-cyclohexenone, and triphenylphosphine oxide. Preferred exogenous inhibitors include triphenylphosphine, tricyclohexylphosphine, and tributylphosphine. The most preferred exogenous inhibitor is triphenylphosphine. When formulated or combined with a resin composition, the concentration of the exogenous inhibitor typically ranges from 0.001-10 phr, particularly 0.01-5 phr, more particularly 0.05-3 phr. Exogenous inhibitors may be added to the resin composition in the absence of solvent, or as organic solutions. A single exogenous inhibitor may be used, or a combination of two or more different exogenous inhibitors may be used.

In another embodiment, resin compositions according to the invention may additionally comprise a hydroperoxide gel modifier. Hydroperoxide gel modifiers for use in the present invention are disclosed in International Pat. App. No. PCT/US2012/042850, the contents of which are also incorporated herein by reference. Non-limiting examples of hydroperoxide gel modifiers include tert-butyl hydroperoxide, tert-amyl hydroperoxide, cumene hydroperoxide, diisopropyl benzene hydroperoxide, (2,5-dihydroperoxy)-2,5-dimethylhexane, cyclohexyl hydroperoxide, triphenylmethyl hydroperoxide, pinane hydroperoxide (e.g., Glidox® 500; LyondellBasell), and paramenthane hydroperoxide (e.g., Glidox® 300; LyondellBasell). More preferably, the hydroperoxides suitable for use include tert-butyl hydroperoxide and cumene hydroperoxide. Hydroperoxide gel-modification additives may be added to the reaction mixture in the absence of solvent, or as organic or aqueous solutions. A single hydroperoxide compound may be used as the gel-modification additive, or a combination of two or more different hydroperoxide compounds may be used. All concentrations of hydroperoxide which delay the onset of the gel-state of a particular metathesis polymerization. Advantageously, the use of hydroperoxides gel modifiers has been found to substantially maintain the properties of the cured polymer including peak exotherm temperature and mechanical properties. While not necessarily limited, the hydroperoxide concentration is advantageously between 0.01 and 1000 equivalents with respect to catalyst. In other embodiments the hydroperoxide concentration may be between 0.1 and 20 equivalents with respect to catalyst. Generally, higher concentrations of hydroperoxide will lead to longer pot life. Additionally, in other embodiments the hydroperoxide concentration may be between 0.05 and 100 equivalents with respect to catalyst. Additionally, in other embodiments the hydroperoxide concentration may be between 0.1 and 50 equivalents with respect to catalyst.

In another embodiment, resin compositions of the invention may additionally comprise at least one 5-alkenyl-2-norbornene as a pot life adjusting agent. 5-alkenyl-2-norbornenes for use in the present invention are disclosed in U.S. Pat. No. 5,204,427 and non-limiting examples include 5-vinylbicyclo[2.2.1]hepto-2-ene (5-vinyl-2-norbornene); 5-isopropenylbicyclo[2.2.1]hepto-2-ene (5-isopropenyl-2-norbornene); 5-vinyl-4-vinylbicyclo[2.2.1]hepto-2-ene (5-vinyl-4-vinyl-2-norbornene); 5-propenyl-bicyclo[2.2.1]hepto-2-ene (5-propenyl-2-norbornene); 5-butenyl-bicyclo[2.2.1]hepto-2-ene (5-butenyl-2-norbornene; 5-pentenyl-bicyclo[2.2.1]hepto-2-ene (5-pentenyl-2-norbornene); and their monomethyl, monochloro, and dichloro substituents, including the endo and exo isomers, and mixtures thereof. More preferred 5-alkenyl-2-norbornene(s) include 5-vinyl-2-norbornene, 5-isopropenyl-2-noborbornene, 5-propenyl-2-norbornene, and 5-butenyl-2-norbornene, including the endo and exo isomers, and mixtures thereof. The most preferred 5-alkenyl-2-norborne pot life adjusting agent is 5-vinyl-2-norbornene, including the endo and exo isomers, and mixtures thereof. 5-alkenyl-2-norbornene pot life adjusting agents are normally employed in the resin composition at levels of about 0.01 phr to 10 phr, more preferably at levels of about 0.1 phr to 5 phr, even more preferably at levels of about 0.1 phr to 3 phr. 5-alkenyl-2-norborne pot life adjusting agents may be added to the resin composition in the absence of solvent, or as organic solutions. A single 5-alkenyl-2-norborne pot life adjusting agent may be used as a pot life adjusting agent, or a combination of two or more different 5-alkenyl-2-norbornene pot life adjusting agents may be used.

Resin compositions of the invention may be optionally formulated with additives. Suitable additives include, but are not limited to, gel modifiers, hardness modulators, impact modifiers, elastomers, antioxidants, antiozonants, stabilizers, crosslinkers, fillers, binders, coupling agents, thixotropes, wetting agents, biocides, plasticizers, pigments, flame retardants, dyes, fibers and reinforcement materials, including sized reinforcements and substrates, such as those treated with finishes, coatings, coupling agents, film formers and/or lubricants. Furthermore, the amount of additives present in the resin compositions may vary depending on the particular type of additive used. The concentration of the additives in the resin compositions typically ranges from, for example, 0.001-85 percent by weight, particularly, from 0.1-75 percent by weight, or even more particularly, from 2-60 percent by weight.

Resin compositions of the invention may be optionally formulated with or without a crosslinker, for example, a crosslinker selected from dialkyl peroxides, diacyl peroxides, and peroxyacids.

Suitable impact modifiers or elastomers include without limitation natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, styrene-ethylene/butylene-styrene copolymer, styrene-ethylene/propylene-styrene copolymer, ethylene-propylene-diene terpolymers, ethylene-vinyl acetate, and nitrile rubbers. Preferred impact modifiers or elastomers are polybutadiene Diene 55AC 10 (Firestone), polybutadiene Diene 55AM5 (Firestone), EPDM Royalene 301T, EPDM Buna T9650 (Bayer), styrene-ethylene/butylene-styrene copolymer Kraton G1651H, Polysar Butyl 301 (Bayer), polybutadiene Taktene 710 (Bayer), styrene-ethylene/butylene-styrene Kraton G1726M, Ethylene-Octene Engage 8150 (DuPont-Dow), styrene-butadiene Kraton D1184, EPDM Nordel 1070 (DuPont-Dow), and polyisobutylene Vistanex MML-140 (Exxon). Such materials are normally employed in the resin composition at levels of about 0.10 phr to 10 phr, but more preferably at levels of about 0.1 phr to 5 phr. Various polar impact modifiers or elastomers can also be used.

Antioxidants and antiozonants include any antioxidant or antiozonant used in the rubber or plastics industry. An "Index of Commercial Antioxidants and Antiozonants, Fourth Edition" is available from Goodyear Chemicals, The Goodyear Tire and Rubber Company, Akron, Ohio 44316. Suitable stabilizers (i.e., antioxidants or antiozonants) include without limitation: 2,6-di-tert-butyl-4-methylphenol (BHT); styrenated phenol, such as Wingstay® S (Goodyear); 2- and 3-tert-butyl-4-methoxyphenol; alkylated hindered phenols, such as Wingstay C (Goodyear); 4-hydroxymethyl-2,6-di-tert-butylphenol; 2,6-di-tert-butyl-4-sec-butylphenol; 2,2'-methylenebis(4-methyl-6-tert-butylphenol); 2,2'-methylenebis(4-ethyl-6-tert-butylphenol); 4,4'-methylenebis(2,6-di-tert-butylphenol); miscellaneous bisphenols, such as Cyanox® 53 (Cytec Industries Inc.) and Permanax WSO; 2,2'-ethylidenebis(4,6-di-tert-butylphenol); 2,2'-methylenebis(4-methyl-6-(1-methylcyclohexyl)phenol); 4,4'-butylidenebis(6-tert-butyl-3-methylphenol); polybutylated Bisphenol A; 4,4'-thiobis(6-tert-butyl-3-methylphenol); 4,4'-methylenebis(2,6-dimethylphenol); 1,1'-thiobis(2-naphthol); methylene bridged polyaklylphenol, such as Ethyl antioxidant 738; 2,2'-thiobis(4-methyl-6-tert-butylphenol); 2,2'-isobutylidenebis(4,6-dimethylphenol); 2,2'-methylenebis(4-methyl-6-cyclohexylphenol); butylated reaction product of p-cresol and dicyclopentadiene, such as Wingstay L; tetrakis(methylene-3,5-di-tert-butyl-4-hydroxyhydrocinnamate)methane, i.e., Irganox® 1010 (BASF); 1,3,5-trimethyl-2,4,6-tris(3,5-di-tert-butyl-4-hydroxybenzyl)benzene, e.g., Ethanox® 330 (Albemarle Corporation); 4,4'-methylenebis (2,6-di-tertiary-butylphenol), e.g., Ethanox 4702 or Ethanox 4710; 1,3,5-tris(3,5-di-tert-butyl-4-hydroxybenzyl)isocyanurate, i.e., Good-rite® 3114 (Emerald Performance Materials), 2,5-di-tert-amylhydroquinone, tert-butylhydroquinone, tris(nonylphenylphosphite), bis(2,4-di-tert-butyl)pentaerythritol) diphosphite, distearyl pentaerythritol diphosphite, phosphited phenols and bisphenols, such as Naugard® 492 (Chemtura Corporation), phosphite/phenolic antioxidant blends, such as Irganox B215; di-n-octadecyl(3,5-di-tert-butyl-4-hydroxybenzyl)phosphonate, such as Irganox 1093; 1,6-hexamethylene bis(3-(3,5-di-tert-butyl-4-hydroxyphenylpropionate), such as Irganox 259, and octadecyl-3,5-di-tert-butyl-4-hydroxyhydrocinnamate, i.e., Irganox 1076, tetrakis(2,4-di-tert-butylphenyl)4,4'-biphenylylenediphosphonite, diphenylamine, and 4,4'-diemthoxydiphenylamine. Such materials are normally employed in the resin composition at levels of about 0.10 phr to 10 phr, but more preferably at levels of about 0.1 phr to 5 phr.

Suitable reinforcing materials include those that add to the strength or stiffness of a polymer composite when incorporated with the polymer. Reinforcing materials can be in the form of filaments, fibers, rovings, mats, weaves, fabrics, knitted material, cloth, or other known structures. Suitable reinforcement materials include glass fibers and fabrics, carbon fibers and fabrics, aramid fibers and fabrics, polyolefin fibers or fabrics (including ultrahigh molecular weight polyethylene fabrics such as those produced by Honeywell under the Spectra® trade name), and polyoxazole fibers or fabrics (such as those produced by the Toyobo Corporation under the Zylon® trade name). Reinforcing materials containing surface finishes, sizings, or coatings are particularly suitable for the described invention including Ahlstrom glass roving (R338-2400), Johns Manville glass roving (Star ROV®-086), Owens Corning rovings (OCV 366-AG-207, R25H-X14-2400, SE1200-207, SE1500-2400, SE2350-250), PPG glass rovings (Hybon® 2002, Hybon® 2026), Toho Tenax® carbon fiber tow (HTR-40), and Zoltek carbon fiber tow (Panex® 35). Furthermore, any fabrics prepared using reinforcing materials containing surface finishes, sizings or coatings are suitable for the invention. Advantageously, the invention does not require the expensive process of removing of surface finishes, sizings, or coatings from the reinforcing materials. Additionally, glass fibers or fabrics may include without limitation A-glass, E-glass or S-glass, S-2 glass, C-glass, R-glass, ECR-glass, M-glass, D-glass, and quartz, and silica/quartz. Preferred glass fiber reinforcements are those with finishes formulated for use with epoxy, vinyl ester, and/or polyurethane resins. When formulated for use with a combination of these resin types, the reinforcements are sometimes described as "multi-compatible." Such reinforcements are generally treated during their manufacture with organosilane coupling agents comprising vinyl, amino, glycidoxy, or methacryloxy functional groups (or various combinations thereof) and are coated with a finish to protect the fiber surface and facilitate handling and processing (e.g., spooling and weaving). Finishes typically comprise a mixture of chemical and polymeric compounds such as film formers, surfactants, and lubricants. Especially preferred glass reinforcements are those containing some amount of amino-functionalized silane coupling agent. Especially preferred finishes are those comprising and epoxy-based and/or polyurethane-based film formers. Examples of preferred glass-fiber reinforcements are those based on Hybon® 2026, 2002, and 2001 (PPG) multi-compatible rovings; Ahlstrom R338 epoxysilane-sized rovings; StarRov® 086 (Johns Manville) soft silane sized multi-compatible rovings; OCV™ 366, SE 1200, and R25H (Owens Corning) multi-compatible rovings; OCV™ SE 1500 and 2350 (Owens Corning) epoxy-compatible rovings; and Jushi Group multi-compatible glass rovings (752 type, 396 type, 312 type, 386 type). Additional suitable polymer fibers and fabrics may include without limitation one or more of polyester, polyamide (for example, NYLON polamide available from E.I. DuPont, aromatic polyamide (such as KEVLAR aromatic polyamide available from E.I. DuPont, or P84 aromatic polyamide available from Lenzing Aktiengesellschaft), polyimide (for example KAPTON polyimide available from E.I. DuPont, polyethylene (for example, DYNEEMA polyethylene from Toyobo Co., Ltd.). Additional suitable carbon fibers may include without limitation AS2C, AS4, AS4C, AS4D, AS7, IM6, IM7, IM9, and PV42/850 from Hexcel Corporation; TORAYCA T300, T300J, T400H, T600S, T700S, T700G, T800H, T800S, T1000G, M35J, M40J, M46J, M50J, M55J, M60J, M30S, M30G and M40 from Toray Industries, Inc.; HTS12K/24K, G30-500 3k/6K/12K, G30-500 12K, G30-700 12K, G30-7000 24K F402, G40-800 24K, STS 24K, HTR 40 F22 24K 1550tex from Toho Tenax, Inc.; 34-700, 34-700WD, 34-600, 34-600WD, and 34-600 unsized from Grafil Inc.; T-300, T-650/35, T-300C, and T-650/35C from Cytec Industries. Additionally suitable carbon fibers may include without limitation AKSACA (A42/D011), AKSACA (A42/D012), Blue Star Starafil (10253512-90), Blue Star Starafil (10254061-130), SGL Carbon (C30 T050 1.80), SGL Carbon (C50 T024 1.82), Grafil (347R1200U), Grafil (THR 6014A), Grafil (THR 6014K), Hexcel Carbon (AS4C/EXP 12K), Mitsubishi (Pyrofil TR 50S 12L AF), Mitsubishi (Pyrofil TR 50S 12L AF), Toho Tenax (T700SC 12000-50C), Toray (T700SC 12000-90C), Zoltek (Panex 35 50K, sizing 11), Zoltek (Panex 35 50K, sizing 13). Additional suitable carbon fabrics may include without limitation Carbon fabrics by Vectorply (C-L 1800) and Zoltek (Panex 35 UD Fabic-PX35UD0500-1220). Additionally suitable glass fabrics may include without limitation glass fabrics as supplied by Vectorply (E-LT 3500-10) based on PPG Hybon® 2026; Saertex (U14EU970-01190-T2525-125000) based on PPG Hybon® 2002; Chongqing Polycomp Intemation Corp. (CPIC® Fiberglass) (EKU 1150(0)/50-600); and Owens Corning (L1020/07A06 Xweft 200tex).

Other suitable fillers include, for example, metallic density modulators, microparticulate density modulators, such as, for example, microspheres, and macroparticulate density modulators, such as, for example, glass or ceramic beads. Metallic density modulators include, but are not limited to, powdered, sintered, shaved, flaked, filed, particulated, or granulated metals, metal oxides, metal nitrides, and/or metal carbides, and the like. Preferred metallic density modulators include, among others, tungsten, tungsten carbide, aluminum, titanium, iron, lead, silicon oxide, aluminum oxide, boron carbide, and silicon carbide. Microparticulate density modulators include, but are not limited to, glass, metal, thermoplastic (either expandable or pre-expanded) or thermoset, and/or ceramic/silicate microspheres. Macroparticulate density modulators include, but are not limited to, glass, plastic, or ceramic beads; metal rods, chunks, pieces, or shot; hollow glass, ceramic, plastic, or metallic spheres, balls, or tubes; and the like.

The invention is also directed to articles manufactured from a resin composition comprising at least one cyclic olefin composition, and a catalyst composition comprising at least one metal carbene olefin metathesis catalyst. Additionally, the invention is directed to articles manufactured from a resin composition comprising at least one cyclic olefin composition, a catalyst composition comprising at least one metal carbene olefin metathesis catalyst, and a substrate material. Additionally, the invention is directed to articles manufactured from a resin composition comprising at least one cyclic olefin composition, at least one adhesion promoter, a catalyst composition comprising at least one metal carbene olefin metathesis catalyst, and a substrate material.

Additionally, the invention is directed to articles manufactured from a resin composition comprising at least one cyclic olefin composition, at least one adhesion promoter comprising at least one compound containing at least two isocyanate groups, where the resin composition is combined with a catalyst composition comprising at least one metal carbene olefin metathesis catalyst to form a ROMP composition, and the resulting ROMP composition is applied to at least one substrate, which may be, for example, a functionalized substrate, such as, for example, a heteroatom-functionalized substrate, such as, for example, an amino-functionalized substrate.

Articles may include, but are not limited to, those formed by standard manufacturing techniques including casting, centrifugal casting, pultrusion, molding, rotational molding, open molding, reaction injection molding (RIM), resin transfer molding (RTM), pouring, vacuum impregnation, surface coating, filament winding and other methods known to be useful for production of polymer articles and/or polymer composite articles. Furthermore, the compositions and articles of manufacture of the invention are not limited to a single polymer-surface interface but include also multilayers and laminates containing multiple polymer-surface interfaces. The invention is also suitable for manufacture of articles by the infusion of the resin into a porous material. Such porous materials include but are not limited to wood, cement, concrete, open-cell and reticulated foams and sponges, papers, cardboards, felts, ropes or braids of natural or synthetic fibers, and various sintered materials. Additionally, other manufacturing techniques include without limitation cell casting, dip casting, continuous casting, embedding, potting, encapsulation, film casting or solvent casting, gated casting, mold casting, slush casting, extrusion, mechanical foaming, chemical foaming, physical foaming, compression molding or matched die molding, spaying, spray up, Vacuum Assisted Resin Transfer Molding (VARTM), Seeman's Composite Resin Infusion Molding Process (SCRIMP), blow molding, in mold coating, in-mold painting or injection, vacuum forming, Reinforced Reaction Injection Molding (RRIM), Structural Reaction Injection Molding (SRIM), thermal expansion transfer molding (TERM), resin injection recirculation molding (RICM), controlled atmospheric pressure resin infusion (CAPRI), hand-layup. For manufacturing techniques requiring the use of a RIM or impingement style mixhead, including without limitation RIM, SRIM, and RRIM, articles of manufacture may be molded using a single mixhead or a plurality of mixheads as well as a plurality of material injection streams (e.g., two resin streams and one catalyst stream). As the invention allows for increasingly faster cycle times and increasingly higher mold temperatures using any of the aforementioned manufacturing techniques, particularly mold temperatures above 90° C., it may become necessary to mold ROMP compositions of the invention under high pressures or under vacuum to prevent defects caused by mixing issues and/or entrapped gases.

Furthermore, the present invention also allows for the making of articles of manufacture of any configuration, weight, size, thickness, or geometric shape. Examples of articles of manufacture include without limitation any molded or shaped article for use as an aerospace component, a marine component, an automotive component, a sporting goods component, an electrical component, and industrial component, medical component, dental component, or military component. In one embodiment an article may be a turbine component used on aircraft or general power generation. In one embodiment, turbine components may include without limitation one or more of an inlet, pylon, pylon fairing, an acoustic panel, a thrust reverser panel, a fan blade, a fan containment case, a bypass duct, an aerodynamic cowl, or an airfoil component. In one embodiment, an article may be a turbine blade component or may be a turbine blade. In one embodiment, an article may be a wind rotor blade, tower, spar cap, or nacelle for wind turbines. In one embodiment, an article may be an airframe component. Examples of aerospace components may include without limitation one or more of fuselage skin, wing, fairing, doors, access panel, aerodynamic control surface, or stiffener. In one embodiment an article may be an automotive component. Examples of automotive components may include without limitation one or more of body panel, fender, spoiler, truck bed, protective plate, hood, longitudinal rail, pillar, or door. Examples of industrial components may include without limitation one or more of risers platforms, impact protection structures for oil and gas; bridges, pipes, pressure vessels, power poles, coils, containers, tanks, liners, containment vessels, articles for application in corrosive environments (e.g., chlor-alkali, caustic, acidic, brine, etc.), centralizers (e.g. oilfield centralizer), electrolytic cell covers, reinforcement structures for concrete architectures and roads, or radiators. Examples of electrical components may include without limitation one or more wound articles, such as coils or electric motors, or insulating devices. In one embodiment, an article may be an eddy-current shielding component of a magnetic resonance imaging system or shielding component for any electromagnetic radiation. In one embodiment, an article may be a military component including without limitation ballistics resistant armor for personnel or vehicles, or ballistics resistant structures for protecting personnel or equipment. In one embodiment, an article may be a sporting goods component including without limitation an arrow shaft, a tennis racket frame, a hockey stick, compound bow limbs, or a golf club shaft. In one embodiment, an article may be an object used in offshore applications, where the object is at least partially coated with a ROMP composition of the invention, where the object includes but is not limited to pipes, pipelines, pipe fittings, hoses, hose fittings, tanks, containers, drums, manifolds, risers, field joints, configurations designated as Christmas trees (oil field Christmas tree, subsea Christmas tree), jumpers, spool pieces, configurations designated as pipeline end termination (PLET), configurations designated as pipeline end manifolds (PLEM), robotic parts, devices and vehicles used in sub-sea applications, configurations designated as subsea dog houses, and other sub-sea architectures and equipment.

Resin compositions according to the invention may further comprise a sizing composition, or be used to provide improved adhesion to substrate materials that are sized with certain commercial silanes commonly used in the industry. As is known in the art, glass fibers are typically treated with a chemical solution (e.g., a sizing composition) soon after their formation to reinforce the glass fibers and protect the strands' mechanical integrity during processing and composite manufacture. Sizing treatments compatible with olefin metathesis catalysts and polydicyclopentadiene composites have been described in U.S. Pat. Nos. 6,890,650 and 6,436,476, the disclosures of both of which are incorporated herein by reference. However, these disclosures are based on the use of specialty silane treatments that are not commonly used in industrial glass manufacture. By comparison, the current invention may provide improved mechanical properties for polymer-glass composites that are sized with silanes commonly used in the industry.

Glass sizing formulations typically comprise at least one film former (typically a film forming polymer), at least one silane, and at least one lubricant. Any components of a sizing formulation that do not interfere with or substantially decrease the effectiveness of the metathesis catalyst or olefin polymerization reaction are considered to be compatible with the current invention and may generally be used herein.

Film formers that are compatible with metathesis catalysts include epoxies, polyesters, polyurethanes, polyolefins, and/or polyvinyl acetates. Other common film formers that do not adversely affect the performance of the olefin metathesis catalyst may also be used. Film formers are typically used as nonionic, aqueous emulsions. More than one film former may be used in a given sizing formulation, to achieve a desired balance of glass processability and composite mechanical properties.

More particularly, the film former may comprise a low molecular weight epoxy emulsion, defined as an epoxy monomer or oligomer with an average molecular weight per epoxide group (EEW) of less than 500, and/or a high molecular weight epoxy emulsion, defined as an epoxy monomer or oligomer with an average molecular weight per epoxide group (EEW) of greater than 500. Examples of suitable low molecular weight products include aqueous epoxy emulsions produced by Franklin International, including Franklin K8-0203 (EEW 190) and Franklin E-102 (EEW 225-275). Other examples of low molecular weight epoxy emulsions are available from Hexion, including EPI-REZ™ 3510-W-60 (EEW 185-215), and EPI-REZ™ 3515-W-60 (EEW 225-275). Further examples of low molecular weight epoxy emulsions are available from COIM, including Filco 309 (EEW 270) and Filco 306 (EEW 330). Further examples of low molecular weight epoxy emulsions are available from DSM, including Neoxil® 965 (EEW 220-280) and Neoxil® 4555 (EEW 220-260). Examples of suitable high molecular weight epoxy emulsion products include epoxy emulsions produced by Hexion, including EPI-REZ™ 3522-W-60 (EEW 615-715).

Aqueous emulsions of modified epoxies, polyesters, and polyurethanes may also be used in the film former. Examples of suitable modified epoxy products include emulsions produced by DSM, including Neoxil® 2626 (a plasticized epoxy with an EEW of 500-620), Neoxil® 962/D (an epoxy-ester with an EEW of 470-550), Neoxil® 3613 (an epoxy-ester with an EEW of 500-800), Neoxil® 5716 (an epoxy-novolac with an EEW of 210-290), Neoxil® 0035 (a plasticized epoxy-ester with an EEW of 2500), and Neoxil® 729 (a lubricated epoxy with an EEW of 200-800). Further examples of modified epoxy emulsions are available from COIM, including Filco 339 (an unsaturated polyester-epoxy with an EEW of 2000) and Filco 362 (an epoxy-ester with an EEW of 530). Examples of suitable polyester products include emulsions produced by DSM, including Neoxil® 954/D, Neoxil® 2635, and Neoxil® 4759 (unsaturated bisphenolic polyesters). Additional suitable products from DSM include Neoxil® 9166 and Neoxil® 968/60 (adipate polyesters). Further examples of suitable products include emulsions produced by COIM, including Filco 354/N (unsaturated bisphenolic polyester), Filco 350 (unsaturated polyester), and Filco 368 (saturated polyester). Examples of suitable polyurethane products include emulsions produced by Bayer Material Science, including Baybond® 330 and Baybond® 401.

The film former may also comprise polyolefins or polyolefin-acrylic copolymers, polyvinylacetates, modified polyvinylacetates, or polyolefin-acetate copolymers. Suitable polyolefins include, but are not limited to, polyethylenes, polypropylenes, polybutylenes, and copolymers thereof, and the polyolefins may be oxidized, maleated, or otherwise treated for effective film former use. Examples of suitable products include emulsions produced by Michelman, including Michem® Emulsion 91735, Michem® Emulsion 35160, Michem® Emulsion 42540, Michem® Emulsion 69230, Michem® Emulsion 34040M1, Michem® Prime 4983R, and Michem® Prime 4982SC. Examples of suitable products include emulsions produced by HB Fuller, including PD 708H, PD 707, and PD 0166. Additional suitable products include emulsions produced by Franklin International, including Duracet® 637. Additional suitable products include emulsions produced by Celanese, including Vinamul® 8823 (plasticized polyvinylacetate), Dur-O-Set® E-200 (ethylene-vinyl acetate copolymer), Dur-O-Set® TX840 (ethylene-vinyl acetate copolymer), and Resyn® 1971 (epoxy-modified polyvinylacetate).

While not limited thereto, preferred film formers include low- and high-molecular weight epoxies, saturated and unsaturated polyesters, and polyolefins, such as Franklin K80-203, Franklin E-102, Hexion 3510-W-60, Hexion 3515-W-60, and Michelman 35160.

Nonionic lubricants may also be added to the sizing composition. Suitable nonionic lubricants that are compatible with ROMP compositions include esters of polyethylene glycols and block copolymers of ethylene oxide and propylene oxide. More than one nonionic lubricant may be used in a given sizing formulation if desired, e.g., to achieve a desired balance of glass processability and composite mechanical properties.

Suitable lubricants may contain polyethylene glycol (PEG) units with an average molecular weight between 200 and 2000, preferably between 200-600. These PEG units can be esterified with one or more fatty acids, including oleate, tallate, laurate, stearate, and others. Particularly preferred lubricants include PEG 400 dilaurate, PEG 600 dilaurate, PEG 400 distearate, PEG 600 distearate, PEG 400 dioleate, and PEG 600 dioleate. Examples of suitable products include compounds produced by BASF, including MAPEG® 400 DO, MAPEG® 400 DOT, MAPEG® 600 DO, MAPEG® 600 DOT, and MAPEG® 600 DS. Additional suitable products include compounds produced by Zschimmer & Schwarz, including Mulsifan 200 DO, Mulsifan 400 DO, Mulsifan 600 DO, Mulsifan 200 DL, Mulsifan 400 DL, Mulsifan 600 DL, Mulsifan 200 DS, Mulsifan 400 DS, and Mulsifan 600 DS. Additional suitable products include compounds produced by Cognis, including Agnique® PEG 300 DO, Agnique® PEG 400 DO, and Agnique® PEG 600 DO.

Suitable nonionic lubricants also include block copolymers of ethylene oxide and propylene oxide. Examples of suitable products include compounds produced by BASF, including Pluronic® L62, Pluronic® L101, Pluronic® P103, and Pluronic® P105.

Cationic lubricants may also be added to the sizing composition. Cationic lubricants that are compatible with ROMP include modified polyethyleneimines, such as Emery 6760L produced by Pulcra Chemicals.

Silane coupling agent may optionally be added to the sizing composition, non-limiting examples including, methacrylate, acrylate, amino, or epoxy functionalized silanes along with alkyl, alkenyl, and norbornenyl silanes.

Optionally, the sizing composition may contain one or more additives for modifying the pH of the sizing resin. One preferred pH modifier is acetic acid.

The sizing composition may optionally contain other additives useful in glass sizing compositions. Such additives may include emulsifiers, defoamers, cosolvents, biocides, antioxidants, and additives designed to improve the effectiveness of the sizing composition. The sizing composition can be prepared by any method and applied to substrate materials for use herein, such as glass fibers or fabric, by any technique or method.

In a preferred embodiment, the metathesis reactions disclosed herein are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions disclosed herein may also be carried out in an oxygen-containing and/or a water-containing atmosphere, and in one embodiment, the reactions are carried out under ambient conditions. The presence of oxygen or water in the reaction may, however, necessitate the use of higher catalyst loadings as compared with reactions performed under an inert atmosphere. Where the vapor pressure of the reactants allows, the reactions disclosed herein may also be carried out under reduced pressure.

The reactions disclosed herein may be carried out in a solvent, and any solvent that is inert towards cross-metathesis may be employed. Generally, solvents that may be used in the metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethyl ether, pentane, methanol, ethanol, water, or mixtures thereof. In a preferred embodiment, the reactions disclosed herein are carried out neat, i.e., without the use of a solvent.

It will be appreciated that the temperature at which a metathesis reaction according to methods disclosed herein is conducted can be adjusted as needed over a wide range of temperatures. With highly active metathesis catalysts, olefin metathesis may occur at temperatures as low as −78° C. With increasingly latent catalysts, olefin metathesis may not be observed until temperatures of −40° C., −10° C., 0° C., 10° C., 20° C., 25° C., 35° C., 50° C., 70° C., 100° C., or 150° C. In a preferred embodiment, the reactions are carried out at a temperature of at least about 35° C., and in another preferred embodiment, the reactions are carried out at a temperature of at least about 50° C. In certain embodiments, a mold or preform may be filled with resin and catalyst at a temperature near room temperature (e.g., about 10-45° C., or preferably 15-40° C., or more preferably 20-35° C.) and then heated over a period time to a higher temperature (e.g., about 50-200° C., or preferably 70-150° C., or more preferably 90-120° C.) to allow polymerization to complete more quickly. In certain embodiments, a mold or preform may be preheated to a temperature considerably above room temperature (e.g., about 50-250° C., or about 50-200° C., or about 50-150° C., or about 50-100° C., or about 100-150° C., or about 150-200° C.) and then filled quickly with resin and catalyst to allow for fast cycle times.

It is to be understood that while the invention has been described in conjunction with specific embodiments thereof, the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius (° C.), pressure is at or near atmospheric, viscosity is in centipoise (cP). Additives added to the cyclic olefin compositions to form resin compositions are reported as ppm, which is defined as the weight in grams of additive per million grams of cyclic olefin composition, or as phr, which is defined as the weight in grams of the additive per hundred grams of cyclic olefin composition.

The following examples are to be considered as not being limiting of the invention as described herein, and are instead provided as representative examples of the compositions of the invention, methods for their use, and articles made from such compositions and methods.

Examples

Materials and Methods

All glassware was oven dried and reactions were performed under ambient conditions unless otherwise noted. All solvents and reagents were purchased from commercial suppliers and used as received unless otherwise noted. All cyclic olefin compositions were degassed a minimum of 20 minutes under vacuum to remove cyclopentadiene (CPD) unless otherwise noted. Weight percent of dicyclopentadiene (DCPD), tricyclopentadiene (TCPD), and tetracyclopentadiene (TeCPD) present in the degassed cyclic olefin compositions were determined from the percent area values obtained by gas chromatography (GC).

DCPD (Ultrene® 99) was obtained from Cymetech Corporation. A representative lot of Ultrene® 99 comprised DCPD (99.83 weight percent) and TCPD (0.17 weight percent) as measured by GC. A modified DCPD base resin (DCPD-HT) containing 20-25% TCPD (and small amounts of higher CPD homologs) was prepared by heat treatment of Ultrene® 99 generally as described in U.S. Pat. No. 4,899,005. A representative lot of DCPD-HT prepared in this fashion comprised DCPD (73.98 weight percent), TCPD (23.51 weight percent), and TeCPD (2.51 weight percent).

TCPD was prepared from DCPD-HT by removing DCPD and other low molecular weight, low boiling hydrocarbons under vacuum to give a composition comprising approximately 80% by weight TCPD, which was further subjected to high vacuum distillation to give the desired product as a white, waxy solid when cooled to room temperature. A representative lot of TCPD (>99% purity) prepared in this fashion comprised DCPD (0.11 weight percent), TCPD (99.72 weight percent), and tetracyclopentadiene (0.17 weight percent) as measured by GC. A second representative lot of TCPD prepared in this fashion comprised DCPD (2.93 weight percent), TCPD (97.03 weight percent), and TeCPD (0.04 weight percent).

Liquid MDI (50/50 mixture of 4,4'-MDI and 2,4'-MDI) was used as received from Bayer Material Science (Mondur® MLQ) and was used where indicated. Ethanox® 4702 antioxidant (4,4'-methylenebis(2,6-di-tertiary-butylphenol), Albemarle Corporation) was used where indicated. Crystal Plus 70FG mineral oil, containing 2 phr Cab-o-sil TS610, was used to prepare the catalyst suspensions. Triphenylphosphine (TPP) was used as received from Arkema. 5-Vinyl-2-norbornene (>99%) was used as received from JX Nippon Chemical Texas Inc. A metal carbene olefin metathesis catalyst tricyclohexylphosphine[1,3-bis(2,4,6-trimethylphenyl)imidazol-2-ylidene][2-thienylmethylene]ruthenium(II) dichloride) (catMETium® RF2 Evonik Industries; CAS No. 1190427-49-6) was purchased from Strem Chemicals Inc.

Metal carbene olefin metathesis catalysts were prepared by standard methods and include [1,3-bis-(2,4,6-trimethylphenyl)-2-imidazolidinylidene]dichloro(3-methyl-2-butenylidene) (tricyclohexylphosphine) ruthenium(II) (C827); 1,3-bis-(2,4,6-trimethylphenyl)-2-imidazolidinylidene]dichloro(benzylidene) (tricyclohexylphosphine)ruthenium(II) (C848); [1,3-bis-(2,4,6-trimethylphenyl)-2-imidazolidinylidene]dichloro(phenylindenylidene)(diethylphenylphosphine) ruthenium(II) (C835), [1,3-bis-(2,4,6-trimethylphenyl)-2-imidazolidinylidene]dichloro (phenylindenylidene) (tricyclohexylphosphine) ruthenium(II) (C949); and ruthenium (II) dichloro (3-methyl-2-butenylidene) bis(tricyclohexylphosphine) (C801)

Cyclic Olefin Composition (A): Ultrene® 99 DCPD was heat treated as generally described in U.S. Pat. No. 4,899,005 until TCPD content reached 10-14% (as determined by GC). DCPD and other low molecular weight, low boiling hydrocarbons were removed under vacuum to give a composition comprising 54-56% by weight TCPD. The desired TCPD/tetracyclopentadiene ratio was adjusted by adding TCPD (>99% purity) and Ultrene® 99 DCPD to give cyclic olefin composition (A) as a colorless, transparent homogenous liquid at room temperature. Degassed cyclic olefin composition (A) comprised DCPD (42.99 weight percent), TCPD (55.14 weight percent), and tetracyclopentadiene (1.87 weight percent) as measured by GC.

Cyclic Olefin Composition (B): Ultrene® 99 DCPD was heat treated as generally described in U.S. Pat. No. 4,899,005 until TCPD content reached 10-14% (as determined by GC). DCPD and other low molecular weight, low boiling hydrocarbons were removed under vacuum to give a composition comprising 66-69% by weight TCPD. The desired TCPD/tetracyclopentadiene ratio was adjusted by adding TCPD (>99% purity) and Ultrene® 99 DCPD to give cyclic olefin composition (B) as a colorless, transparent homogenous liquid at room temperature. Degassed cyclic olefin composition (B) comprised DCPD (29.78 weight percent), TCPD (67.57 weight percent), and tetracyclopentadiene (2.65 weight percent) as measured by GC.

Cyclic Olefin Composition (C): Ultrene® 99 DCPD was heat treated as generally described in U.S. Pat. No. 4,899,005 until TCPD content reached 10-14% (as determined by GC). DCPD and other low molecular weight, low boiling hydrocarbons were removed under vacuum to give a composition comprising 54-56% by weight TCPD. The desired TCPD/TeCPD ratio was adjusted by adding TCPD (>99% purity) and Ultrene® 99 DCPD to give cyclic olefin composition (C) as a colorless, transparent homogenous liquid at room temperature. Degassed cyclic olefin composition (C) comprised DCPD (37.17 weight percent), TCPD (59.28 weight percent), and TeCPD (3.55 weight percent) as measured by GC.

Cyclic Olefin Composition (D): Ultrene® 99 DCPD was melted and combined with a representative lot of TCPD comprising DCPD (2.93 weight percent), TCPD (97.03 weight percent), and TeCPD (0.04 weight percent). The resulting degassed cyclic olefin composition (D) comprised DCPD (90.04 weight percent) and TCPD (9.96 weight percent) as measured by GC.

Cyclic Olefin Composition (E): Ultrene® 99 DCPD was melted and combined with a representative lot of TCPD comprising DCPD (2.93 weight percent), TCPD (97.03 weight percent), and TeCPD (0.04 weight percent). The resulting degassed cyclic olefin composition (E) comprised DCPD (79.88 weight percent) and TCPD (20.12 weight percent) as measured by GC.

Cyclic Olefin Composition (F): A representative lot of DCPD-HT comprising DCPD (73.98 weight percent), TCPD (23.51 weight percent), and TeCPD (2.51 weight percent) was combined with a representative lot of TCPD comprising DCPD (2.93 weight percent), TCPD (97.03 weight percent), and TeCPD (0.04 weight percent). The resulting degassed cyclic olefin composition (F) comprised DCPD (66.00 weight percent), TCPD (31.54 weight percent), and TeCPD (2.46 weight percent) as measured by GC.

Cyclic Olefin Composition (G): A representative lot of DCPD-HT comprising DCPD (73.98 weight percent), TCPD (23.51 weight percent), and TeCPD (2.51 weight percent) was combined with a representative lot of TCPD comprising DCPD (2.93 weight percent), TCPD (97.03 weight percent), and TeCPD (0.04 weight percent). The resulting degassed cyclic olefin composition (G) comprised DCPD (58.58 weight percent), TCPD (39.44 weight percent), and TeCPD (1.98 weight percent) as measured by GC.

Catalyst Composition (A): C827 was suspended in mineral oil (Crystal Plus 500 FG) containing 2 phr Cab-o-sil TS610. Catalyst composition (A) was prepared so as to have a monomer to catalyst ratio of 45,000:1 at 2 grams of catalyst suspension per 100 grams of DCPD monomer.

Catalyst Composition (B): C848 was suspended in mineral oil (Crystal Plus 500 FG) containing 2 phr Cab-o-sil TS610. Catalyst composition (B) was prepared so as to have a monomer to catalyst ratio of 90,000:1 at 2 grams of catalyst suspension per 100 grams of DCPD monomer.

Catalyst Composition (C): C827 and C835 were suspended in mineral oil (Crystal Plus 500 FG) containing 2 phr Cab-o-sil TS610. Catalyst composition (C) was prepared so as to have a monomer to catalyst ratio of 45,000:1 for C827 and 150,000:1 for C835 at 2 grams of catalyst suspension per 100 grams of DCPD monomer.

Catalyst Composition (D): C949 was suspended in mineral oil (Crystal Plus 500 FG) containing 2 phr Cab-o-sil TS610. Catalyst composition (D) was prepared so as to have a monomer to catalyst ratio of 30,000:1 for C949 at 2 grams of catalyst suspension per 100 grams of DCPD monomer.

Catalyst Composition (E): C827 and C848 were suspended in mineral oil (Crystal Plus 500 FG) containing 2 phr Cab-o-sil TS610. Catalyst composition (E) was prepared so as to have a monomer to catalyst ratio of 45,000:1 for C827 and 500,000:1 for C848 at 2 grams of catalyst suspension per 100 grams of DCPD monomer.

Catalyst Composition (F): catMETium® RF2 was dissolved in toluene. Catalyst Composition (F) was prepared so as to have a monomer to catalyst ratio of 60,000:1 for catMETium® RF2 at 2 grams of catalyst solution per 100 grams of DCPD monomer.

Catalyst Composition (G): C801 was suspended in mineral oil (Crystal Plus 500 FG) containing 2 phr Cab-o-sil TS610. Catalyst composition (G) was prepared so as to have a monomer to catalyst ratio of 5,000:1 for C801 at 2 grams of catalyst suspension per 100 grams of DCPD monomer.

2-Hydroxyethyl bicyclo [2.2.1]hept-2-ene-5-carboxylate (HENB) was prepared as described in WO 2012/174502.

Adhesion Promoter Composition (A). Synthesized HENB (2-hydroxyethyl bicyclo[2.2.1]hept-2-ene-5-carboxylate) (0.10 mol eq., 338 g) was added to liquid MDI (Mondur® MLQ) (1.0 mol eq., 4646 g) at ambient temperature (22-25° C.) and stirred under an inert atmosphere for a minimum of 24 hours. The reaction mixture was used as prepared.

Examples 1-4

Samples of Cyclic Olefin Composition (A) or (B) were placed in a jacketed 1000 mL three neck round bottom flask, cooled to 23.5° C., and degassed under vacuum for 20 minutes. Degassed cyclic olefin composition (A) comprised DCPD (42.99 weight percent), TCPD (55.14 weight percent), and tetracyclopentadiene (1.87 weight percent) as measured by GC. Degassed cyclic olefin composition (B) comprised DCPD (29.78 weight percent), TCPD (67.57 weight percent), and tetracyclopentadiene (2.65 weight percent) as measured by GC. Samples (100 g) of the degassed cyclic olefin compositions (A) or (B) were catalyzed by the addition of 2 grams of either catalyst composition (A) or (B) to form a ROMP composition, which was further degassed for 1 minute under vacuum at 23.5° C. The degassed ROMP composition (23.5° C.) was poured into an aluminum mold (6 inches×4 inches×¼ inches) preheated to 70° C. None of the molded polymer panels possessed visible defects as summarized in Table 1:

TABLE 1

| Example | Cyclic Olefin Composition | Catalyst Composition | Result |
| --- | --- | --- | --- |
| 1 | A | A | no visible defects |
| 2 | A | B | no visible defects |
| 3 | B | A | no visible defects |
| 4 | B | B | no visible defects |

Examples 5-7

Samples of Ultrene® 99 DCPD were melted and combined with Cyclic Olefin Composition (A) or (B) to give the new cyclic olefin compositions indicated in Table 2 below (100 grams). The resulting cyclic olefin compositions were placed in a jacketed 1000 mL three neck round bottom flask, cooled to 23.5° C. and degassed under vacuum for 20 minutes. The compositions (DCPD/TCPD/tetracyclopentadiene) of the resulting degassed cyclic olefin compositions as measured by GC are summarized in Table 2. The degassed cyclic olefin compositions were catalyzed by the addition of 2 grams of catalyst composition (A) or (B) to form a ROMP composition, which was further degassed for 1 minute under vacuum at 23.5° C. The degassed ROMP composition (23.5° C.) was poured into an aluminum mold (6 inches×4 inches×¼ inches) preheated as indicated in Table 3. The results for the resulting molded polymer panels are summarized in Table 3.

TABLE 2

| Example | Ultrene 99 Amount | Cyclic Olefin Composition A/B | Cyclic Olefin Composition Amount | DCPD (wt. %) | TCPD (wt. %) | Tetracyclo-pentadiene (wt. %) |
|---|---|---|---|---|---|---|
| 5 | 63 g | A | 37 g | 77.89 | 20.57 | 0.67 |
| 6 | 63 g | A | 37 g | 77.70 | 20.65 | 0.67 |
| 7 | 45 g | A | 55 g | 68.47 | 30.11 | 1.42 |

TABLE 3

| Example | Catalyst Composition (A/B) | Mold Temperature | Result |
|---|---|---|---|
| 5 | B | 70° C. | visible defects |
| 6 | A | 70° C. | visible defects |
| 7 | B | 60° C. | visible defects |

Examples 8-10

Samples of Ultrene® 99 DCPD were melted and combined with Cyclic Olefin Composition (A) or (B) to give the new cyclic olefin compositions indicated in Table 4 below (100 grams). The resulting cyclic olefin compositions were placed in a jacketed 1000 mL three neck round bottom flask, cooled to 23.5° C. and degassed under vacuum for 20 minutes. The compositions (DCPD/TCPD/tetracyclopentadiene) of the resulting degassed cyclic olefin compositions as measured by GC are summarized in Table 4. Triphenylphosphine (0.6 grams), liquid MDI (4.0 grams), Ethanox 4702 (2.0 grams), and 5-vinyl-2-norbornene (1.0 grams) were added to cyclic olefin composition to give a resin composition. The resin composition was placed in a jacketed 1000 mL three neck round bottom flask, cooled to 23.5° C. and degassed under vacuum for 20 minutes. The resin composition was catalyzed by the addition of catalyst composition (C) (2 grams) to form a ROMP composition, which was further degassed for 1 minute under vacuum at 23.5° C. The degassed ROMP composition (23.5° C.) was poured into an aluminum mold (6 inches×4 inches×¼ inches) preheated as indicated in Table 5. The results for the resulting molded polymer panels are summarized in Table 5.

TABLE 4

| Example | Ultrene 99 Amount | Cyclic Olefin Composition A/B | Cyclic Olefin Composition Amount | DCPD (wt. %) | TCPD (wt. %) | Tetracyclo-pentadiene (wt. %) |
|---|---|---|---|---|---|---|
| 8 | 81.7 g | A | 18.3 g | 89.47 | 10.23 | 0.29 |
| 9 | 8 g | A | 92 g | 47.48 | 50.78 | 1.74 |
| 10 | 13 g | B | 87 g | 38.87 | 58.83 | 2.30 |

TABLE 5

| Example | Catalyst Composition | Mold Temperature | Result |
|---|---|---|---|
| 8 | C | 90° C. | visible defects |
| 9 | C | 90° C. | no visible defects |
| 10 | C | 90° C. | no visible defects |

Example 11

The bottom mold surface of a composite laminate consisted of a sealed and release-treated aluminum plate. The aluminum plate possessed inlet and outlet ports mechanically affixed to the bottom surface of the aluminum plate for resin infusion and vacuum source attachment, respectively. A peel ply (Bron Aerotech; PTFE-coated) was placed on the surface of the aluminum plate. A glass composite laminate was constructed by cutting and arranging fifty plies of glass fabric, each ply having dimensions of 3"×6", on the top surface of the peel ply to achieve approximately 1.5" laminate thickness. Glass fabric was used as supplied by Vectorply (E-LT 3500-10) based on PPG Hybon® 2026 ("Vectorply Glass Fabric"). A peel ply (Bron Aerotech; PTFE-coated) was placed over the fifty plies of glass fabric reinforcement material. Nylon resin distribution media (Airtech Greenflow 75) was positioned on top of the peel ply at opposite ends of the composite laminate corresponding to the position of the inlet port and outlet port, respectively. A sheet of vacuum bagging film (Umeco Process Materials Stretch-Vac 2000) was placed over the completed layup. The vacuum bagging film was affixed to the mold surface using sealant tape (Airtech AT200-Y tape) and a vacuum was applied to the outlet port to evacuate air from the layup to a vacuum level of between 28 inches-Hg to 29 inches-Hg.

Ultrene® R® 99 DCPD (44 grams) was melted and combined with cyclic olefin composition (B) (356 grams) which, after degassing, comprised DCPD (37.50 weight percent), TCPD (59.96 weight percent), and tetracyclopentadiene (2.54 weight percent). TPP (2.4 grams), liquid MDI (16.0 grams), Ethanox 4702 (8.0 grams), and 5-vinyl-2-norbornene (4.0 grams) were then added to give a formulated resin composition, which was then degassed under vacuum for 20 minutes at ambient temperature (20-25° C.) with stirring. The resin composition was catalyzed by the addition of catalyst composition (C) (8 grams) to form a ROMP composition, which was further degassed for at least one minute under vacuum at ambient temperature (20-25° C.) with stirring. After at least one minute, stirring of the ROMP composition was stopped, the vacuum source was clamped off, and the ROMP composition was backfilled with argon. The ROMP composition (20-25° C.) was then infused in to the glass fabric, driven by the pressure gradient between the ambient pressure and the evacuated glass fabric layup. After the infusion was complete, the glass composite laminate was heated to 100° C. at a heating rate of 1° C./min and held at 100° C. for 1 hour and then allowed to cool to ambient temperature (20-25° C.) and subsequently demolded. The demolded glass composite laminate did not possess visible defects.

Example 12

Cyclic olefin composition (A) (100.0 grams) was placed in a jacketed 1000 mL three neck round bottom flask. Degassed cyclic olefin composition (A) comprised DCPD (42.99 weight percent), TCPD (55.14 weight percent), and tetracyclopentadiene (1.87 weight percent) as measured by GC. TPP (0.6 grams), adhesion promoter composition (A) (4.0 grams), Ethanox 4702 (2.0 grams), and 5-vinyl-2-norbornene (1.0 grams) were added to cyclic olefin composition (A) to give a resin composition. The resin composition was cooled to 23.5° C. and degassed under vacuum for 20 minutes. The resin composition was catalyzed by the addition of catalyst composition (C) (2 grams) to form a ROMP composition, which was further degassed for 1 minute under vacuum at 23.5° C. The degassed ROMP composition (23.5° C.) was poured into an aluminum mold (6 inches×4 inches×

¼ inches) preheated to 90° C. The molded polymer panel did not possess visible defects.

Example 13

The bottom mold surface of a composite laminate consisted of a sealed and release-treated aluminum plate. The aluminum plate possessed inlet and outlet ports mechanically affixed to the bottom surface of the aluminum plate for resin infusion and vacuum source attachment, respectively. A peel ply (Bron Aerotech; PTFE-coated) was placed on the surface of the aluminum plate. A glass composite laminate was constructed by cutting and arranging fifty plies of glass fabric, each ply having dimensions of 3"×6", on the top surface of the peel ply to achieve approximately 1.5" laminate thickness. Glass fabric was used as supplied by Vectorply (E-LT 3500-10) based on PPG Hybon® 2026 ("Vectorply Glass Fabric"). A peel ply (Bron Aerotech; PTFE-coated) was placed over the fifty plies of glass fabric reinforcement material. Nylon resin distribution media (Airtech Greenflow 75) was positioned on top of the peel ply at opposite ends of the composite laminate corresponding to the position of the inlet port and outlet port, respectively. A sheet of vacuum bagging film (Umeco Process Materials Stretch-Vac 2000) was placed over the completed layup. The vacuum bagging film was affixed to the mold surface using sealant tape (Airtech AT200-Y tape) and a vacuum was applied to the outlet port to evacuate air from the layup to a vacuum level of between 28 inches-Hg to 29 inches-Hg.

Cyclic olefin composition (A) (500.0 grams) was placed in a 1000 mL three neck round bottom flask. Degassed cyclic olefin composition (A) comprised DCPD (42.99 weight percent), TCPD (55.14 weight percent), and tetracyclopentadiene (1.87 weight percent) as measured by GC. TPP (3.0 grams), adhesion promoter composition (A) (20.0 grams), Ethanox 4702 (10.0 grams), and 5-vinyl-2-norbornene (5.0 grams) were added to cyclic olefin composition (A) to give a resin composition. The resin composition was degassed under vacuum for 20 minutes at ambient temperature (20-25° C.) with stirring. The resin composition was catalyzed by the addition of catalyst composition (C) (10 grams) to form a ROMP composition, which was further degassed for at least one minute under vacuum at ambient temperature (20-25° C.) with stirring. After at least one minute, stirring of the ROMP composition was stopped, the vacuum source was clamped off, and the ROMP composition was backfilled with argon. The ROMP composition (20-25° C.) was then infused in to the glass fabric, driven by the pressure gradient between the ambient pressure and the evacuated glass fabric layup. After the infusion was complete, the glass composite laminate was heated to 100° C. at a heating rate of 1° C./min and held at 100° C. for 1 hour and then allowed to cool to ambient temperature (20-25° C.) and subsequently demolded. The demolded glass composite laminate did not possess visible defects

Example 14

The bottom mold surface of a composite laminate consisted of a sealed and release-treated epoxy composite material. Two plies of ELT-3500 unidirectional glass fabric (12.5"×26") were placed on the epoxy composite plate. Two 1" thick sections of PVC core material (12.5"×12.5") were placed on one half section of the ELT-3500 glass fabric. 100 plies of ELT-1800 unidirectional glass fabric (12.5"×12.5") were placed on the other one half section of the ELT-3500 glass fabric. Two plies of ELT-3500 glass fabric (12.5"×28") were placed on top of the PVC core material and ELT-1800 glass fabric stack. Peel ply was placed over the PVC core-glass fabric composite layup. Two layers infusion media (11.5"×27.5") was placed on top of the peel ply. A sheet of vacuum bagging film (Umeco Process Materials Stretch-Vac 2000) was placed over the completed layup. The vacuum bagging film was affixed to the mold surface using sealant tape (Airtech AT200-Y tape) and a vacuum was applied to the outlet port to evacuate air from the layup to a vacuum level of between 28 inches-Hg to 29 inches-Hg.

A first cyclic olefin composition (7132 grams) comprising DCPD (30.05 weight percent), TCPD (64.97 weight percent, and tetracyclopentadiene (4.97 weight percent) as measured by GC was combined with a second cyclic olefin composition (2868 grams) comprising DCPD (75.19 weight percent), TCPD (22.33 weight percent), and tetracyclopentadiene (2.47 weight percent) as measured by GC to provide a new cyclic olefin composition (10 kg) comprising DCPD (43.00 weight percent), TCPD (52.74 weight percent) and tetracyclopentadiene (4.26 weight percent) as calculated. The new cyclic olefin composition was a heterogenous mixture at room temperature (20-25° C.) (i.e., a clear liquid containing white solids). TPP (66 grams), adhesion promoter composition (A) (400 grams), Ethanox 4702 (200 grams), and 5-vinyl-2-norbornene (100 grams) were added to the new cyclic olefin composition to give a resin composition. The resin composition was degassed under vacuum for 20 minutes with stirring. The resin composition was catalyzed by the addition of catalyst composition (A) (200 grams) to form a ROMP composition, which was further degassed for at least one minute under vacuum with stirring. After at least one minute, stirring of the ROMP composition was stopped, the vacuum source was clamped off, and the ROMP composition was backfilled with ambient air. The ROMP composition (20-25° C.) was then infused in to the composite layup driven by the pressure gradient between the ambient pressure and the evacuated composite layup. After the infusion was complete, the composite layup was heated to 100° C. at a heating rate of 1° C./min and held at 100° C. for 30 minutes and then allowed to cool to ambient temperature (20-25° C.) and subsequently demolded. The demolded glass composite laminate possessed visible defects. Moreover, during the infusion white solids precipitated out of the ROMP composition and created difficulty during the infusion, particularly the white solids collected in the resin infusion media thereby slowing the flow of resin into the composite layup (infusion time post catalyzation was 90 minutes).

Examples 15-20

Cyclic Olefin Composition (C) was degassed under vacuum for 20 minutes at ambient temperature (20-25° C.). Degassed cyclic olefin composition (C) comprised DCPD (37.17 weight percent), TCPD (59.28 weight percent), and TeCPD (3.55 weight percent) as measured by GC. Six separate samples (100 grams per sample) of the degassed cyclic olefin composition (C) were catalyzed by the addition of 2 grams of catalyst composition (A), (B), (D), (E), (F), or (G) to form six independent ROMP compositions at ambient temperature (20-25° C.). The six independent ROMP compositions were each poured into six separate aluminum molds (6 inches×4 inches×¼ inches) preheated to 70° C. The results for the resulting molded polymer panels are summarized in Table 6.

TABLE 6

| Example | Catalyst Composition | Result |
|---|---|---|
| 15 | A | substantially free of defects |
| 16 | B | no visible defects |
| 17 | D | no visible defects |
| 18 | E | no visible defects |
| 19 | F | no visible defects |
| 20 | G | no visible defects |

Example 21

Cyclic Olefin Composition (E) was degassed under vacuum for 20 minutes at ambient temperature (20-25° C.). Degassed cyclic olefin composition (E) comprised DCPD (79.88 weight percent) and TCPD (20.12 weight percent) as measured by GC. Degassed cyclic olefin composition (E) (100 grams) was catalyzed by the addition of 2 grams of catalyst composition (D) to form a ROMP composition at ambient temperature (20-25° C.). The ROMP composition was poured into an aluminum mold (6 inches×4 inches×¼ inches) preheated to 70° C. The molded polymer panel possessed visible defects.

Examples 22-23

Cyclic Olefin Composition (C) was degassed under vacuum for 20 minutes at ambient temperature (20-25° C.). Degassed cyclic olefin composition (C) comprised DCPD (37.17 weight percent), TCPD (59.28 weight percent), and TeCPD (3.55 weight percent) as measured by GC. Degassed cyclic olefin composition (C) (600 grams) was catalyzed by the addition of 12 grams of catalyst composition (D) to form a ROMP composition at ambient temperature (20-25° C.). The ROMP composition was poured into an aluminum mold (1.5 inches×1.5 inches×12 inches) preheated to 70° C. The result for the resulting molded polymer panel is summarized in Table 7.

Cyclic Olefin Composition (F) was degassed under vacuum for 20 minutes at ambient temperature (20-25° C.). Degassed cyclic olefin composition (F) comprised DCPD (66.00 weight percent), TCPD (31.54 weight percent), and TeCPD (2.46 weight percent) as measured by GC. Degassed cyclic olefin composition (F) (600 grams) was catalyzed by the addition of 12 grams of catalyst composition (D) to form a ROMP composition at ambient temperature (20-25° C.). The ROMP composition was poured into an aluminum mold (1.5 inches×1.5 inches×12 inches) preheated to 70° C. The result for the resulting molded polymer panel is summarized in Table 7.

TABLE 7

| Example | Catalyst Composition | Cyclic Olefin Composition | Result |
|---|---|---|---|
| 22 | D | C | no visible defects |
| 23 | D | F | visible defects |

Example 24

Cyclic Olefin Composition (G) was degassed under vacuum for 20 minutes at ambient temperature (20-25° C.). Degassed cyclic olefin composition (G) comprised DCPD (58.58 weight percent), TCPD (39.44 weight percent), and TeCPD (1.98 weight percent) as measured by GC. Degassed cyclic olefin composition (G) (100 grams) was catalyzed by the addition of 2 grams of catalyst composition (G) to form a ROMP composition at ambient temperature (20-25° C.). The ROMP composition was poured into an aluminum mold (6 inches×4 inches×¼ inches) preheated to 70° C. The molded polymer panel possessed no visible defects.

Example 25

Cyclic Olefin Composition (C) was degassed under vacuum for 20 minutes at ambient temperature (20-25° C.). Degassed cyclic olefin composition (C) comprised DCPD (37.17 weight percent), TCPD (59.28 weight percent), and TeCPD (3.55 weight percent) as measured by GC. Degassed cyclic olefin composition (C) (50 grams) was catalyzed by the addition of 1 gram of catalyst composition (G) to form a ROMP composition at ambient temperature (20-25° C.). The ROMP composition was poured into an aluminum mold (6 inches×4 inches×⅛ inches) preheated to 70° C. The molded polymer panel possessed no visible defects.

Example 26

Cyclic Olefin Composition (D) was degassed under vacuum for 20 minutes at ambient temperature (20-25° C.). Degassed cyclic olefin composition (D) comprised DCPD (90.04 weight percent) and TCPD (9.96 weight percent) as measured by GC. Degassed cyclic olefin composition (D) (100 grams) was catalyzed by the addition of 2 grams of catalyst composition (G) to form a ROMP composition at ambient temperature (20-25° C.). The ROMP composition was poured into an aluminum mold (6 inches×4 inches×¼ inches) preheated to 70° C. The molded polymer panel possessed no visible defects.

Examples 27-29

Flash point measurements of DCPD resins showing increase in Flash Point with decreasing DCPD content as measured according to ASTM D93 (Pensky Martens method), Table 8.

TABLE 8

| Example | DCPD Content (wt. %) | Flash Point (° C.) |
|---|---|---|
| 27 | 74.0 | 41 |
| 28 | 41.0 | 58 |
| 29 | 26.0 | 60 |

Examples 30-31

Flash point measurements of resin compositions showing increase in Flash Point with increasing TCPD content (decreasing DCPD content) as measured according to ASTM D93 (Pensky Martens method), Table 9.

TABLE 9

| Example | DCPD (wt. %) | TCPD (wt. %) | TeCPD (wt. %) | [a]Additive Package (wt. %) | Flash Point (° C.) |
|---|---|---|---|---|---|
| 30 | 39.0 | 50.3 | 3.6 | 7.1 | 54 |
| 31 | 20.0 | 70.0 | 2.9 | 7.1 | 66 |

[a] = Ethanox 4702 (2 phr); 5-vinyl-2-norbornene (1 phr); adhesion promoter composition (A) (4 phr); TPP (0.6 phr)

Example 32

Degassed cyclic olefin composition (G) comprised DCPD (58.58 weight percent), TCPD (39.44 weight percent), and TeCPD (1.98 weight percent) as measured by GC was a homogenous, transparent, colorless liquid at ambient temperature (20-25° C.). Two (10 mL aliquots) of cyclic olefin composition (G) were placed in separate glass vials and sealed with screw top lids. One aliquot was stored at ambient temperature (20-25° C.), the other aliquot was stored at 10° C. After 24 hours both aliquots were homogenous, transparent, colorless liquids.

A cyclic olefin composition (26 grams) comprising 25 wt % DCPD and 75 wt % TCPD as calculated was heated to 70° C. to prepare a homogeneous, transparent, colorless liquid. Two (10 mL aliquots) of this cyclic olefin composition (25 wt % DCPD and 75 wt % TCPD) were placed in separate glass vials and sealed with screw top lids. One aliquot was stored at ambient temperature (20-25° C.), the other aliquot was stored at 10° C. After 5 hours the aliquot stored at ambient temperature (20-25° C.) was a heterogeneous mixture containing a transparent, colorless liquid and white solid precipitate. After 5 hours the aliquot stored at 10° C. was a white solid.

The claimed invention is:

1. A ring opening metathesis polymerization (ROMP) composition, comprising a catalyst composition comprising at least one metal carbene olefin metathesis catalyst, and a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins.

2. The composition of claim 1, wherein the one or more other cyclic olefins is selected from dicyclopentadiene.

3. The composition of claim 1, wherein the cyclic olefin composition comprises 35.00% to 70.00% by weight tricyclopentadiene, 0.01% to 4.00% by weight tetracyclopentadiene, and 64.99% to 26.00% by weight dicyclopentadiene.

4. The composition of claim 1, wherein the at least one metal carbene olefin metathesis catalyst is a Group 8 transition metal complex having the structure of formula (I)

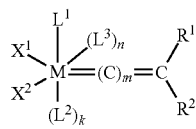

in which:
M is a Group 8 transition metal;
$L^1$, $L^2$, and $L^3$ are neutral electron donor ligands;
n is 0 or 1, such that $L^3$ may or may not be present;
m is 0, 1, or 2;
k is 0 or 1;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, or functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

5. The composition of claim 4, wherein $R^1$ and $R^2$ are taken together to form an indenylidene moiety.

6. The composition of claim 4, wherein $L^1$ is carbene ligand having the structure of formula (II)

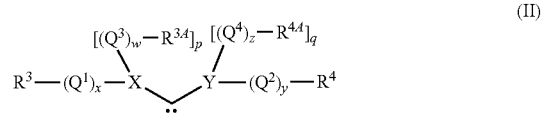

wherein,
X and Y are heteroatoms selected from N, O, S, or P;
p is zero when X is O or S, and p is 1 when X is N or P;
q is zero when Y is O or S, and q is 1 when Y is N or P;
$Q^1$, $Q^2$, $Q^3$, and $Q^4$ are linkers selected from hydrocarbylene, substituted hydrocarbylene, heteroatom containing hydrocarbylene, or substituted heteroatom-containing hydrocarbylene, and —(CO)—, and further wherein two or more substituents on adjacent atoms within $Q^1$, $Q^2$, $Q^3$, and $Q^4$ may be linked to form an additional cyclic group;
w, x, y, and z are independently zero or 1; and
$R^3$, $R^{3A}$, $R^4$, and $R^{4A}$ are independently selected from hydrogen, hydrocarbyl, substituted hydrocarbyl, heteroatom-containing hydrocarbyl, or substituted heteroatom-containing hydrocarbyl,
wherein any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $Q^3$, and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

7. The composition of claim 4, wherein $L^1$ is an N-heterocyclic carbene ligand.

8. A method for making a ring opening metathesis polymerization (ROMP) polymer, comprising providing a catalyst composition comprising at least one metal carbene olefin metathesis catalyst, providing a resin composition comprising a cyclic olefin composition, wherein the cyclic olefin composition comprises 35.00% to 70.00% by weight tricyclopentadiene, 0.01% to 4.00% by weight tetracyclopentadiene, and up to 64.99% by weight of one or more other cyclic olefins, combining the catalyst composition and the resin composition to form a ROMP composition, and subjecting the ROMP composition to conditions effective to promote polymerization of the ROMP composition.

9. The method of claim 8, wherein the one or more other cyclic olefins is selected from dicyclopentadiene.

10. The method of claim 8, wherein the cyclic olefin composition comprises 35.00% to 70.00% by weight tricyclopentadiene, 0.01% to 4.00% by weight tetracyclopentadiene, and 64.99% to 26.00% by weight dicyclopentadiene.

11. The method of claim 8, wherein the at least one metal carbene olefin metathesis catalyst is a Group 8 transition metal complex having the structure of formula (I)

in which:
M is a Group 8 transition metal;
$L^1$, $L^2$, and $L^3$ are neutral electron donor ligands;
n is 0 or 1, such that $L^3$ may or may not be present;

m is 0, 1, or 2;

k is 0 or 1;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, or functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

12. The method of claim 11, wherein $R^1$ and $R^2$ are taken together to form an indenylidene moiety.

13. The method of claim 11, wherein $L^1$ is carbene ligand having the structure of formula (II)

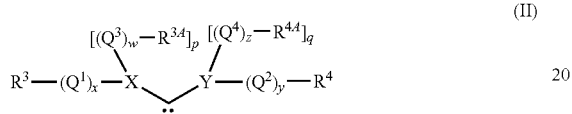
(II)

wherein,

X and Y are heteroatoms selected from N, O, S, or P;

p is zero when X is O or S, and p is 1 when X is N or P;

q is zero when Y is O or S, and q is 1 when Y is N or P;

$Q^1$, $Q^2$, $Q^3$, and $Q^4$ are linkers selected from hydrocarbylene, substituted hydrocarbylene, heteroatom containing hydrocarbylene, or substituted heteroatom-containing hydrocarbylene, and —(CO)—, and further wherein two or more substituents on adjacent atoms within $Q^1$, $Q^2$, $Q^3$, and $Q^4$ may be linked to form an additional cyclic group;

w, x, y, and z are independently zero or 1; and $R^3$, $R^{3A}$, $R^4$, and $R^{4A}$ are independently selected from hydrogen, hydrocarbyl, substituted hydrocarbyl, heteroatom-containing hydrocarbyl, or substituted heteroatom-containing hydrocarbyl, wherein any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $Q^3$, and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

14. The method of claim 11, wherein $L^1$ is an N-heterocyclic carbene ligand.